US007030082B2

(12) United States Patent
Soltero et al.

(10) Patent No.: US 7,030,082 B2
(45) Date of Patent: Apr. 18, 2006

(54) PHARMACEUTICAL COMPOSITIONS OF DRUG-OLIGOMER CONJUGATES AND METHODS OF TREATING DISEASE THEREWITH

(75) Inventors: Richard Soltero, Holly Springs, NC (US); Nnochiri N. Ekwuribe, Cary, NC (US); Foyeke Opawale, Raleigh, NC (US); Bruce Rehlaender, Chapel Hill, NC (US); Anthony Hickey, Chapel Hill, NC (US); Li Li Bovet, Chapel Hill, NC (US)

(73) Assignee: Nobex Corporation, Durham, NC (US)

( * ) Notice: Subject to any disclaimer, the term of this patent is extended or adjusted under 35 U.S.C. 154(b) by 151 days.

(21) Appl. No.: 10/382,069

(22) Filed: Mar. 5, 2003

(65) Prior Publication Data
US 2004/0017387 A1    Jan. 29, 2004

Related U.S. Application Data

(63) Continuation-in-part of application No. 10/235,381, filed on Sep. 5, 2002, now Pat. No. 6,867,183, and a continuation-in-part of application No. 10/235,284, filed on Sep. 5, 2002, now Pat. No. 6,770,625.

(60) Provisional application No. 60/377,865, filed on May 3, 2002, provisional application No. 60/318,193, filed on Sep. 7, 2001.

(51) Int. Cl.
*A61K 38/02* (2006.01)
*A61K 38/23* (2006.01)

(52) U.S. Cl. .............................. 514/2; 514/12; 514/21; 514/784; 514/785

(58) Field of Classification Search .................... 514/2, 514/12, 21, 784, 785; 530/307, 345, 408, 530/409, 410, 411
See application file for complete search history.

(56) References Cited

U.S. PATENT DOCUMENTS

| | | | |
|---|---|---|---|
| 4,156,719 A | 5/1979 | Sezaki et al. | 424/118 |
| 4,179,337 A | 12/1979 | Davis et al. | 435/181 |
| 4,338,306 A | 7/1982 | Kitao et al. | 424/178 |

(Continued)

FOREIGN PATENT DOCUMENTS

GB         2257908 A  *  1/1993

(Continued)

OTHER PUBLICATIONS

International Search Report for International Application No. PCT/US02/28429 dated Mar. 14, 2003.

(Continued)

*Primary Examiner*—Jeffrey Edwin Russel
(74) *Attorney, Agent, or Firm*—William A. Barrett; Jerry W. Clark; Moore & Van Allen PLLC

(57) ABSTRACT

Pharmaceutical compositions that include a drug and/or drug-oligomer conjugate, a fatty acid component and a bile salt component, or a bile salt component without a fatty acid component are described. The drug can be covalently coupled to an oligomeric moiety. The fatty acid component and the bile salt component, when together, can be present in a weight-to-weight ratio of between 1:15 and 15:1 or any value between. Methods of treating diseases in a subject in need of such treatment using the pharmaceutical compositions of this invention are also provided, as well as methods of providing such pharmaceutical compositions.

72 Claims, 19 Drawing Sheets

U.S. PATENT DOCUMENTS

| | | | |
|---|---|---|---|
| 4,348,387 A | 9/1982 | Brownlee et al. | 424/178 |
| 4,469,681 A | 9/1984 | Brownlee et al. | 424/178 |
| 4,472,382 A | 9/1984 | Labrie et al. | 424/177 |
| 4,579,730 A | 4/1986 | Kidron et al. | 424/19 |
| 4,839,341 A | 6/1989 | Massey et al. | 514/4 |
| 4,849,405 A | 7/1989 | Ecanow | 514/3 |
| 4,917,888 A | 4/1990 | Katre et al. | 424/85.91 |
| 4,957,910 A | 9/1990 | Sutton et al. | 514/182 |
| 4,994,439 A | 2/1991 | Longenecker et al. | 514/3 |
| 5,089,261 A | 2/1992 | Nitecki et al. | 424/85.2 |
| 5,162,430 A | 11/1992 | Rhee et al. | 525/54.1 |
| 5,164,366 A | 11/1992 | Balschmidt et al. | 514/3 |
| 5,250,236 A * | 10/1993 | Gasco | 264/4.4 |
| 5,283,236 A | 2/1994 | Chiou | 514/2 |
| 5,286,637 A | 2/1994 | Veronese et al. | 435/183 |
| 5,312,808 A | 5/1994 | Shorr et al. | 514/6 |
| 5,328,955 A | 7/1994 | Rhee et al. | 525/54.1 |
| 5,359,030 A | 10/1994 | Ekwuribe | 530/303 |
| 5,405,621 A | 4/1995 | Sipos | 424/490 |
| 5,405,877 A | 4/1995 | Greenwald et al. | 514/772.3 |
| 5,415,872 A | 5/1995 | Sipos | 424/490 |
| 5,438,040 A | 8/1995 | Ekwuribe | 514/3 |
| 5,461,031 A | 10/1995 | De Felippis | 514/4 |
| 5,468,478 A | 11/1995 | Saifer et al. | 424/78.27 |
| 5,504,188 A | 4/1996 | Baker et al. | 530/304 |
| 5,506,203 A | 4/1996 | Bäckström et al. | 514/4 |
| 5,518,998 A | 5/1996 | Bäckström et al. | 514/3 |
| 5,523,348 A | 6/1996 | Rhee et al. | 525/54.1 |
| 5,529,915 A | 6/1996 | Phillips et al. | 435/188 |
| 5,567,422 A | 10/1996 | Greenwald | 424/78.3 |
| 5,612,460 A | 3/1997 | Zalipsky | 530/391.9 |
| 5,631,347 A | 5/1997 | Baker et al. | 530/303 |
| 5,637,749 A | 6/1997 | Greenwald | 558/6 |
| 5,646,242 A | 7/1997 | Baker et al. | 530/303 |
| 5,650,388 A | 7/1997 | Shorr et al. | 514/6 |
| 5,658,878 A | 8/1997 | Bäckström et al. | 514/3 |
| 5,681,567 A | 10/1997 | Martinez et al. | 424/178.1 |
| 5,693,609 A | 12/1997 | Baker et al. | 514/3 |
| 5,700,904 A | 12/1997 | Baker et al. | 530/305 |
| 5,738,846 A | 4/1998 | Greenwald et al. | 424/85.7 |
| 5,747,445 A | 5/1998 | Bäckström et al. | 514/4 |
| 5,747,642 A | 5/1998 | De Felippis | 530/304 |
| 5,766,620 A | 6/1998 | Heiber et al. | 424/436 |
| 5,830,853 A | 11/1998 | Bäckström et al. | 514/4 |
| 5,849,860 A | 12/1998 | Hakimi et al. | 528/370 |
| 5,853,748 A | 12/1998 | New | 424/439 |
| 5,854,208 A | 12/1998 | Jones et al. | 514/3 |
| 5,856,451 A | 1/1999 | Olsen et al. | 530/402 |
| 5,863,555 A * | 1/1999 | Heiber et al. | 424/435 |
| 5,866,538 A | 2/1999 | Norup et al. | 514/3 |
| 5,898,028 A | 4/1999 | Jensen et al. | 514/4 |
| 5,902,588 A | 5/1999 | Greenwald et al. | 424/278.1 |
| 5,932,462 A | 8/1999 | Harris et al. | 435/188 |
| 5,942,248 A | 8/1999 | Barnwell | 424/457 |
| 5,948,751 A | 9/1999 | Kimer et al. | 514/4 |
| 5,952,008 A | 9/1999 | Bäckström et al. | 424/499 |
| 5,952,297 A | 9/1999 | De Felippis et al. | 514/3 |
| 5,968,549 A | 10/1999 | New et al. | 424/450 |
| 5,969,040 A | 10/1999 | Hallahan et al. | 525/54.1 |
| 5,981,709 A | 11/1999 | Greenwald et al. | 530/351 |
| 5,985,263 A | 11/1999 | Lee et al. | 424/85.2 |
| 6,004,574 A | 12/1999 | Bäckström et al. | 424/434 |
| 6,025,325 A | 2/2000 | Campfield et al. | 514/2 |
| 6,034,054 A | 3/2000 | DeFelippis et al. | 514/4 |
| 6,043,214 A | 3/2000 | Jensen et al. | 514/3 |
| 6,051,551 A | 4/2000 | Hughes et al. | 514/3 |
| 6,063,761 A | 5/2000 | Jones et al. | 514/3 |
| 6,093,391 A | 7/2000 | Kabanov et al. | 424/85.1 |
| 6,113,906 A | 9/2000 | Greenwald et al. | 424/194.1 |
| 6,165,976 A | 12/2000 | Bäckström et al. | 514/3 |
| 6,177,087 B1 | 1/2001 | Greenwald et al. | 424/278.1 |
| 6,191,105 B1 | 2/2001 | Ekwuribe et al. | 514/3 |
| 6,200,602 B1 | 3/2001 | Watts et al. | 424/463 |
| 6,210,699 B1 * | 4/2001 | Acharya et al. | 424/435 |
| 6,211,144 B1 | 4/2001 | Havelund | 514/4 |
| 6,248,363 B1 | 6/2001 | Patel et al. | 424/497 |
| 6,251,856 B1 | 6/2001 | Markussen et al. | 514/3 |
| 6,255,502 B1 | 7/2001 | Penkler et al. | 552/549 |
| 6,258,377 B1 | 7/2001 | New et al. | 424/450 |
| 6,268,335 B1 | 7/2001 | Brader | 514/3 |
| 6,306,440 B1 | 10/2001 | Bäckström et al. | 424/499 |
| 6,309,663 B1 | 10/2001 | Patel et al. | 424/450 |
| 6,310,038 B1 | 10/2001 | Havelund | 514/4 |
| 6,323,311 B1 | 11/2001 | Liu et al. | 530/303 |
| 6,335,316 B1 | 1/2002 | Hughes et al. | 514/3 |
| 6,673,574 B1 * | 1/2004 | Stern et al. | 435/69.7 |
| 2002/0018811 A1 | 2/2002 | Penteado et al. | 424/474 |
| 2003/0050228 A1 * | 3/2003 | Ekwuribe et al. | 514/3 |
| 2003/0060606 A1 | 3/2003 | Ekwuribe et al. | 530/399 |
| 2003/0083232 A1 * | 5/2003 | Soltero et al. | 514/3 |
| 2003/0228275 A1 * | 12/2003 | Ekwuribe et al. | 424/78.38 |
| 2004/0091452 A1 * | 5/2004 | Ekwuribe et al. | 424/78.37 |

FOREIGN PATENT DOCUMENTS

| | | |
|---|---|---|
| JP | 52067313 A | 5/1977 |
| WO | WO 00/078302 A1 | 12/2000 |

OTHER PUBLICATIONS

International Search Report for International Application No. PCT/US02/28536 dated Sep. 15, 2003.

Baudy's et al. "Stabilization and Intestinal Absorption of Human Calcitonin" *J. Contr. Rel.* 39:145-51 (1996).

Ekwuribe and Radhakrishnan "Calcitonin Drug-Oligomer Conjugates, and Uses Thereof" U.S. Appl. No. 10/166,355, filed Nov. 8, 2002.

Savva & Huang "Effect of PEG Homopolymer and Grafted Amphiphilic PEG-Palmityl on the Thermotropic Phase Behavior of 1,2-Dipalmitoyl-SN-Glycero-3-Phosphocholine Bilayer" *Journal of Liposome Research* 9(3):357-365 (1999).

* cited by examiner

PHARMACEUTICAL COMPOSITIONS OF DRUG-OLIGOMER CONJUGATES AND METHODS OF TREATING DISEASE THEREWITH

RELATED APPLICATION

This application is a continuation-in-part application of U.S. application Ser. No. 10/235,381, filed Sep. 5, 2002, now U.S. Pat. No. 6,867,183, and U.S. application Ser. No. 10/235,284, filed Sep. 5. 2002, now U.S. Pat. No. 6,770,625 to Soltero et al and which claim the benefit of U.S. Provisional Application No. 60/318,193, filed Sep. 7, 2001 and U.S. Provisional Application No. 60/377,865, filed May 3, 2002, the disclosures of each of which are incorporated herein by reference in their entireties.

FIELD OF THE INVENTION

The present invention relates to pharmaceutical compositions and methods of treating diseases therewith.

BACKGROUND OF THE INVENTION

Fatty acids have been proposed as excipients in pharmaceutical compositions of unconjugated drug molecules. For example, U.S. Pat. No. 4,338,306 to Kitao et al. proposes pharmaceutical compositions for rectal administration of insulin. The pharmaceutical compositions include insulin and fatty acids having 8 to 14 carbon atoms and nontoxic salts thereof.

U.S. Pat. No. 5,658,878 to Bäckström et al. proposes a therapeutic preparation for inhalation that includes insulin and a substance which enhances the absorption of insulin in the lower respiratory tract. The enhancer can be a sodium salt of a saturated fatty acid of carbon chain length 10 (i.e., sodium caprate), 12 (sodium laurate), or 14 (sodium myristate). Potassium and lysine salts of capric acid are also proposed. Bäckström et al. notes that if the carbon chain length is shorter than about 10, the surface activity of the surfactant may be too low, and if the chain length is longer than about 14, decreased solubility of the fatty acid in water limits its usefulness. As an alternative to the proposed fatty acid enhancers, Bäckström et al. proposes the use of the following bile salts—sodium ursodeoxycholate, sodium taurocholate, sodium glycocholate, and sodium taurodihydrofusidate.

U.S. Pat. No. 6,200,602 to Watts et al. proposes drug delivery compositions for colonic delivery of insulin. The drug delivery compositions include insulin, an absorption promoter which (a) includes a mixture of fatty acids having 6 to 16 carbon atoms or a salt thereof and a dispersing agent, or (b) comprises a mixture of mono/diglycerides of medium chain fatty acids and a dispersing agent, and a coating to prevent the release of the insulin and absorption promoter until the tablet, capsule or pellet reaches the proximal colon.

Bile salts have been proposed as excipients in pharmaceutical compositions of unconjugated drug molecules. For example, U.S. Pat. No. 4,579,730 to Kidron et al. proposes pharmaceutical compositions for the oral administration of insulin. The pharmaceutical compositions include insulin, a bile acid or alkali metal salt thereof, the bile acid being selected from the group consisting of cholic acid, chenodeoxychoic acid, taurocholic acid, taurochenodeoxycholic acid, glycocholic acid, glycochenocholic acid, 3β-hydroxy-12-ketocholic acid, 12α-3β-dihydrocholic acid, and ursodesoxycholic acid, and a protease inhibitor. The composition is provided with an enterocoating to assure passage through the stomach and release in the intestine.

U.S. Pat. No. 5,283,236 to Chiou proposes compositions for systemic delivery of insulin through the eyes where the drug passes into the nasolacrimal duct and becomes absorbed into circulation. The composition includes insulin and an enhancing agent. The enhancing agents proposed include, either alone or in combination, surfactants such as polyoxyethylene ethers of fatty acids, and bile salts and acids such as cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurodeoxycholate, chenodeoxycholic acid, and ursodeoxycholic acid. The enhancer is present in a concentration ranging from 0.1% to 5% (w/v).

U.S. Pat. No. 5,853,748 to New proposes enteric-coated compositions for oral administration of insulin. The composition includes insulin, a bile salt or bile acid, and carbonate or bicarbonate ions, which are used to adjust the pH of the gut to a pH of from 7.5 to 9.

In at least one instance, a mixture of a low detergent bile salt, such as ursodeoxycholate, and a $C_{12}$ to $C_{24}$ fatty acid, such as linoleic or oleic acid, has been proposed as an excipient in a pharmaceutical composition of orally active pharmaceutically active agents that need to be protected from the acidic and enzymatic environment of the stomach and for which the gastrointestinal mucosa should be protected from adverse effects of the drug. The described pharmaceutical composition is proposed to be particularly suitable for the non-steroidal anti-inflammatory drug, indomethacin.

It is desirable to provide pharmaceutical compositions for administration of drug-oligomer conjugates.

SUMMARY OF THE INVENTION

Pharmaceutical compositions according to certain embodiments of the present invention use a mixture of bile salts and fatty acids in a particular ratio that appears to provide synergistic effects in the administration of drug and/or drug-oligomer conjugates that can not be achieved with bile salts or fatty acids alone. For example, in some embodiments of the present invention, using mixtures of bile salts and fatty acids in a particular ratio alters the precipitation characteristics of the bile salt so that the bile salt more readily re-solubilizes if it happens to precipitate out of the pharmaceutical composition (e.g., upon encountering an acidic environment in the gut). As another example, in some embodiments of the present invention, using mixtures of bile salts and fatty acids in a particular ratio lowers the precipitation point of the bile salt in the pharmaceutical composition, providing additional buffering capacity for the pharmaceutical composition.

According to embodiments of the present invention, a pharmaceutical composition includes a drug and/or drug-oligomer conjugate that includes a drug covalently coupled to an oligomeric moiety, a fatty acid component that includes a fatty acid, and a bile salt component that includes a bile salt or a bile salt. The fatty acid component and the bile salt component, when together, are present in a weight-to-weight ratio of between 1:15 and 15:1. The fatty acid component is present in an amount sufficient to lower the precipitation point of the bile salt compared to a precipitation point of the bile salt if the fatty acid component were not present in the pharmaceutical composition. The bile salt component is present in an amount sufficient to lower the solubility point of the fatty acid compared to a solubility point of the fatty acid if the bile salt were not present in the pharmaceutical composition.

According to other embodiments of the present invention, a pharmaceutical composition includes a drug and/or drug-oligomer conjugate that includes a drug covalently coupled to an oligomeric moiety, a bile salt component that includes a bile salt, and a fatty acid component that includes a fatty acid, or a bile salt. The fatty acid component and the bile salt component, when together, are present in a weight-to-weight ratio of between 1:15 and 15:1. The fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were present in a second amount less than the first amount.

According to still other embodiments of the present invention, a pharmaceutical composition includes a drug and/or drug-oligomer conjugate that includes a drug covalently coupled to an oligomeric moiety, between 0.1 and 15% (w/v) of a fatty acid component, and between 0.1 and 15% (w/v) of a bile salt component or a bile salt alone. The fatty acid component and the bile salt component, when together, are present in a weight-to-weight ratio of between 1:15 and 15:1.

According to other embodiments of the present invention, methods of treating a disease state in a subject in need of such treatment include administering to the subject a pharmaceutical composition according to embodiments of the present invention.

According to still other embodiments of the present invention, a method of providing a pharmaceutical composition includes selecting an amount of a bile salt to include in the composition based on the ability of the bile salt to increase the solubility of a fatty acid component when the composition has a pH of 8.5 or less.

According to yet other embodiments of the present invention, a method of providing a pharmaceutical composition includes selecting an amount of a fatty acid to include in the composition based on the ability of the fatty acid to lower the precipitation point of a bile salt component in the composition to a pH of 5.5 or less.

According to other embodiments of the present invention, a method of providing a pharmaceutical composition includes selecting an amount of a fatty acid to include in the composition based on the ability of the fatty acid to alter the precipitation characteristics of a bile salt component in the composition.

DETAILED DESCRIPTION OF THE INVENTION

Figure 1:
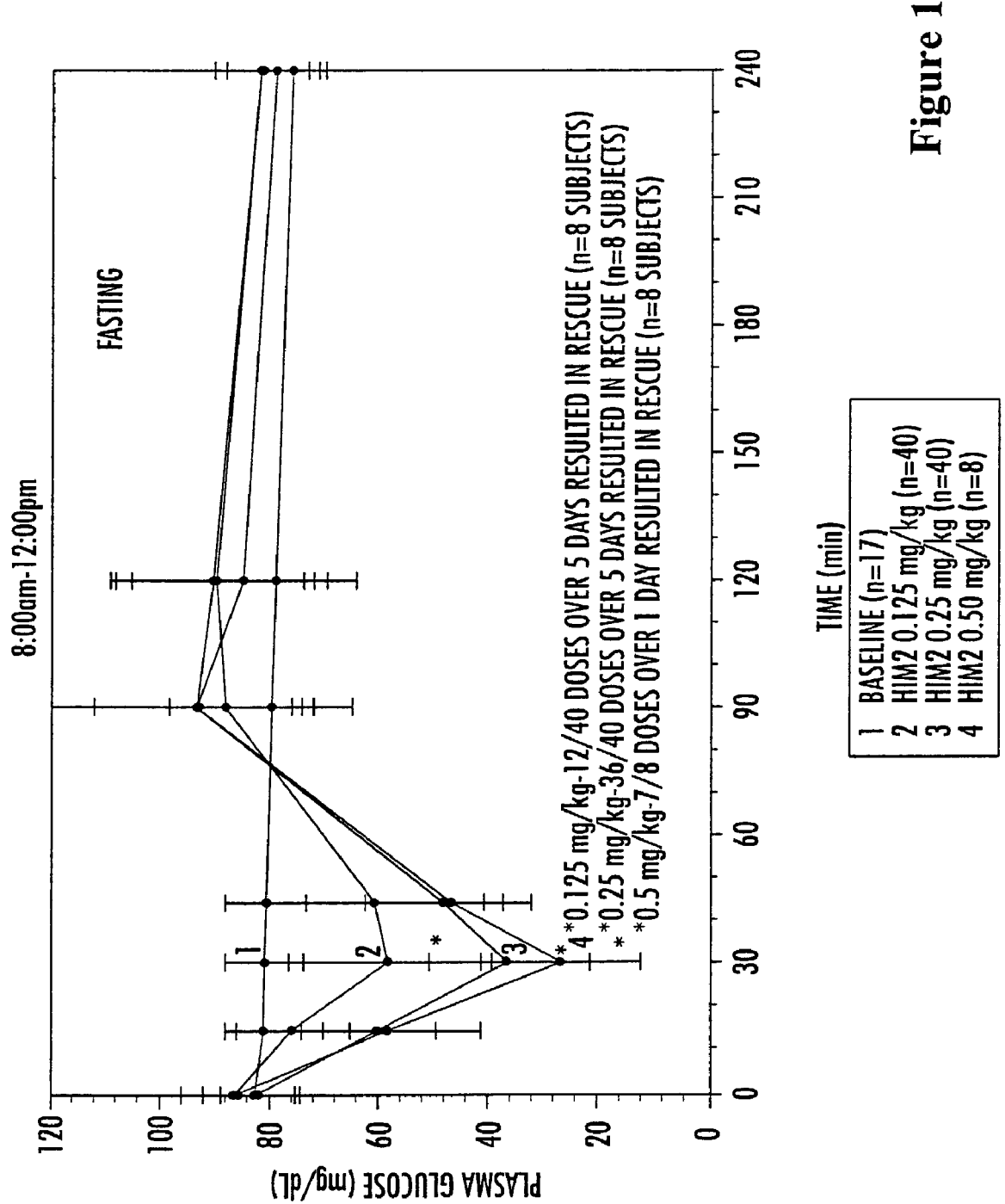
FIG. 1 illustrates a comparison of mean plasma glucose vs. time curves resulting from oral administration of various doses of embodiments of the present invention in fasting, non-diabetic subjects compared with a mean plasma glucose vs. time curve for baseline plasma glucose.

Certain embodiments of the present invention are based on the surprising and unexpected discovery that fatty acids and bile salts in combination have a synergistic effect, which is more than an additive effect on the bioavailability and/or bioefficacy of a drug or drug oligomer-conjugate when administered in combination with the drug or drug oligomer conjugate.

The present invention now will be described more fully hereinafter with reference to the accompanying drawings, in which various embodiments of the invention are shown. This invention can, however, be embodied in many different forms and should not be construed as limited to the embodiments set forth herein; rather, these embodiments are provided so that this disclosure will be thorough and complete, and will fully convey the scope of the invention to those skilled in the art.

All amino acid abbreviations used in this disclosure are those accepted by the United States Patent and Trademark Office as set forth in 37 C.F.R. § 1.822(b).

As used herein, the term "between" when used to describe various ranges should be interpreted to include the endpoints of the described ranges.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "drug" refers to any therapeutic compound that is conjugatable in the manner of the present invention. Representative non-limiting classes of therapeutic compounds useful in the present invention include those falling into the following therapeutic categories: ACE-inhibitors; anti-anginal drugs; anti-arrhythmias; anti-asthmatics; anti-cancer drugs; anti-cholesterolemics; anti-convulsants; anti-depressants; anti-diarrhea preparations; antihistamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mineral supplements; mucolytics; narcotics; neuroleptics; neuromuscular drugs; NSAIDS; nutritional additives; peripheral vasodilators; polypeptides; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents.

The drug can be a peptide or a polypeptide. Non-limiting examples of peptides and/or polypeptides that can be useful in the present invention include the following:

Adrenocorticotropic hormone (ACTH) peptides including, but not limited to, ACTH, human; ACTH 1-10; ACTH 1-13, human; ACTH 1-16, human; ACTH 1-17; ACTH 1-24, human; ACTH 4-10; ACTH 4-11; ACTH 6-24; ACTH 7-38, human; ACTH 18-39, human; ACTH, rat; ACTH 12-39, rat; beta-cell tropin (ACTH 22-39); biotinyl-ACTH 1-24, human; biotinyl-ACTH 7-38, human; corticostatin, human; corticostatin, rabbit; [Met(02)$^4$, DLys$^8$, Phe$^9$] ACTH 4-9, human; [Met(0)$^4$,DLys$^8$, Phe$^9$] ACTH 4-9, human; N-acetyl, ACTH 1-17, human; and ebiratide.

Adrenomedullin peptides including, but not limited to, adrenomedullin, adrenomedullin 1-52, human; adrenomedullin 1-12, human; adrenomedullin 13-52, human; adrenomedullin 22-52, human; pro-adrenomedullin 45-92, human; pro-adrenomedullin 153-185, human; adrenomedullin 1-52, porcine; pro-adrenomedullin (N-20), porcine; adrenomedullin 1-50, rat; adrenomedullin 11-50, rat; and proAM-N20 (proadrenomedullin N-terminal 20 peptide), rat.

Allatostatin peptides including, but not limited to, allatostatin I; allatostatin II; allatostatin III; and allatostatin IV.

Amylin peptides including, but not limited to, acetyl-amylin 8-37, human; acetylated amylin 8-37, rat; AC187 amylin antagonist; AC253 amylin antagonist; AC625 amylin antagonist; amylin 8-37, human; amylin (IAPP), cat; amylin (insulinoma or islet amyloid polypeptide(IAPP)); amylin amide, human; amylin 1-13 (diabetes-associated peptide 1-13), human; amylin 20-29 (IAPP 20-29), human; AC625 amylin antagonist; amylin 8-37, human; amylin (IAPP), cat; amylin, rat; amylin 8-37, rat; biotinyl-amylin, rat; and biotinyl-amylin amide, human.

Amyloid beta-protein fragment peptides including, but not limited to, Alzheimer's disease beta-protein 12-28 (SP17); amyloid beta-protein 25-35; amyloid beta/A4-protein precursor 328-332; amyloid beta/A4 protein precursor (APP) 319-335; amyloid beta-protein 1-43; amyloid beta-protein 1-42; amyloid beta-protein 1-40; amyloid beta-protein 10-20; amyloid beta-protein 22-35; Alzheimer's disease beta-protein (SP28); beta-amyloid peptide 1-42, rat; beta-amyloid peptide 1-40, rat; beta-amyloid 1-11; beta-amyloid 31-35; beta-amyloid 32-35; beta-amyloid 35-25; beta-amyloid/A4 protein precursor 96-110; beta-amyloid precursor protein 657-676; beta-amyloid 1-38; [Gln$^{11}$]-Alzheimer's disease beta-protein; [Gln$^{11}$]-beta-amyloid 1-40; [Gln$^{22}$]-beta-amyloid 6-40; non-A beta component of Alzheimer's disease amyloid (NAC); P3, (A beta 17-40) Alzheimer's disease amyloid β-peptide; and SAP (serum amyloid P component) 194-204.

Angiotensin peptides including, but not limited to, A-779; Ala-Pro-Gly-angiotensin II; [Ile$^3$,Val$^5$]-angiotensin II; angiotensin III antipeptide; angiogenin fragment 108-122; angiogenin fragment 108-123; angiotensin I converting enzyme inhibitor; angiotensin I, human; angiotensin I converting enzyme substrate; angiotensin 11-7, human; angiopeptin; angiotensin II, human; angiotensin II antipeptide; angiotensin II 1-4, human; angiotensin II 3-8, human; angiotensin II 4-8, human; angiotensin II 5-8, human; angiotensin III ([Des-Asp$^1$]-angiotensin II), human; angiotensin III inhibitor ([Ile$^7$]-angiotensin III); angiotensin-converting enzyme inhibitor (*Neothunnus macropterus*); [Asn$^1$, Val$^5$]-angiotensin I, goosefish; [Asn$^1$, Val$^5$, Asn$^9$]-angiotensin I, salmon; [Asn$^1$, Val$^5$, Gly$^9$]-angiotensin I, eel; [Asn$^1$, Val$^5$]-angiotensin I 1-7, eel, goosefish, salmon; [Asn$^1$, Val$^5$]-angiotensin II; biotinyl-angiotensin I, human; biotinyl-angiotensin II, human; biotinyl-Ala-Ala-Ala-angiotensin II; [Des-Asp$^1$]-angiotensin I, human; [p-aminophenylalanine$^6$]-angiotensin II; renin substrate (angiotensinogen 1-13), human; preangiotensinogen 1-14 (renin substrate tetradecapeptide), human; renin substrate tetradecapeptide (angiotensinogen 1-14), porcine; [Sar$^1$]-angiotensin II,

[Sar¹]-angiotensin II 1-7 amide; [Sar¹, Ala⁸]-angiotensin II; [Sar¹, Ile⁸]-angiotensin II; [Sar¹, Thr⁸]-angiotensin II; [Sar¹, Tyr(Me)⁴]-angiotensin II (Sarmesin); [Sar¹, Val⁵, Ala⁸]-angiotensin II; [Sar¹, Ile⁷]-angiotensin III; synthetic tetradecapeptide renin substrate (No. 2); [Val⁴]-angiotensin III; [Val⁵]-angiotensin II; [Val⁵]-angiotensin I, human; [Val⁵]-angiotensin I; [Val⁵, Asn⁹]-angiotensin I, bullfrog; and [Val⁵, Ser⁹]-angiotensin I, fowl.

Antibiotic peptides including, but not limited to, Ac-SQNY (SEQ ID NO: 1); bactenecin, bovine; CAP 37 (20-44); carbormethoxycarbonyl-DPro-DPhe-OBzl; CD36 peptide P 139-155; CD36 peptide P 93-110; cecropin A-melittin hybrid peptide [CA(1-7)M(2-9)NH2]; cecropin B, free acid; CYS(Bzl)84 CD fragment 81-92; defensin (human) HNP-2; dermaseptin; immunostimulating peptide, human; lactoferricin, bovine (BLFC); and magainin spacer.

Antigenic polypeptides, which can elicit an enhanced immune response, enhance an immune response and or cause an immunizingly effective response to diseases and/or disease causing agents including, but not limited to, adenoviruses; anthrax; *Bordetella pertussis; Clostridium botulinum*; bovine rhinotracheitis; *Branhamella catarrhalis*; canine hepatitis; canine distemper; Chlamydiae; cholera; coccidiomycosis; cowpox; cytomegalovirus; Dengue fever; dengue toxoplasmosis; diphtheria; encephalitis; enterotoxigenic *E. coli*; Epstein Barr virus; equine encephalitis; equine infectious anemia; equine influenza; equine pneumonia; equine rhinovirus; *Escherichia coli*; feline leukemia; flavivirus; globulin; haemophilus influenza type b; Haemophilus influenzae; *Haemophilus pertussis; Helicobacter pylori*; hemophilus; hepatitis; hepatitis A; hepatitis B; Hepatitis C; herpes viruses; HIV; HIV-1 viruses; HIV-2 viruses; HTLV; influenza; Japanese encephalitis; *Klebsiella* species; *Legionella pneumophila*; leishmaniosis; leprosy; Lyme disease; malaria immunogen; measles; meningitis; meningococcus; Meningococcal polysaccharide group A; Meningococcal polysaccharide group C; mumps; mumps virus; mycobacteria; *Mycobacterium tuberculosis; Neisseria; Neisseria gonorrhea; Neisseria meningitidis*; ovine blue tongue; ovine encephalitis; papilloma; parainfluenza; paramyxoviruses; pertussis; plague; pneumococcus; *Pneumocystis carinii*; pneumonia; poliovirus; proteus species; *Pseudomonas aeruginosa*; rabies; respiratory syncytial virus; rotavirus; rubella; salmonellae; schistosomiasis; shigellae; simian immunodeficiency virus; smallpox; *Staphylococcus aureus; Staphylococcus* species; *Streptococcus pneumoniae; Streptococcus pyogenes; Streptococcus* species; swine influenza; tetanus; *Treponema pallidum*; typhoid; vaccinia; varicella-zoster virus; and *Vibrio cholerae*.

Anti-microbial peptides including, but not limited to, buforin I; buforin II; cecropin A; cecropin B; cecropin P1, porcine; gaegurin 2 (*Rana rugosa*); gaegurin 5 (*Rana rugosa*); indolicidin; protegrin-(PG)-I; magainin 1; and magainin 2; and T-22 [Tyr⁵,¹², Lys⁷]-poly-phemusin II peptide.

Apoptosis related peptides including, but not limited to, Alzheimer's disease beta-protein (SP28); calpain inhibitor peptide; capsase-1 inhibitor V; capsase-3, substrate IV; caspase-1 inhibitor I, cell-permeable; caspase-1 inhibitor VI; caspase-3 substrate III, fluorogenic; caspase-1 substrate V, fluorogenic; caspase-3 inhibitor I, cell-permeable; caspase-6 ICE inhibitor III; [Des-Ac, biotin]-ICE inhibitor III; IL-1 B converting enzyme (ICE) inhibitor II; IL-1 B converting enzyme (ICE) substrate IV; MDL 28170; and MG-132.

Atrial natriuretic peptides including, but not limited to, alpha-ANP (alpha-chANP), chicken; anantin; ANP 1-11, rat; ANP 8-30, frog; ANP 11-30, frog; ANP-21 (fANP-21), frog; ANP-24 (fANP-24), frog; ANP-30, frog; ANP fragment 5-28, human, canine; ANP-7-23, human; ANP fragment 7-28, human, canine; alpha-atrial natriuretic polypeptide 1-28, human, canine; A71915, rat; atrial natriuretic factor 8-33, rat; atrial natriuretic polypeptide 3-28, human; atrial natriuretic polypeptide 4-28, human, canine; atrial natriuretic polypeptide 5-27; human; atrial natriuretic aeptide (ANP), eel; atriopeptin I, rat, rabbit, mouse; atriopeptin II, rat, rabbit, mouse; atriopeptin III, rat, rabbit, mouse; atrial natriuretic factor (rANF), rat, auriculin A (rat ANF 126-149); auriculin B (rat ANF 126-150); beta-ANP (1-28, dimer, antiparallel); beta-rANF 17-48; biotinyl-alpha-ANP 1-28, human, canine; biotinyl-atrial natriuretic factor (biotinyl-rANF), rat; cardiodilatin 1-16, human; C-ANF 4-23, rat; Des-[Cys¹⁰⁵, Cys¹²¹]-atrial natriuretic factor 104-126, rat; [Met(O)¹²] ANP 1-28, human; [Mpr⁷,DAla⁹]ANP 7-28, amide, rat; prepro-ANF 104-116, human; prepro-ANF 26-55 (proANF 1-30), human; prepro-ANF 56-92 (proANF 31-67), human; prepro-ANF 104-123, human; [Tyr⁰]-atriopeptin I, rat, rabbit, mouse; [Tyr⁰]-atriopeptin II, rat, rabbit, mouse; [Tyr⁰]-prepro ANF 104-123, human; urodilatin (CDD/ANP 95-126); ventricular natriuretic peptide (VNP), eel; and ventricular natriuretic peptide (VNP), rainbow trout.

Bag cell peptides including, but not limited to, alpha bag cell peptide; alpha-bag cell peptide 1-9; alpha-bag cell peptide 1-8; alpha-bag cell peptide 1-7; beta-bag cell factor; and gamma-bag cell factor.

Bombesin peptides including, but not limited to, alpha-s1 casein 101-123 (bovine milk); biotinyl-bombesin; bombesin 8-14; bombesin; [Leu¹³-psi (CH2NH)Leu¹⁴]-bombesin; [D-Phe⁶, Des-Met¹⁴]-bombesin 6-14 ethylamide; [DPhe¹²] bombesin; [DPhe¹²,Leu¹⁴]-bombesin; [Tyr⁴]-bombesin; and [Tyr⁴,DPhe¹²]-bombesin.

Bone GLA peptides (BGP) including, but not limited to, bone GLA protein; bone GLA protein 45-49; [Glu¹⁷, Gla²¹,²⁴]-osteocalcin 1-49, human; myclopeptide-2 (MP-2); osteocalcin 1-49 human; osteocalcin 37-49, human; and [Tyr³⁸, Phe⁴²,⁴⁶] bone GLA protein 38-49, human.

Bradykinin peptides including, but not limited to, [Ala²,⁶, des-Pro³]-bradykinin; bradykinin; bradykinin (Bowfin. Gar); bradykinin potentiating peptide; bradykinin 1-3; bradykinin 1-5; bradykinin 1-6; bradykinin 1-7; bradykinin 2-7; bradykinin 2-9; [DPhe⁷] bradykinin; [Des-Arg⁹]-bradykinin; [Des-Arg¹⁰]-Lys-bradykinin ([Des-Arg¹⁰]-kallidin); [D-N-Me-Phe⁷]-bradykinin; [Des-Arg⁹, Leu⁸]-bradykinin; Lys-bradykinin (kallidin); Lys-[Des-Arg⁹,Leu⁸]-bradykinin ([Des-Arg¹⁰,Leu⁹]-kallidin); [Lys⁰-Hyp³]-bradykinin; ovokinin; [Lys⁰, Ala³]-bradykinin; Met-Lys-bradykinin; peptide K12 bradykinin potentiating peptide; [(pCl)Phe⁵,⁸]-bradykinin; T-kinin (Ile-Ser-bradykinin); [Thi⁵,⁸, D-Phe⁷]-bradykinin; [Tyr⁰]-bradykinin; [Tyr⁵]-bradykinin; [Tyr⁸]-bradykinin; and kallikrein.

Brain natriuretic peptides (BNP) including, but not limited to, BNP 32, canine; BNP-like Peptide, eel; BNP-32, human; BNP-45, mouse; BNP-26, porcine; BNP-32, porcine; biotinyl-BNP-32, porcine; BNP-32, rat; biotinyl-BNP-32, rat; BNP-45 (BNP 51-95, 5K cardiac natriuretic peptide), rat; and [Tyr⁰]-BNP 1-32, human.

C-peptides including, but not limited to, C-peptide; and [Tyr⁰]-C-peptide, human.

C-type natriuretic peptides (CNP) including, but not limited to, C-type natriuretic peptide, chicken; C-type natriuretic peptide-22 (CNP-22), porcine, rat, human; C-type natriuretic peptide-53 (CNP-53), human; C-type natriuretic peptide-53 (CNP-53), porcine, rat; C-type natriuretic peptide-53 (porcine, rat) 1-29 (CNP-53 1-29); prepro-CNP 1-27, rat; prepro-CNP 30-50, porcine, rat; vasonatrin peptide (VNP); and [Tyr⁰]-C-type natriuretic peptide-22 ([Tyr⁰]-CNP-22).

Calcitonin peptides including, but not limited to, biotinyl-calcitonin, human; biotinyl-calcitonin, rat; biotinyl-calcitonin, salmon; calcitonin, chicken; calcitonin, eel; calcitonin, human; calcitonin, porcine; calcitonin, rat; calcitonin, salmon; calcitonin 1-7, human; calcitonin 8-32, salmon; katacalcin (PDN-21) (C-procalcitonin); and N-proCT (amino-terminal procalcitonin cleavage peptide), human.

Calcitonin gene related peptides (CGRP) including, but not limited to, acetyl-alpha-CGRP 19-37, human; alpha-CGRP 19-37, human; alpha-CGRP 23-37, human; biotinyl-CGRP, human; biotinyl-CGRP II, human; biotinyl-CGRP, rat; beta-CGRP, rat; biotinyl-beta-CGRP, rat; CGRP, rat; CGRP, human; calcitonin C-terminal adjacent peptide; CGRP 1-19, human; CGRP 20-37, human; CGRP 8-37, human; CGRP II, human; CGRP, rat; CGRP 8-37, rat; CGRP 29-37, rat; CGRP 30-37, rat; CGRP 31-37, rat; CGRP 32-37, rat; CGRP 33-37, rat; CGRP 31-37, rat; ([Cys(Acm)$^{2,7}$]-CGRP; elcatonin; [Tyr⁰]-CGRP, human; [Tyr⁰]-CGRP II, human; [Tyr⁰]-CGRP 28-37, rat; [Tyr⁰]-CGRP, rat; and [Tyr$^{22}$]-CGRP 22-37, rat.

CART peptides including, but not limited to, CART, human; CART 55-102, human; CART, rat; and CART 55-102, rat.

Casomorphin peptides including, but not limited to, beta-casomorphin, human; beta-casomorphin 1-3; beta-casomorphin 1-3, amide; beta-casomorphin, bovine; beta-casomorphin 1-4, bovine; beta-casomorphin 1-5, bovine; beta-casomorphin 1-5, amide, bovine; beta-casomorphin 1-6, bovine; [DAla²]-beta-casomorphin 1-3, amide, bovine; [DAla²,Hyp⁴,Tyr⁵]-beta-casomorphin 1-5 amide; [DAla², DPro⁴,Tyr⁵]-beta-casomorphin 1-5, amide; [DAla²,Tyr⁵]-beta-casomorphin 1-5, amide, bovine; [DAla$^{2,4}$,Tyr⁵]-beta-casomorphin 1-5, amide, bovine; [DAla², (pCl)Phe³]-beta-casomorphin, amide, bovine; [DAla²]-beta-casomorphin 1-4, amide, bovine; [DAla²]-beta-casomorphin 1-5, bovine; [DAla²]-beta-casomorphin 1-5, amide, bovine; [DAla², Met⁵]-beta-casomorphin 1-5, bovine; [DPro²]-beta-casomorphin 1-5, amide, bovine; [DAla²]-beta-casomorphin 1-6, bovine; [DPro²]-beta-casomorphin 1-4, amide; [Des-Tyr¹]-beta-casomorphin, bovine; [DAla$^{2,4}$,Tyr⁵]-beta-casomorphin 1-5, amide, bovine; [DAla², (pCl)Phe³]-beta-casomorphin, amide, bovine; [DAla²]-beta-casomorphin 1-4, amide, bovine; [DAla²]-beta-casomorphin 1-5, bovine; [DAla²]-beta-casomorphin 1-5, amide, bovine; [DAla²,Met⁵]-beta-casomorphin 1-5, bovine; [DPro²]-beta-casomorphin 1-5, amide, bovine; [DAla²]-beta-casomorphin 1-6, bovine; [DPro²]-beta-casomorphin 1-4, amide; [Des-Tyr¹]-beta-casomorphin, bovine; and [Val³]-beta-casomorphin 1-4, amide, bovine.

Chemotactic peptides including, but not limited to, defensin 1 (human) HNP-1 (human neutrophil peptide-1); and N-formyl-Met-Leu-Phe.

Cholecystokinin (CCK) peptides including, but not limited to, caerulein; cholecystokinin; cholecystokinin-pancreozymin; CCK-33, human; cholecystokinin octapeptide 1-4 (non-sulfated) (CCK 26-29, unsulfated); cholecystokinin octapeptide (CCK 26-33); cholecystokinin octapeptide (non-sulfated) (CCK 26-33, unsulfated); cholecystokinin heptapeptide (CCK 27-33); cholecystokinin tetrapeptide (CCK 30-33); CCK-33, porcine; CR 1 409, cholecystokinin antagonist; CCK flanking peptide (unsulfated); N-acetyl cholecystokinin, CCK 26-30, sulfated; N-acetyl cholecystokinin, CCK 26-31, sulfated; N-acetyl cholecystokinin, CCK 26-31, non-sulfated; prepro CCK fragment V-9-M; and proglumide.

Colony-stimulating factor peptides including, but not limited to, colony-stimulating factor (CSF); GMCSF; MCSF; and G-CSF.

Corticortropin releasing factor (CRF) peptides including, but not limited to, astressin; alpha-helical CRF 12-41; biotinyl-CRF, ovine; biotinyl-CRF, human, rat; CRF, bovine; CRF, human, rat; CRF, ovine; CRF, porcine; [Cys$^{21}$]-CRF, human, rat; CRF antagonist (alpha-helical CRF 9-41); CRF 6-33, human, rat; [DPro⁵]-CRF, human, rat; [D-Phe$^{12}$, Nle$^{21,38}$]-CRF 12-41, human, rat; eosinophilotactic peptide; [Met(0)$^{21}$]-CRF, ovine; [Nle$^{21}$,Tyr$^{32}$]-CRF, ovine; prepro CRF 125-151, human; sauvagine, frog; [Tyr⁰]-CRF, human, rat; [Tyr⁰]-CRF, ovine; [Tyr⁰]-CRF 34-41, ovine; [Tyr⁰]-urocortin; urocortin amide, human; urocortin, rat; urotensin I (Catostomus commersoni); urotensin II; and urotensin II (Rana ridibunda).

Cortistatin peptides including, but not limited to, cortistatin 29; cortistatin 29 (1-13); [Tyr⁰]-cortistatin 29; pro-cortistatin 28-47; and pro-cortistatin 51-81.

Cytokine peptides including, but not limited to, tumor necrosis factor; and tumor necrosis factor-β (TNF-β).

Dermorphin peptides including, but not limited to, dermorphin and dermorphin analog 1-4.

Dynorphin peptides including, but not limited to, big dynorphin (prodynorphin 209-240), porcine; biotinyl-dynorphin A (biotinyl-prodynorphin 209-225); [DAla², DArg⁶]-dynorphin A 1-13, porcine; [D-Ala²]-dynorphin A, porcine; [D-Ala²]-dynorphin A amide, porcine; [D-Ala²]-dynorphin A 1-13, amide, porcine; [D-Ala²]-dynorphin A 1-9, porcine; [DArg⁶]-dynorphin A 1-13, porcine; [DArg⁸]-dynorphin A 1-13, porcine; [Des-Tyr¹]-dynorphin A 1-8; [D-Pro$^{10}$]-dynorphin A 1-11, porcine; dynorphin A amide, porcine; dynorphin A 1-6, porcine; dynorphin A 1-7, porcine; dynorphin A 1-8, porcine; dynorphin A 1-9, porcine; dynorphin A 1-10, porcine; dynorphin A 1-10 amide, porcine; dynorphin A 1-11, porcine; dynorphin A 1-12, porcine; dynorphin A 1-13, porcine; dynorphin A 1-13 amide, porcine; DAKLI (dynorphin A-analogue kappa ligand); DAKLI-biotin ([Arg$^{11,13}$]-dynorphin A (1-13)-Gly-NH(CH2)5NH-biotin); dynorphin A 2-17, porcine; dynorphin 2-17, amide, porcine; dynorphin A 2-12, porcine; dynorphin A 3-17, amide, porcine; dynorphin A 3-8, porcine; dynorphin A 3-13, porcine; dynorphin A 3-17, porcine; dynorphin A 7-17, porcine; dynorphin A 8-17, porcine; dynorphin A 6-17, porcine; dynorphin A 13-17, porcine; dynorphin A (prodynorphin 209-225), porcine; dynorphin B 1-9; [MeTyr¹, MeArg⁷, D-Leu⁸]-dynorphin 1-8 ethyl amide; [(nMe)Tyr¹] dynorphin A 1-13, amide, porcine; [Phe⁷]-dynorphin A 1-7, porcine; [Phe⁷]-dynorphin A 1-7, amide, porcine; and prodynorphin 228-256 (dynorphin B 29) (leumorphin), porcine.

Endorphin peptides including, but not limited to, alpha-neo-endorphin, porcine; beta-neo-endorphin; Ac-beta-endorphin, camel, bovine, ovine; Ac-beta-endorphin 1-27, camel, bovine, ovine; Ac-beta-endorphin, human; Ac-beta-endorphin 1-26, human; Ac-beta-endorphin 1-27, human; Ac-gamma-endorphin (Ac-beta-lipotropin 61-77); acetyl-alpha-endorphin; alpha-endorphin (beta-lipotropin 61-76); alpha-neo-endorphin analog; alpha-neo-endorphin 1-7; [Arg⁸]-alpha-neo-endorphin 1-8; beta-endorphin (beta-lipotropin 61-91), camel, bovine, ovine; beta-endorphin 1-27, camel, bovine, ovine; beta-endorphin, equine; beta-endorphin (beta-lipotropin 61-91), human; beta-endorphin (1-5)+(16-31), human; beta-endorphin 1-26, human; beta-endorphin 1-27, human; beta-endorphin 6-31, human; beta-endorphin 18-31, human; beta-endorphin, porcine; beta-endorphin, rat; beta-lipotropin 1-10, porcine; beta-lipotropin 60-65; beta-lipotropin 61-64; beta-lipotropin 61-69; beta-lipotropin 88-91; biotinyl-beta-endorphin (biotinyl-beta-lipotropin 61-91); biocytin-beta-endorphin, human; gamma-endorphin (beta-lipotropin 61-77); [DAla$^2$]-alpha-neo-endorphin 1-2, amide; [DAla$^2$]-beta-lipotropin 61-69; [DAla$^2$]-gamma-endorphin; [Des-Tyr$^1$]-beta-endorphin, human; [Des-Tyr$^1$]-gamma-endorphin (beta-lipotropin 62-77); [Leu$^5$]-beta-endorphin, camel, bovine, ovine; [Met$^5$, Lys$^6$]-alpha-neo-endorphin 1-6; [Met$^5$, Lys$^{6,7}$]-alpha-neo-endorphin 1-7; and [Met$^5$, Lys$^6$, Arg$^7$]-alpha-neo-endorphin 1-7.

Endothelin peptides including, but not limited to, endothelin-1 (ET-1); endothelin-1[Biotin-Lys$^9$]; endothelin-1 (1-15), human; endothelin-1 (1-15), amide, human; Ac-endothelin-1(16-21), human; Ac-[DTrp$^{16}$]-endothelin-1 (16-21), human; [Ala$^{3,11}$]-endothelin-1; [Dprl, Asp$^{15}$]-endothelin-1; [Ala$^2$]-endothelin-3, human; [Ala$^{18}$]-endothelin-1, human; [Asn$^{18}$]-endothelin-1, human; [Res-701-1]-endothelin B receptor antagonist; Suc-[Glu$^9$, Ala$^{11,15}$]-endothelin-1 (8-21), IRL-1620; endothelin-C-terminal hexapeptide; [D-Val$^{22}$]-big endothelin-1 (16-38), human; endothelin-2 (ET-2), human, canine; endothelin-3 (ET-3), human, rat, porcine, rabbit; biotinyl-endothelin-3 (biotinyl-ET-3); pre-pro-endothelin-1 (94-109), porcine; BQ-518; BQ-610; BQ-788; endothelium-dependent relaxation antagonist; FR139317; IRL-1038; JKC-30 1; JKC-302; PD-145065; PD 142893; sarafotoxin S6a (*atractaspis engaddensis*); sarafotoxin S6b (*atractaspis engaddensis*); sarafotoxin S6c (*atractaspis engaddensis*); [Lys$^4$]-sarafotoxin S6c; sarafotoxin S6d; big endothelin-1, human; biotinyl-big endothelin-1, human; big endothelin-1 (1-39), porcine; big endothelin-3 (22-41), amide, human; big endothelin-1 (22-39), rat; big endothelin-1 (1-39), bovine; big endothelin-1 (22-39), bovine; big endothelin-1 (19-38), human; big endothelin-1 (22-38), human; big endothelin-2, human; big endothelin-2 (22-37), human; big endothelin-3, human; big endothelin-1, porcine; big endothelin-1 (22-39) (prepro-endothelin-1 (74-91)); big endothelin-1, rat; big endothelin-2 (1-38), human; big endothelin-2 (22-38), human; big endothelin-3, rat; biotinyl-big endothelin-1, human; and [Tyr$^{123}$]-prepro-endothelin (110-130), amide, human.

ETa receptor antagonist peptides including, but not limited to, [BQ-123]; [BE18257B]; [BE-18257A]/[W-7338A]; [BQ-485]; FR139317; PD-151242; and TTA-386.

ETb receptor antagonist peptides including, but not limited to, [BQ-3020]; [RES-701-3]; and [IRL-1720]

Enkephalin peptides including, but not limited to, adrenorphin, free acid; amidorphin (proenkephalin A (104-129)-NH2), bovine; BAM-12P (bovine adrenal medulla dodecapeptide); BAM-22P (bovine adrenal medulla docosapeptide); benzoyl-Phe-Ala-Arg; enkephalin; [D-Ala$^2$, D-Leu$^5$]-enkephalin; [D-Ala$^2$, D-Met$^5$]-enkephalin; [DAla$^2$]-Leu-enkephalin, amide; [DAla$^2$,Leu$^5$,Arg$^6$]-enkephalin; [Des-Tyr$^1$,DPen$^{2,5}$]-enkephalin; [Des-Tyr$^1$,DPen$^2$, Pen$^5$]-enkephalin; [Des-Tyr$^1$]-Leu-enkephalin; [D-Pen$^{2,5}$]-enkephalin; [DPen$^2$, Pen$^5$]-enkephalin; enkephalinase substrate; [D-Pen$^2$, pCI-Phe$^4$, D-Pen$^5$]-enkephalin; Leu-enkephalin; Leu-enkephalin, amide; biotinyl-Leu-enkephalin; [D-Ala$^2$]-Leu-enkephalin; [D-Ser$^2$]-Leu-enkephalin-Thr (delta-receptor peptide) (DSLET); [D-Thr$^2$]-Leu-enkephalin-Thr (DTLET); [Lys$^6$]-Leu-enkephalin; [Met$^5$,Arg$^6$]-enkephalin; [Met$^5$,Arg$^6$]-enkephalin-Arg; [Met$^5$,Arg$^6$,Phe$^7$]-enkephalin; Met-enkephalin; biotinyl-Met-enkephalin; [D-Ala$^2$]-Met-enkephalin; [D-Ala$^2$]-Met-enkephalin, amide; Met-enkephalin-Arg-Phe; Met-enkephalin, amide; [Ala$^2$]-Met-enkephalin, amide; [DMet$^2$, Pro$^5$]-enkephalin, amide; [DTrp$^2$]-Met-enkephalin, amide, metorphinamide (adrenorphin); peptide B, bovine; 3200-Dalton adrenal peptide E, bovine; peptide F, bovine; preproenkephalin B 186-204, human; spinorphin, bovine; and thiorphan (D, L, 3-mercapto-2-benzylpropanoyl-glycine).

Fibronectin peptides including, but not limited to platelet factor-4 (58-70), human; echistatin (*Echis carinatus*); E, P ,L selectin conserved region; fibronectin analog; fibronectin-binding protein; fibrinopeptide A, human; [Tyr$^0$]-fibrinopeptide A, human; fibrinopeptide B, human; [Glu$^1$]-fibrinopeptide B, human; [Tyr$^{15}$]-fibrinopeptide B, human; fibrinogen beta-chain fragment of 24-42; fibrinogen binding inhibitor peptide; fibronectin related peptide (collagen binding fragment); fibrinolysis inhibiting factor; FN-C/H-1 (fibronectin heparin-binding fragment); FN-C/H-V (fibronectin heparin-binding fragment); heparin-binding peptide; laminin penta peptide, amide; Leu-Asp-Val-NH2 (LDV-NH2), human, bovine, rat, chicken; necrofibrin, human; necrofibrin, rat; and platelet membrane glycoprotein IIB peptide 296-306.

Galanin peptides including, but not limited to, galanin, human; galanin 1-19, human; preprogalanin 1-30, human; preprogalanin 65-88, human; preprogalanin 89-123, human; galanin, porcine; galanin 1-16, porcine, rat; galanin, rat; biotinyl-galanin, rat; preprogalanin 28-67, rat; galanin 1-13-bradykinin 2-9, amide; M40, galanin 1-13-Pro-Pro-(Ala-Leu) 2-Ala-amide; C7, galanin 1-13-spantide-amide; GMAP 1-41, amide; GMAP 16-41, amide; GMAP 25-41, amide; galantide; and entero-kassinin.

Gastrin peptides including, but not limited to, gastrin, chicken; gastric inhibitory peptide (GIP), human; gastrin I, human; biotinyl-gastrin I, human; big gastrin-1, human; gastrin releasing peptide, human; gastrin releasing peptide 1-16, human; gastric inhibitory polypeptide (GIP), porcine; gastrin releasing peptide, porcine; biotinyl-gastrin releasing peptide, porcine; gastrin releasing peptide 14-27, porcine, human; little gastrin, rat; pentagastrin; gastric inhibitory peptide 1-30, porcine; gastric inhibitory peptide 1-30, amide, porcine; [Tyr$^0$]-gastric inhibitory peptide 23-42, human; and gastric inhibitory peptide, rat.

Glucagon peptides including, but not limited to, [Des-His$^1$,Glu$^9$]-glucagon, extendin-4, glucagon, human; biotinyl-glucagon, human; glucagon 19-29, human; glucagon 22-29, human; Des-His$^1$-[Glu$^9$]-glucagon, amide; glucagon-like peptide 1, amide (preproglucagon 72-107, amide); glucagon-like peptide 1 (preproglucagon 72-108), human; glucagon-like peptide 1 (7-36) (preproglucagon 78-107, amide); glucagon-like peptide II, rat; biotinyl-glucagon-like peptide-1 (7-36) (biotinyl-preproglucagon 78-107, amide); glucagon-like peptide 2 (preproglucagon 126-159), human; oxyntomodulin/glucagon 37; and valosin (peptide VQY), porcine.

Gn-RH associated peptides (GAP) including, but not limited to, Gn-RH associated peptide 25-53, human; Gn-RH associated peptide 1-24, human; Gn-RH associated peptide 1-13, human; Gn-RH associated peptide 1-13, rat; gonadotropin releasing peptide, follicular, human; [Tyr$^0$]-GAP ([Tyr$^0$]-Gn-RH Precursor Peptide 14-69), human; and proopiomelanocortin (POMC) precursor 27-52, porcine.

Growth factor peptides including, but not limited to, cell growth factors; epidermal growth factors; tumor growth factor; alpha-TGF; beta-TF; alpha-TGF 34-43, rat; EGF, human; acidic fibroblast growth factor; basic fibroblast growth factor; basic fibroblast growth factor 13-18; basic fibroblast growth factor 120-125; brain derived acidic fibroblast growth factor 1-11; brain derived basic fibroblast growth factor 1-24; brain derived acidic fibroblast growth factor 102-111; [Cys(Acm$^{20,31}$)]-epidermal growth factor 20-31; epidermal growth factor receptor peptide 985-996; insulin-like growth factor (IGF)-I, chicken; IGF-I, rat; IGF-I, human; Des (1-3) IGF-I, human; R3 IGF-I, human; R3 IGF-I, human; long R3 IGF-I, human; adjuvant peptide analog; anorexigenic peptide; Des (1-6) IGF-II, human; R6 IGF-II, human; IGF-I analogue; IGF I (24-41); IGF I (57-70); IGF I (30-41); IGF II; IGF II (33-40); [Tyr$^0$]-IGF II (33-40); liver cell growth factor; midkine; midkine 60-121, human; N-acetyl, alpha-TGF 34-43, methyl ester, rat; nerve growth factor (NGF), mouse; platelet-derived growth factor; platelet-derived growth factor antagonist; transforming growth factor-alpha, human; and transforming growth factor-I, rat.

Growth hormone peptides including, but not limited to, growth hormone (hGH), human; growth hormone 1-43, human; growth hormone 6-13, human; growth hormone releasing factor, human; growth hormone releasing factor, bovine; growth hormone releasing factor, porcine; growth hormone releasing factor 1-29, amide, rat; growth hormone pro-releasing factor, human; biotinyl-growth hormone releasing factor, human; growth hormone releasing factor 1-29, amide, human; [D-Ala$^2$]-growth hormone releasing factor 1-29, amide, human; [N-Ac-Tyr$^1$, D-Arg$^2$]-GRF 1-29, amide; [His$^1$, Nle$^{27}$]-growth hormone releasing factor 1-32, amide; growth hormone releasing factor 1-37, human; growth hormone releasing factor 1-40, human; growth hormone releasing factor 1-40, amide, human; growth hormone releasing factor 30-44, amide, human; growth hormone releasing factor, mouse; growth hormone releasing factor, ovine; growth hormone releasing factor, rat; biotinyl-growth hormone releasing factor, rat; GHRP-6 ([His$^1$, Lys$^6$]-GHRP); hexarelin (growth hormone releasing hexapeptide); and [D-Lys$^3$]-GHRP-6.

GTP-binding protein fragment peptides including, but not limited to, [Arg$^8$]-GTP-binding protein fragment, Gs alpha; GTP-binding protein fragment, G beta; GTP-binding protein fragment, GAlpha; GTP-binding protein fragment, Go Alpha; GTP-binding protein fragment, Gs Alpha; and GTP-binding protein fragment, G Alpha i2.

Guanylin peptides including, but not limited to, guanylin, human; guanylin, rat; and uroguanylin.

Inhibin peptides including, but not limited to, inhibin, bovine; inhibin, alpha-subunit 1-32, human; [Tyr$^0$]-inhibin, alpha-subunit 1-32, human; seminal plasma inhibin-like peptide, human; [Tyr$^0$]-seminal plasma inhibin-like peptide, human; inhibin, alpha-subunit 1-32, porcine; and [Tyr$^0$]-inhibin, alpha-subunit 1-32, porcine.

Insulin peptides including, but not limited to, insulin, human; insulin, porcine; IGF-I, human; insulin-like growth factor II (69-84); pro-insulin-like growth factor II (68-102), human; pro-insulin-like growth factor II (105-128), human; [Asp$^{B28}$]-insulin, human; [Lys$^{B28}$]-insulin, human; [Leu$^{B28}$]-insulin, human; [Val$^{B28}$]-insulin, human; [Ala$^{B28}$]-insulin, human; [ASP$^{B28}$, Pro$^{B29}$]-insulin, human; [Lys$^{B28}$, Pro$^{B29}$]-insulin, human; [Leu$^{B28}$, Pro$^{B29}$]-insulin, human; [Val$^{B28}$, Pro$^{B29}$-insulin, human; [Ala$^{B28}$, Pro$^{B29}$]-insulin, human; [Gly$^{A21}$]-insulin, human; [Gly$^{A21}$ Gln$^{B3}$]-insulin, human; [Ala$^{A21}$]-insulin, human; [Ala$^{A21}$ Gln$^{B3}$]-insulin, human; [Gln$^{B3}$]-insulin, human; [Gln$^{B30}$]-insulin, human; [Gly$^{A21}$ Glu$^{B30}$]-insulin, human; [Gly$^{A21}$ Gln$^{B3}$ Glu$^{B30}$]-insulin, human; [Gln$^{B3}$ Glu$^{B30}$]-insulin, human; B22-B30 insulin, human; B23-B30 insulin, human; B25-B30 insulin, human; B26-B30 insulin, human; B27-B30 insulin, human; B29-B30 insulin, human; the A chain of human insulin, and the B chain of human insulin.

Interleukin peptides including, but not limited to, interleukin-1 beta 165-181, rat; and interleukin-8 (IL-8, CINC/gro), rat.

Laminin peptides including, but not limited to, laminin; alpha1 (I)-CB3 435-438, rat; and laminin binding inhibitor.

Leptin peptides including, but not limited to, leptin 93-105, human; leptin 22-56, rat; Tyr-leptin 26-39, human; and leptin 116-130, amide, mouse.

Leucokinin peptides including, but not limited to, leucomyosuppressin (LMS); leucopyrokinin (LPK); leucokinin I; leucokinin II; leucokinin III; leucokinin IV; leucokinin VI; leucokinin VII; and leucokinin VIII.

Luteinizing hormone-releasing hormone peptides including, but not limited to, antide; Gn-RH II, chicken; luteinizing hormone-releasing hormone (LH-RH) (GnRH); biotinyl-LH-RH; cetrorelix (D-20761); [D-Ala$^6$]-LH-RH; [Gln$^8$]-LH-RH (Chicken LH-RH); [DLeu$^6$, Val$^7$] LH-RH 1-9, ethyl amide; [D-Lys$^6$]-LH-RH; [D-Phe$^2$, Pro$^3$, D-Phe$^6$]-LH-RH; [DPhe$^2$, DAla$^6$] LH-RH; [Des-Gly$^{10}$]-LH-RH, ethyl amide; [D-Ala$^6$, Des-Gly$^{10}$]-LH-RH, ethyl amide; [DTrp$^6$]-LH-RH, ethyl amide; [D-Trp$^6$, Des-Gly$^{10}$]-LH-RH, ethyl amide (Deslorelin); [DSer(But)$^6$, Des-Gly$^{10}$]-LH-RH, ethyl amide; ethyl amide; leuprolide; LH-RH 4-10; LH-RH 7-10; LH-RH, free acid; LH-RH, lamprey; LH-RH, salmon; [Lys$^8$]-LH-RH; [Trp$^7$,Leu$^8$] LH-RH, free acid; and [(t-Bu)DSer$^6$, (Aza)Gly$^{10}$]-LH-RH.

Mastoparan peptides including, but not limited to, mastoparan; mas7; mas8; mas 17; and mastoparan X.

Mast cell degranulating peptides including, but not limited to, mast cell degranulating peptide HR-1; and mast cell degranulating peptide HR-2.

Melanocyte stimulating hormone (MSH) peptides including, but not limited to, [Ac-Cys$^4$,DPhe$^7$,Cys$^{10}$] alpha-MSH 4-13, amide; alpha-melanocyte stimulating hormone; alpha-MSH, free acid; beta-MSH, porcine; biotinyl-alpha-melanocyte stimulating hormone; biotinyl-[Nle$^4$, D-Phe$^7$] alpha-melanocyte stimulating hormone; [Des-Acetyl]-alpha-MSH; [DPhe$^7$]-alpha-MSH, amide; gamma-1-MSH, amide; [Lys$^0$]-gamma-1-MSH, amide; MSH release inhibiting factor, amide; [Nle$^4$]-alpha-MSH, amide; [Nle$^4$, D-Phe$^7$]-alpha-MSH; N-Acetyl, [Nle$^4$,DPhe$^7$] alpha-MSH 4-10, amide; beta-MSH, human; and gamma-MSH.

Morphiceptin peptides including, but not limited to, morphiceptin (beta-casomorphin 1-4 amide); [D-Pro$^4$]-morphiceptin; and [N-MePhe$^3$,D-Pro$^4$]-morphiceptin.

Motilin peptides including, but not limited to, motilin, canine; motilin, porcine; biotinyl-motilin, porcine; and [Leu$^{13}$]-motilin, porcine.

Neuro-peptides including, but not limited to, Ac-Asp-Glu; achatina cardio-excitatory peptide-1(ACEP-1) (*Achatina fulica*); adipokinetic hormone (AKH) (Locust); adipokinetic hormone (*Heliothis zea* and *Manduca sexta*); alytesin; *Tabanus atratus* adipokinetic hormone (Taa-AKH); adipokinetic hormone II (*Locusta migratoria*); adipokinetic hormone II (*Schistocera gregaria*); adipokinetic hormone III (AKH-3); adipokinetic hormone G (AKH-G) (*Gryllus bimaculatus*); allatotropin (AT) (*Manduca sexta*); allatotropin 6-13 (*Manduca sexta*); APGW amide (SEQ ID NO: 2) (*Lymnaea stagnalis*); buccalin; cerebellin; [Des-Ser$^1$]-cerebellin; corazonin (American Cockroach *Periplaneta americana*); crustacean cardioactive peptide (CCAP); crustacean erythrophore; DF2 (*Procambarus clarkii*); diazepam-binding inhibitor fragment, human; diazepam binding inhibitor fragment (ODN); eledoisin related peptide; FMRF amide (molluscan cardioexcitatory neuro-peptide); Gly-Pro-Glu (GPE), human; granuliberin R; head activator neuropeptide; [His$^7$]-corazonin; stick insect hypertrehalosaemic factor II;

Tabanus atratus hypotrehalosemic hormone (Taa-HoTH); isoguvacine hydrochloride; bicuculline methiodide; piperidine-4-sulphonic acid; joining peptide of proopiomelanocortin (POMG), bovine; joining peptide, rat; KSAYMRF amide (SEQ ID NO: 3) (*P. redivivus*); kassinin; kinetensin; levitide; litorin; LUQ 81-91 (*Aplysia californica*); LUQ 83-91 (*Aplysia califomica*); myoactive peptide I (Periplanetin CC-1) (Neuro-hormone D); myoactive peptide II (Periplanetin CC-2); myomodulin; neuron specific peptide; neuron specific enolase 404-443, rat; neuropeptide FF; neuropeptide K, porcine; NEI (prepro-MCH 131-143) neuropeptide, rat; NGE (prepro-MCH 110-128) neuropeptide, rat; NF1 (*Procambarus clarkii*); PBAN-1 (*Bombyx mori*); Hez-PBAN (*Heliothis zea*); SCPB (cardioactive peptide from aplysia); secretoneurin, rat; uperolein; urechistachykinin I; urechistachykinin II; xenopsin-related peptide I; xenopsin-related peptide II; pedal peptide (Pep), aplysia; peptide F1, lobster; phyllomedusin; polistes mastoparan; proctolin; ranatensin; Ro I (Lubber Grasshopper, *Romalea microptera*); Ro II (Lubber Grasshopper, *Romalea microptera*); SALMF amide 1 (SEQ ID NO: 4) (S1); SALMF amide 2 (SEQ ID NO: 4) (S2); and SCPA.

Neuropeptide Y (NPY) peptides including, but not limited to, [Leu$^{31}$,Pro$^{34}$]-neuropeptide Y, human; neuropeptide F (*Moniezia expansa*); B1BP3226 NPY antagonist; Bis(31/31') {[Cys$^{31}$, Trp$^{32}$, Nva$^{34}$] NPY 31-36}; neuropeptide Y, human, rat; neuropeptide Y 1-24 amide, human; biotinyl-neuropeptide Y; [D-Tyr$^{27,36}$, D-Thr$^{32}$]-NPY 27-36; Des 10-17 (cyclo 7-21) [Cys$^{7,21}$, Pro$^{34}$]-NPY; C2-NPY; [Leu$^{31}$, Pro$^{34}$] neuropeptide Y, human; neuropeptide Y, free acid, human; neuropeptide Y, free acid, porcine; prepro NPY 68-97, human; N-acetyl-[Leu$^{28}$, Leu$^{31}$] NPY 24-36; neuropeptide Y, porcine; [D-Trp$^{32}$]-neuropeptide Y, porcine; [D-Trp$^{32}$] NPY 1-36, human; [Leu$^{17}$,DTrp$^{32}$] neuropeptide Y, human; [Leu$^{31}$, Pro$^{34}$]-NPY, porcine; NPY 2-36, porcine; NPY 3-36, human; NPY 3-36, porcine; NPY 13-36, human; NPY 13-36, porcine; NPY 16-36, porcine; NPY 18-36, porcine; NPY 20-36; NFY 22-36; NPY 26-36; [Pro$^{34}$]-NPY 1-36, human; [Pro$^{34}$]-neuropeptide Y, porcine; PYX-1; PYX-2; T4-[NPY(33-36)]4; and Tyr(OMe)$^{21}$]-neuropeptide Y, human.

Neurotropic factor peptides including, but not limited to, glial derived neurotropic factor (GDNF); brain derived neurotropic factor (BDNF); and ciliary neurotropic factor (CNTF).

Orexin peptides including, but not limited to, orexin A; orexin B, human; orexin B, rat, mouse.

Opioid peptides including, but not limited to, alpha-casein fragment 90-95; BAM-18P; casomokinin L; casoxin D; crystalline; DALDA; dermenkephalin (deltorphin) (*Phylomedusa sauvagei*); [D-Ala$^2$]-deltorphin I; [D-Ala$^2$]-deltorphin II; endomorphin-1; endomorphin-2; kyotorphin; [DArg$^2$]-kyotorphin; morphin tolerance peptide; morphine modulating peptide, C-terminal fragment; morphine modulating neuropeptide (A-18-F-NH2); nociceptin [orphanin FQ] (ORL1 agonist); TIPP; Tyr-MIF-1; Tyr-W-MIF-1; valorphin; LW-hemorphin-6, human; Leu-valorphin-Arg; and Z-Pro-D-Leu.

Oxytocin peptides including, but not limited to, [Asu$^6$]-oxytocin; oxytocin; biotinyl-oxytocin; [Thr$^4$, Gly$^7$]-oxytocin; and tocinoic acid ([Ile$^3$]-pressinoic acid).

PACAP (pituitary adenylating cyclase activating peptide) peptides including, but not limited to, PACAP 1-27, human, ovine, rat; PACAP (1-27)-Gly-Lys-Arg-NH2, human; [Des-Gln$^{16}$]-PACAP 6-27, human, ovine, rat; PACAP38, frog; PACAP27-NH2, human, ovine, rat; biotinyl-PACAP27-NH2, human, ovine, rat; PACAP 6-27, human, ovine, rat; PACAP38, human, ovine, rat; biotinyl-PACAP38, human, ovine, rat; PACAP 6-38, human, ovine, rat; PACAP27-NH2, human, ovine, rat; biotinyl-PACAP27-NH2, human, ovine, rat; PACAP 6- 27, human, ovine, rat; PACAP38, human, ovine, rat; biotinyl-PACAP38, human, ovine, rat; PACAP 6-38, human, ovine, rat; PACAP38 16-38, human, ovine, rat; PACAP38 31-38, human, ovine, rat; PACAP38 31-38, human, ovine, rat; PACAP-related peptide (PRP), human; and PACAP-related peptide (PRP), rat.

Pancreastatin peptides including, but not limited to, chromostatin, bovine; pancreastatin (hPST-52) (chromogranin A 250-301, amide); pancreastatin 24-52 (hPST-29), human; chromogranin A 286-301, amide, human; pancreastatin, porcine; biotinyl-pancreastatin, porcine; [Nle$^8$]-pancreastatin, porcine; [Tyr$^0$,Nle$^8$]-pancreastatin, porcine; [Tyr$^0$]-pancreastatin, porcine; parastatin 1-19 (chromogranin A 347-365), porcine; pancreastatin (chromogranin A 264-314-amide, rat; biotinyl-pancreastatin (biotinyl-chromogranin A 264-314-amide; [Tyr$^0$]-pancreastatin, rat; pancreastatin 26-51, rat; and pancreastatin 33-49, porcine.

Pancreatic polypeptides including, but not limited to, pancreatic polypeptide, avian; pancreatic polypeptide, human; C-fragment pancreatic polypeptide acid, human; C-fragment pancreatic polypeptide amide, human; pancreatic polypeptide (*Rana temporaria*); pancreatic polypeptide, rat; and pancreatic polypeptide, salmon.

Parathyroid hormone peptides including, but not limited to, [Asp$^{76}$]-parathyroid hormone 39-84, human; [Asp $^{76}$]-parathyroid hormone 53-84, human; [Asn $^{76}$]-parathyroid hormone 1-84, hormone; [Asn$^{76}$]-parathyroid hormone 64-84, human; [Asn$^8$, Leu$^{18}$]-parathyroid hormone 1-34, human; [Cys$^{5,28}$]-parathyroid hormone 1-34, human; hypercalcemia malignancy factor 1-40; [Leu$^{18}$]-parathyroid hormone 1-34, human; [Lys(biotinyl)$^{13}$, Nle$^{8,18}$, Tyr$^{34}$]-parathyroid hormone 1-34 amide; [Nle$^{8,18}$, Tyr$^{34}$]-parathyroid hormone 1-34 amide; [Nle$^{8,18}$, Tyr$^{34}$]-parathyroid hormone 3-34 amide, bovine; [Nle$^{8,18}$, Tyr$^{34}$]-parathyroid hormone 1-34, human; [Nle$^{8,18}$, Tyr$^{34}$]-parathyroid hormone 1-34 amide, human; [Nle$^{8,18}$, Tyr$^{34}$]-parathyroid hormone 3-34 amide, human; [Nle$^{8,18}$, Tyr$^{34}$]-parathyroid hormone 7-34 amide, bovine; [Nle$^{8,21}$, Tyr$^{34}$]-parathyroid hormone 1-34 amide, rat; parathyroid hormone 44-68, human; parathyroid hormone 1-34, bovine; parathyroid hormone 3-34, bovine; parathyroid hormone 1-31 amide, human; parathyroid hormone 1-34, human; parathyroid hormone 13-34, human; parathyroid hormone 1-34, rat; parathyroid hormone 1-38, human; parathyroid hormone 1-44, human; parathyroid hormone 28-48, human; parathyroid hormone 39-68, human; parathyroid hormone 39-84, human; parathyroid hormone 53-84, human; parathyroid hormone 69-84, human; parathyroid hormone 70-84, human; [Pro$^{34}$]-peptide YY (PYY), human; [Tyr$^0$]-hypercalcemia malignancy factor 1-40; [Tyr$^0$]-parathyroid hormone 1-44, human; [Tyr$^0$]-parathyroid hormone 1-34, human; [Tyr$^1$ ]-parathyroid hormone 1-34, human; [Tyr$^{27}$]-parathyroid hormone 27-48, human; [Tyr$^{34}$]-parathyroid hormone 7-34 amide, bovine; [Tyr$^{43}$]-parathyroid hormone 43-68, human; [Tyr$^{52}$, Asn$^{76}$]-parathyroid hormone 52-84, human; and [Tyr$^{63}$]-parathyroid hormone 63-84, human.

Parathyroid hormone (PTH)-related peptides including, but not limited to, PTHrP ([Tyr$^{36}$]-PTHrP 1-36 amide), chicken; hHCF-(1-34)-NH2 (humoral hypercalcemic factor), human; PTH-related protein 1-34, human; biotinyl-PTH-related protein 1-34, human; [Tyr$^0$]-PTH-related protein 1-34, human; [Tyr$^{34}$]-PTH-related protein 1-34 amide, human; PTH-related protein 1-37, human; PTH-related protein 7-34 amide, human; PTH-related protein 38-64 amide, human; PTH-related protein 67-86 amide, human; PTH-related protein 107-111, human, rat, mouse; PTH-related protein 107-111 free acid; PTH-related protein 107-138, human; and PTH-related protein 109-111, human.

Peptide T peptides including, but not limited to, peptide T; [D-Ala¹]-peptide T; and [D-Ala¹]-peptide T amide.

Prolactin-releasing peptides including, but not limited to, prolactin-releasing peptide 31, human; prolactin-releasing peptide 20, human; prolactin-releasing peptide 31, rat; prolactin-releasing peptide 20, rat; prolactin-releasing peptide 31, bovine; and prolactin-releasing peptide 20, bovine.

Peptide YY (PYY) peptides including, but not limited to, PYY, human; PYY 3-36, human; biotinyl-PYY, human; PYY, porcine, rat; and [Leu³¹, Pro³⁴]-PYY, human.

Renin substrate peptides including, but not limited to, acetyl, angiotensinogen 1-14, human; angiotensinogen 1-14, porcine; renin substrate tetradecapeptide, rat; [Cys⁸]-renin substrate tetradecapeptide, rat; [Leu⁸]-renin substrate tetradecapeptide, rat; and [Val⁸]-renin substrate tetradecapeptide, rat.

Secretin peptides including, but not limited to, secretin, canine; secretin, chicken; secretin, human; biotinyl-secretin, human; secretin, porcine; and secretin, rat.

Somatostatin (GIF) peptides including, but not limited to, BIM-23027; biotinyl-somatostatin; biotinylated cortistatin 17, human; cortistatin 14, rat; cortistatin 17, human; [Tyr⁰]-cortistatin 17, human; cortistatin 29, rat; [D-Trp⁸]-somatostatin; [DTrp⁸,DCys¹⁴]-somatostatin; [DTrp⁸,Tyr¹¹]-somatostatin; [D-Trp¹¹]-somatostatin; NTB (Naltriben); [Nle⁸]-somatostatin 1-28; octreotide (SMS 201-995); prosomatostatin 1-32, porcine; [Tyr⁰]-somatostatin; [Tyr¹]-somatostatin; [Tyr¹]-somatostatin 28 (1-14); [Tyr¹¹]-somatostatin; [Tyr⁰, D-Trp⁸]-somatostatin; somatostatin; somatostatin antagonist; somatostatin-25; somatostatin-28; somatostatin 28 (1-12); biotinyl-somatostatin-28; [Tyr⁰]-somatostatin-28; [Leu⁸, D-Trp²², Tyr²⁵]-somatostatin-28; biotinyl-[Leu⁸, D-Trp²², Tyr²⁵]-somatostatin-28; somatostatin-28 14); and somatostatin analog, RC-160.

Substance P peptides including, but not limited to, G protein antagonist-2; Ac-[Arg⁶, Sar⁹, Met(02)¹¹]-substance P 6-11; [Arg³]-substance P; Ac-Trp-3,5-bis(trifluoromethyl) benzyl ester; Ac-[Arg⁶, Sar⁹, Met(O2)¹¹]-substance P 6-11; [D-Ala⁴]-substance P 4-11; [Tyr⁶, D-Phe⁷, D-His⁹]-substance P 6-11 (sendide); biotinyl-substance P; biotinyl-NTE [Arg³]-substance P; [Tyr⁸]-substance P; [Sar⁹, Met(O2)¹¹]-substance P; [D-Pro², D-Trp⁷,⁹]-substance P; [D-Pro⁴, 0-Trp⁷,⁹]-substance P 4-11; substance P 4-11; [DTrp²,⁷,⁹]-substance P; [(Dehydro)Pro²,⁴, Pro⁹]-substance P; [Dehydro-Pro⁴]-substance P 4-11; [Glp⁵,(Me)Phe⁸,Sar⁹]-substance P 5-11; [Glp⁵,Sar⁹]-substance P 5-11; [Glp⁵]-substance P 5-11; hepta-substance P (substance P 5-11); hexa-substance P(substance P 6-11); [MePhe⁸,Sar⁹]-substance P; [Nle¹¹]-substance P; Octa-substance P(substance P 4-11); [pGlu¹]-hexa-substance P ([pGlu⁶]-substance P 6-11); [pGlu⁶, D-Pro⁹]-substance P 6-11; [(pNO2)Phe⁷Nle¹¹]-substance P; penta-substance P (substance P 7-11); [Pro⁹]-substance P; GR73632, substance P 7-11; [Sar⁴]-substance P 4-11; [Sar⁹]-substance P; septide ([pGlu⁶, Pro⁹]-substance P 6-11); spantide I; spantide II; substance P; substance P, cod; substance P, trout; substance P antagonist; substance P-Gly-Lys-Arg; substance P 1-4; substance P 1-6; substance P 1-7; substance P 1-9; deca-substance P (substance P 2-11); nona-substance P (substance P 3-11); substance P tetrapeptide (substance P 8-11); substance P tripeptide (substance P 9-11); substance P, free acid; substance P methyl ester; and [Tyr⁸,Nle¹¹] substance P.

Tachykinin peptides including, but not limited to, [Ala⁵, beta-Ala⁸] neurokinin A 4-10; eledoisin; locustatachykinin I (Lom-TK-I) (*Locusta migratoria*); locustatachykinin II (Lom-TK-II) (*Locusta migratoria*); neurokinin A 4-10; neurokinin A (neuromedin L, substance K); neurokinin A, cod and trout; biotinyl-neurokinin A (biotinyl-neuromedin L, biotinyl-substance K); [Tyr⁰]-neurokinin A; [Tyr⁶]-substance K; FR64349; [Lys³, Gly⁸-(R)-gamma-lactam-Leu⁹]-neurokinin A 3-10; GR83074; GR87389; GR94800; [Beta-Ala⁸]-neurokinin A 4-10; [Nle¹⁰]-neurokinin A 4-10; [Trp⁷, beta-Ala⁸]-neurokinin A 4-10; neurokinin B (neuromedin K); biotinyl-neurokinin B (biotinyl-neuromedin K); [MePhe⁷]-neurokinin B; [Pro⁷]-neurokinin B; [Tyr⁰]-neurokinin B; neuromedin B, porcine; biotinyl-neuromedin B, porcine; neuromedin B-30, porcine; neuromedin B-32, porcine; neuromedin B receptor antagonist; neuromedin C, porcine; neuromedin N, porcine; neuromedin (U-8), porcine; neuromedin (U-25), porcine; neuromedin U, rat; neuropeptide-gamma (gamma-preprotachykinin 72-92); PG-KII; phyllolitorin; [Leu⁸]-phyllolitorin (*Phyllomedusa sauvagei*); physalaemin; physalaemin 1-11; scyliorhinin II, amide, dogfish; senktide, selective neurokinin B receptor peptide; [Ser²]-neuromedin C; beta-preprotachykinin 69-91, human; beta-preprotachykinin 111-129, human; tachyplesin I; xenopsin; and xenopsin 25 (xenin 25), human.

Thyrotropin-releasing hormone (TRH) peptides including, but not limited to, biotinyl-thyrotropin-releasing hormone; [Glu¹]-TRH; His-Pro-diketopiperazine; [3-Me-His²]-TRH; pGlu-Gln-Pro-amide; pGlu-His; [Phe²]-TRH; prepro TRH 53-74; prepro TRH 83-106; prepro-TRH 160-169 (Ps4, TRH-potentiating peptide); prepro-TRH 178-199; thyrotropin-releasing hormone (TRH); TRH, free acid; TRH-SH Pro; and TRH precursor peptide.

Toxin peptides including, but not limited to, omega-agatoxin TK; agelenin, (spider, *Agelena opulenta*); apamin (honeybee, *Apis mellifera*); calcicudine (CaC) (green mamba, *Dedroaspis angusticeps*); calciseptine (black mamba, *Dendroaspis polylepis polylepis*); charybdotoxin (ChTX) (scorpion, *Leiurus quinquestriatus* var. *hebraeus*); chlorotoxin; conotoxin GI (marine snail, *Conus geographus*); conotoxin GS (marine snail, *Conus geographus*); conotoxin MI (Marine *Conus magus*); alpha-conotoxin EI, *Conus ermineus*; alpha-conotoxin SIA; alpha-conotoxin ImI; alpha-conotoxin SI (cone snail, *Conus striatus*); micro-conotoxin GIIIB (marine snail, *Conus geographus*); omega-conotoxin GVIA (marine snail, *Conus geographus*); omega-conotoxin MVIIA (*Conus magus*); omega-conotoxin MVIIC (*Conus magus*); omega-conotoxin SVIB (cone snail, *Conus striatus*); endotoxin inhibitor; geographutoxin I (GTX-I) (μ-Conotoxin GIIIA); iberiotoxin (IbTX) (scorpion, *Buthus tamulus*); kaliotoxin 1-37; kaliotoxin (scorpion, *Androctonus mauretanicus mauretanicus*); mast cell-degranulating peptide (MCD-peptide, peptide 401); margatoxin (MgTX) (scorpion, *Centruriodes Margaritatus*); neurotoxin NSTX-3 (pupua new guinean spider, *Nephilia maculata*); PLTX-II (spider, *Plectreurys tristes*); scyllatoxin (leiurotoxin I); and stichodactyla toxin (ShK).

Vasoactive intestinal peptides (VIP/PHI) including, but not limited to, VIP, human, porcine, rat, ovine; VIP-Gly-Lys-Arg-NH2; biotinyl-PHI (biotinyl-PHI-27), porcine; [Glp¹⁶] VIP 16-28, porcine; PHI (PHI-27), porcine; PHI (PHI-27), rat; PHM-27 (PHI), human; prepro VIP 81-122, human; preproVIP/PHM 111-122; prepro VIP/PHM 156-170; biotinyl-PHM-27 (biotinyl-PHI), human; vasoactive intestinal contractor (endothelin-beta); vasoactive intestinal octacosa-peptide, chicken; vasoactive intestinal peptide, guinea pig; biotinyl-VIP, human, porcine, rat; vasoactive intestinal peptide 1-12, human, porcine, rat; vasoactive intestinal peptide 10-28, human, porcine, rat; vasoactive intestinal peptide 11-28, human, porcine, rat, ovine; vasoactive intestinal peptide (cod, *Gadus morhua*); vasoactive intestinal peptide 6-28; vasoactive intestinal peptide antagonist; vasoactive intestinal peptide antagonist ([Ac-Tyr$^1$, D-Phe$^2$]-GHRF 1-29 amide); vasoactive intestinal peptide receptor antagonist (4-Cl-D-Phe$^6$, Leu$^{17}$]-VIP); and vasoactive intestinal peptide receptor binding inhibitor, L-8-K.

Vasopressin (ADH) peptides including, but not limited to, vasopressin; [Asu$^{1,6}$,Arg$^8$]-vasopressin; vasotocin; [Asu$^{1,6}$, Arg$^8$]-vasotocin; [Lys$^8$]-vasopressin; pressinoic acid; [Arg$^8$]-desamino vasopressin desglycinamide; [Arg$^8$]-vasopressin (AVP); [Arg$^8$]-vasopressin desglycinamide; biotinyl-[Arg$^8$]-vasopressin (biotinyl-AVP); [D-Arg$^8$]-vasopressin; desamino-[Arg$^8$]-vasopressin; desamino-[D-Arg$^8$]-vasopressin (DDAVP); [deamino-[D-3-(3'-pyridyl-Ala)]-[Arg$^8$]-vasopressin; [1-(beta-Mercapto-beta, beta-cyclopentamethylene propionic acid), 2-(O-methyl) tyrosine]-[Arg$^8$]-vasopressin; vasopressin metabolite neuropeptide [pGlu$^4$, Cys$^6$]; vasopressin metabolite neuropeptide [pGlu$^4$, Cys$^6$]; [Lys$^8$]-deamino vasopressin desglycinamide; [Lys$^8$]-vasopressin; [Mpr$^1$,Val$^4$,DArg$^8$]-vasopressin; [Phe$^2$, Ile$^3$, Orn$^8$]-vasopressin ([Phe$^2$, Orn$^8$]-vasotocin); [Arg$^8$]-vasotocin; and [d(CH2)5, Tyr(Me)$^2$, Orn$^8$]-vasotocin.

Virus related peptides including, but not limited to, fluorogenic human CMV protease substrate; HCV core protein 59-68; HCV NS4A protein 18-40 (JT strain); HCV NS4A protein 21-34 (JT strain); hepatitis B virus receptor binding fragment; hepatitus B virus pre-S region 120-145; [Ala$^{127}$]-hepatitus B virus pre-S region 120-131; herpes virus inhibitor 2; HIV envelope protein fragment 254-274; HIV gag fragment 129-135; HIV substrate; P 18 peptide; peptide T; [3,5 diiodo-Tyr$^7$] peptide T; R15K HIV-1 inhibitory peptide; T20; T21; V3 decapeptide P 18-110; and virus replication inhibiting peptide.

While certain analogs, fragments, and/or analog fragments of the various polypeptides have been described above, it is to be understood that other analogs, fragments, and/or analog fragments that retain all or some of the activity of the particular polypeptide can also be useful in embodiments of the present invention. The peptides and polypeptides of this invention can be obtained from conventional sources. For example, the peptide or polypeptide can be isolated in whole or in part from a natural source and/or the peptide or polypeptide can be produced by recombinant technology and/or by synthetic methods as are well known in the art. Analogs of this invention can be obtained by various means, as will be understood by those skilled in the art. For example, certain amino acids can be substituted for other amino acids in a polypeptide or peptide of this invention without appreciable loss of interactive binding capacity with structures such as, for example, antigen-binding regions of antibodies or binding sites on substrate molecules. As the interactive capacity and nature of a peptide or polypeptide drug defines its biological functional activity, certain amino acid sequence substitutions can be made in the amino acid sequence and nevertheless remain a peptide or polypeptide with like properties.

In making such substitutions, the hydropathic index of amino acids can be considered. The importance of the hydropathic amino acid index in conferring interactive biologic function on a peptide or polypeptide is generally understood in the art. It is accepted that the relative hydropathic character of the amino acid contributes to the secondary structure of the resultant polypeptide, which in turn defines the interaction of the polypeptide with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids can be substituted by other amino acids having a similar hydropathic index or score and still result in a peptide or polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101 provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that can be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As used herein, the term "drug peptide or polypeptide" means a peptide or polypeptide possessing at least some of the biological activity of a drug (e.g., the ability to affect the body through a drug's primary mechanism of action). For example, an insulin polypeptide can be a polypeptide such as insulin having an A-chain polypeptide and a B-chain polypeptide coupled to the A-chain polypeptide by disulfide bonds. In various embodiments of the present invention, the drug peptide or polypeptide can possess a majority of the biological activity of a drug, and can possess substantially all of the biological activity of a drug, and in certain embodiments, possesses all of the biological activity of a drug.

As used herein, the term "peptide or polypeptide drug analog" means a peptide or polypeptide possessing at least some of the biological activity of a drug wherein one or more of the amino acids have been replaced while retaining some or all of the activity of the drug. The analog is described by noting the replacement amino acids with the position of the replacement as a superscript followed by a description of the drug. For example, "Pro$^{B29}$ insulin, human" means that the lysine typically found at the B29 position of a human insulin molecule has been replaced with proline. As another example, "Pro$^2$ calcitonin, human-" means that the glycine typically found at the 2 position of a human calcitonin molecule has been replaced with proline. Peptide or polypeptide drug analogs can be obtained by various means as described above.

As used herein, the term "peptide or polypeptide drug fragment" means a segment of the amino acid sequence found in the peptide or polypeptide drug that retains some or all of the activity of the peptide or polypeptide drug. Peptide or polypeptide drug fragments are denoted by stating the position(s) in an amino acid sequence followed by a description of the amino acid. For example, a "B25-B30 human insulin" fragment would be the six amino acid sequence corresponding to the B25, B26, B27, B28, B29 and B30 positions in the human insulin amino acid sequence.

As used herein, the term "peptide or polypeptide drug fragment analog" means a segment of the amino acid sequence found in the peptide or polypeptide drug molecule wherein one or more of the amino acids in the segment have been replaced while retaining some or all of the activity of the peptide or polypeptide drug.

As used herein, the term "calcitonin" means calcitonin of one of the following species: chicken, eel, human, porcine, rat, salmon, or the like provided by natural, synthetic, or genetically engineered sources (i.e., recombinantly).

As used herein, the term "insulin" means the insulin of one of the following species: human, cow, pig, sheep, horse, dog, chicken, duck, whale, or the like provided by natural, synthetic, or genetically engineered sources (i.e., recombinantly. In various embodiments of the present invention, insulin is human insulin.

As used herein, the term "peptide or polypeptide" means an amino acid sequence comprising at least two amino acid residues.

As used herein, the term "amphiphilically balanced" means capable of substantially dissolving in water and capable of penetrating biological membranes.

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—CH$_2$—CH$_2$—O—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

Unless otherwise noted herein, the term "bile salt" includes bile salts and the free acids thereof.

Unless otherwise noted herein, the term "fatty acid" includes fatty acids and pharmaceutically acceptable salts or esters thereof.

As used herein, the term "bile salt component" means a mixture of one or more salts.

As used herein, the term "fatty acid component" means a mixture of one or more fatty acids.

As used herein, the "precipitation point" of a compound or component of the pharmaceutical composition is the pH at which at least 25% of the compound or component precipitates out of the composition. Accordingly, lowering the precipitation point means lowering the pH at which at least 25% of the compound or component precipitates out of the composition. Conversely, raising the precipitation point means raising the pH at which at least 25% of the compound or component precipitates out of the composition. The precipitation point of a compound or component of a pharmaceutical composition of this invention can be determined according to methods well known in the art.

As used herein, the "solubility point" of a compound or component of the pharmaceutical composition is the pH at which at least 75% of the compound or component is solubilized in the composition. Accordingly, lowering the solubility point means lowering the pH at which at least 75% of the compound or component is solubilized in the composition. Conversely, raising the solubility point means raising the pH at which at least 75% of the compound or component is solubilized in the composition. The solubility point of a compound or component of a pharmaceutical composition of this invention can be determined according to methods well known in the art.

As used herein, the term "medium-chain fatty acid" means a saturated or unsaturated fatty acid having from 8 to 14 carbon atoms.

As used herein, the term "long-chain fatty acid" means a saturated or unsaturated fatty acid having greater than 14 carbon atoms.

According to embodiments of the present invention, a pharmaceutical composition comprises a drug and/or a drug-oligomer conjugate, a fatty acid component, and a bile salt component or a bile salt alone. The drug-oligomer conjugate includes a drug covalently coupled to an oligomeric moiety. The fatty acid component includes a fatty acid, and the bile salt component includes a bile salt.

According to these embodiments of the present invention, the fatty acid component and the bile salt component, when together, can be present in a weight-to-weight ratio of between 1:15 and 15:1 or any value in between. For example, the fatty acid component and the bile salt component can be present in various embodiments of this invention in a weight-to-weight ratio of between 1:10 and 10:1, 1:5 and 5:1, 1:3 and 3:1, or 1:2 and 2:1 or any value between 1:15 and 15:1.

According to some embodiments of the present invention, the fatty acid component is present in an amount sufficient to lower the precipitation point of the bile salt compared to a precipitation point of the bile salt if the fatty acid component were not present in the pharmaceutical composition. The fatty acid component can be present in an amount sufficient to lower the precipitation point of the bile salt by at least 0.5 pH units, and can also be present in an amount sufficient to lower the precipitation point of the bile salt by at least 1.0 pH units.

According to other embodiments of the present invention, the bile salt component is present in an amount sufficient to lower the solubility point of the fatty acid compared to a solubility point of the fatty acid if the bile salt were not present in the pharmaceutical composition. The bile salt component can be present in an amount sufficient to lower the solubility point of the fatty acid by at least 0.25 pH units, and can also be present in an amount sufficient to lower the solubility point of the fatty acid by at least 0.5 pH units.

According to still other embodiments of the present invention, the fatty acid component is present in an amount sufficient to lower the precipitation point pH of the bile salt compared to a precipitation point pH of the bile salt if the fatty acid were not present in the pharmaceutical composition as described above, and the bile salt component is present in an amount sufficient to lower the solubility point pH of the fatty acid compared to a solubility point pH of the fatty acid if the bile salt were not present in the pharmaceutical composition as described above.

The bile salt in the bile salt component can be various bile salts as will be understood by those skilled in the art including unconjugated and conjugated bile salts. Unconjugated bile salts are bile salts in which the primary side chain has a single carboxyl group which is at the terminal position and which is unsubstituted. Exemplary unconjugated bile salts include, but are not limited to, cholate, ursodeoxycholate, chenodeoxycholate, and deoxycholate. Conjugated bile salts are bile salts in which the primary side chain has a carboxyl group which is substituted with, for example, an amino acid derivative linked via its nitrogen atom to the carboxyl group. Exemplary conjugated bile salts include, but are not limited to, taurocholate, glycocholate, taurodeoxycholate, and glycodeoxycholate. Mixtures of the various unconjugated and conjugated bile salts can also be used. The bile salt can be a pharmaceutically acceptable salt of cholic acid and the bile salt can be sodium cholate. In certain embodiments, the bile salt component consists essentially of sodium cholate.

The fatty acid in the fatty acid component can be various fatty acids as will be understood by those skilled in the art including natural and synthetic fatty acids. The fatty acid can have between a lower limit of 2, 3, 4, 5, 6, 7, 8, 9, 10, 11, 12, 13, 14, 15, 16, 17, 18, or 19 carbon atoms and an upper limit of 3, 4, 5, 6, 7, 8, 9, 10, 11, 12, 13, 14, 15, 16, 17, 18, 19, 20, 21, or 22 carbon atoms. The fatty acid can be either saturated or unsaturated. Exemplary saturated fatty acids include, but are not limited to, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, one or more of which can be referred to by their common names such as acetic acid, caproic acid, caprylic acid, capric acid, lauric acid, myristic acid, palmitic acid, stearic acid, arachidic acid, behenic acid, lignoceric acid, and cerotic acid. Exemplary unsaturated fatty acids include, but are not limited to, cis-9-octadecenoic acid, trans-9-octadecenoic acid, 9,12-octadecatrienoic acid, 9,12,15-octadecenoic acid, and 5,8,11,14-eicosatetraenoic acid, one or more of which can be referred to by their common names such as oleic acid, elaidic acid, linoleic acid, linolenic acid, and arachidonic acid.

In some embodiments, the fatty acid component comprises a mixture of two or more fatty acids. In other embodiments, the fatty acid component comprises a medium-chain fatty acid and a long-chain fatty acid. The medium-chain fatty acid can be capric acid, lauric acid, or a mixture thereof. The long-chain fatty acid can be oleic acid.

The drug can be various drugs as described above and can be conjugated to oligomers as will be understood by those skilled in the art. In some embodiments, the drug is a small molecule drug such as the anti-cancer drug taxane, which is described in U.S. Pat. No. 6,380,405 to Ekwuribe et al., the disclosure of which is incorporated herein in its entirety. In other embodiments, the drug is a peptide or polypeptide drug, such as those described above. In certain embodiments of this invention, the polypeptide drug can be an insulin polypeptide, a calcitonin polypeptide, a growth hormone polypeptide, or an etoposide polypeptide.

The oligomer in the drug-oligomer conjugates of this invention can be various oligomers as will be understood by those skilled in the art. In general, the oligomer may be any oligomer capable of being coupled to a drug as will be understood by those skilled in the art. For example, the oligomer may be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al., and U.S. Pat. No. 6,380,405 to Ekwuribe et al., the disclosures of each of which are incorporated herein by reference in their entireties. As another example, the oligomer may be a non-polydispersed oligomer as described in U.S. Pat. No. 6,835,802 to Ekwuribe et al. U.S. Pat. No. 6,858,580 Ekwuribe et al. U.S. Pat. No. 6,828,297 to Ekwuribe et al. U.S. Pat. No. 6,713,452 to Ekwuribe et al.; and U.S. Pat. No. 6,828,305 to Ekwuribe et al. entitled, the disclosures of each of which are incorporated herein in their entireties.

In some embodiments, the oligomer comprises a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety can be a polyalkylene glycol moiety. The polyalkylene glycol moiety has at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 polyalkylene glycol subunits and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can have between a lower limit of 2, 3, 4, 5, or 6 polyalkylene glycol subunits and an upper limit of 5, 6, 7, 8, 9, 10, 11, 12, 13, 14, 15, 16, 17, 18, 19, or 20 polyalkylene glycol subunits. The polyalkylene glycol moiety can have between a lower limit of 3, 4, 5, or 6 polyalkylene glycol subunits and an upper limit of 5, 6, 7, 8, 9, 10, 11, or 12 polyalkylene glycol subunits. The polyalkylene glycol moiety can also have between a lower limit of 4, 5, or 6 polyalkylene glycol subunits and an upper limit of 6, 7, or 8 polyalkylene glycol subunits. The polyalkylene glycol moiety of the oligomer can also be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

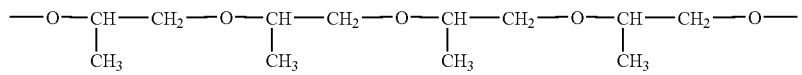

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

The oligomer can comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer can further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

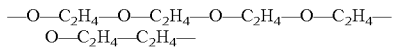

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

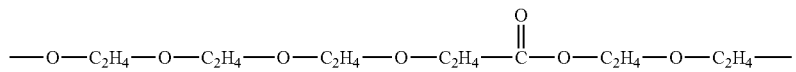

is a polyethylene glycol moiety having four polyethylene glycol subunits and an additional hydrophilic moiety having two polyethylene glycol subunits. Oligomers of this invention can comprise a polyalkylene glycol moiety and no additional hydrophilic moieties.

The oligomer can further comprise one or more lipophilic moieties as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, 20, 21, 22, 23, 24, 25, 26, 27, 28, or 29 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can have between a lower limit of 2, 3, 4, 5, 6, 7, 8, 9, or 10 carbon atoms and an upper limit of 4, 5, 6, 7, 8, 9, 10, 11, 12, 13, 14, 15, 16, 17, 18, 19, 20, 21, or 22 carbon atoms. The lipophilic moiety can also have between a lower limit of 3, 4, 5, 6, 7, 8, or 9 carbon atoms and an upper limit of 4, 5, 6, 7, 8, 9, 10, 11, 12, 13, or 14 carbon atoms. The lipophilic moiety can, in some embodiments, have between a lower limit of 3, 4, 5, 6, or 7 carbon atoms and an upper limit of 6, 7, 8, 9, or 10 carbon atoms. The lipophilic moiety can be, but is not limited to, saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate. The fatty acid moiety can be natural or synthetic.

The oligomer can further comprise one or more spacer moieties as will be understood by those skilled in the art. Spacer moieties can, for example, be used to separate a hydrophilic moiety from a lipophilic moiety, to separate a lipophilic moiety or hydrophilic moiety from the drug, to separate a first hydrophilic or lipophilic moiety from a second hydrophilic or lipophilic moiety, or to separate a hydrophilic moiety or lipophilic moiety from a linker moiety. Spacer moieties can be sugar, cholesterol and/or glycerine moieties. Sugar moieties can be various sugar moieties as will be understood by those skilled in the art including, but not limited to, monosaccharide moieties and disaccharide moieties. In some embodiments, the monosaccharide moieties can have between 4 and 6 carbon atoms.

The oligomer can further comprise one or more linker moieties that are used to couple the oligomer with the drug as will be understood by those skilled in the art. Linker moieties can be, but are not limited to, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, and can also have between 1, 2, 3, 4, or 5 carbon atoms and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can be a natural or synthetic fatty acid. The fatty acid linker moiety can have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms and can have between 1, 2, 3, 4, or 5 carbon atoms and 8, 10, 12, 14 or 16 carbon atoms. When the linker moiety is a fatty acid, the oligomeric moiety can be coupled to the drug via the carbonyl group of a carboxylic acid moiety of the fatty acid.

The oligomer can further comprise one or more terminating moieties at the one or more ends of the oligomer, which are not coupled to the drug. The terminating moiety can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 carbon atoms and an upper limit of 5, 6, 7, 8, 9, 10, 11, 12, 13, or 14 carbon atoms. The alkyl or alkoxy moiety in some embodiments can have between a lower limit of 1, 2, 3, 4, or 5 carbon atoms and an upper limit of 5, 6, 7, 8, 9, or 10 carbon atoms. The alkyl or alkoxy moiety can also have between a lower limit of 1, 2, 3, or 4 carbon atoms and an upper limit of 5, 6, or 7 carbon atoms. The alkyl moiety can be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methylpentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In some embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugars, cholesterol, alcohols, and fatty acids.

According to embodiments of the present invention, the drug-oligomer conjugate comprises the structure of Formula I:

$$\text{Drug-B-L}_j\text{-G}_k\text{-R-G}'_m\text{-R'-G}''_n\text{-T} \qquad (I)$$

wherein:
Drug is a drug of this invention;
B is a bonding moiety;
L is a linker moiety;
G, G' and G'' are individually selected spacer moieties;
R is a lipophilic moiety and R' is a polyalkylene glycol moiety, or R' is the lipophilic moiety and R is the polyalkylene glycol moiety and only one of R or R' can be present
T is a terminating moiety; and
j, k, m and n are individually 0 or 1.

The bonding moiety can be an ester moiety, a thio-ester moiety, an ether moiety, a carbamate moiety, a thio-carbamate moiety, a carbonate moiety, a thio-carbonate moiety, an amide moiety, a urea moiety, and/or a covalent bond. The linker moiety, spacer moieties, lipophilic moiety, polyalkylene glycol moiety, and terminating moiety are described herein. In some embodiments of this invention, oligomers do not include spacer moieties (i.e., k, m and n are 0).

In some embodiments of conjugate according to Formula I, the drug is a polypeptide drug of this invention. The polypeptide drug can be an insulin polypeptide, a calcitonin polypeptide, or a growth hormone polypeptide. The insulin polypeptide can be insulin and can be human insulin. The calcitonin polypeptide can be salmon calcitonin or human calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-2 1) (C-procalcitonin), and N-proCT (amino-terminal procalcitonin cleavage peptide), human. Calcitonin analogs can be provided by substitution of one or more amino acids in calcitonin as described above. Calcitonin fragments include, but are not limited to, calcitonin 1-7, human; and calcitonin 8-32, salmon. Calcitonin fragment analogs can be provided by substitution of one or more of the amino acids in a calcitonin fragment as described herein.

In other embodiments, the drug-oligomer conjugate comprises the structure of Formula II:

$$\text{Drug-X(CH}_2)_m\text{Y(C}_2\text{H}_4\text{O})_n\text{R} \qquad (II)$$

wherein:
Drug is a drug of this invention;
X is —C(O)— or —O—;

Y is an ester, an ether, a carbamate, a carbonate, or an amide bonding moiety, and in certain embodiments, can be an ether bonding moiety;

m is between a lower limit of 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits, and in certain embodiments, is 7; and R is a terminating moiety as described herein.

In some embodiments of conjugates according to Formula II, the drug is a peptide or polypeptide drug as described herein. The polypeptide drug can be an insulin polypeptide, a calcitonin polypeptide, or a growth hormone polypeptide. The insulin polypeptide can be insulin and can be human insulin. The calcitonin polypeptide can be salmon calcitonin or human calcitonin, and in specific embodiments, can be salmon calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs can be provided by substitution of one or more amino acids in calcitonin as described above. Calcitonin fragments include, but are not limited to, calcitonin 1-7, human; and calcitonin 8-32, salmon. Calcitonin fragment analogs can be provided by substitution of one or more of the amino acids in a calcitonin fragment as described above.

In still other embodiments, the drug-oligomer conjugate comprises the structure of Formula III:

Drug-X$_1$—(CH$_2$)$_m$(OC$_2$H$_4$)$_n$OR  (III)

wherein:
Drug is a drug of this invention;
X$_1$ is —C(O)— or —O—;
m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 2, 3, 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, andor between a lower limit of 4, 5, or 6 and an upper limit of 6, 7, or 8 polyalkylene glycol subunits; and R is a terminating moiety as described herein.

In some embodiments of conjugate according to Formula III, the drug is a peptide or polypeptide drug as described above. The polypeptide drug can be an insulin polypeptide, a calcitonin polypeptide, or a growth hormone polypeptide. The insulin polypeptide can be insulin and can be human insulin. The calcitonin polypeptide can be salmon calcitonin or human calcitonin, and in certain embodiments, can be salmon calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs can be provided by substitution of one or more amino acids in calcitonin as described above. Calcitonin fragments include, but are not limited to, calcitonin 1-7, human; and calcitonin 8-32, salmon. Calcitonin fragment analogs can be provided by substitution of one or more of the amino acids in a calcitonin fragment as described above.

In yet other embodiments, the drug-oligomer conjugate comprises the structure of Formula IV:

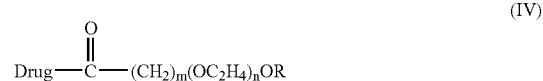

(IV)

wherein:
Drug is a drug of this invention;
m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, anc can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits; and R is a terminating moiety as described herein.

In some embodiments of conjugates according to Formula IV, the drug is a peptide or polypeptide drug as described above. The polypeptide drug can be an insulin polypeptide, a calcitonin polypeptide, or a growth hormone polypeptide. The insulin polypeptide can be insulin and can be human insulin. The calcitonin polypeptide can be salmon calcitonin or human calcitonin, and in certain embodiments, can be salmon calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs can be provided by substitution of one or more amino acids in calcitonin as described above. Calcitonin fragments include, but are not limited to, calcitonin 1-7, human; and calcitonin 8-32, salmon. Calcitonin fragment analogs can be provided by substitution of one or more of the amino acids in a calcitonin fragment as described above.

When the drug in the drug-oligomer conjugate of Formula IV is salmon calcitonin, the drug-oligomer can comprise the following structure:

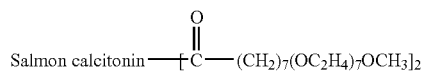

where one of the oligomers is coupled to lysine at position 11 of the salmon calcitonin and where the other oligomer is coupled to lysine at position 18 of the salmon calcitonin. This salmon calcitonin-oligomer conjugate is referred to as CT-025.

In still other embodiments, the drug-oligomer conjugate comprises the structure of Formula V:

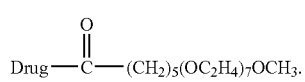

In some embodiments according to conjugates of Formula V, the drug is a peptide or polypeptide drug as described above. The polypeptide drug can be an insulin polypeptide, a calcitonin polypeptide, a C-peptide polypeptide, or a growth hormone polypeptide. The insulin polypeptide can be insulin and can be human insulin. When the drug is human insulin and the conjugate of Formula V consists of the single oligomer coupled to the Lysine at the B29 position of the human insulin, the insulin-oligomer conjugate is referred to as HIM2, The C-peptide polypeptide can be human C-peptide, having glutamate at its N-terminus and lysine at its C-terminus, with the oligomer CH$_3$O(C$_2$H$_4$O)C(O)— attached to the ε-amino group of the lysine of the human C-peptide. The calcitonin polypeptide can be salmon calcitonin or human calcitonin, and in certain embodiments, can be salmon calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs can be provided by substitution of one or more amino acids in calcitonin as described above. Calcitonin fragments include, but are not limited to, calcitonin 1-7, human; and calcitonin 8-32, salmon. Calcitonin fragment analogs can be provided by substitution of one or more of the amino acids in a calcitonin fragment as described above.

In still other embodiments of the present invention, the drug-oligomer conjugate comprises the structure of Formula VI:

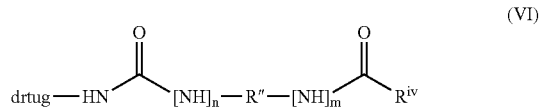

wherein:

Drug is a drug of this invention;

R''' is a hydrophilic moiety; which can be a polyalkylene glycol moiety; and can also be a lower polyalkylene glycol moiety; and in certain embodiments, can be a polyethylene glycol moiety or polypropylene glycol moiety, where the polyalkylene glycol moiety has at least 1, 2, or 3 polyalkylene glycol subunits; and R$^{iv}$ is a lipophilic moiety; which can be an alkyl moiety having between 1 and 24 carbon atoms; and in certain embodiments, can be a lower alkyl moiety;

R$^{iv}$ is a hydrophilic moiety; which can be a polyalkylene glycol moiety; and can also be a lower polyalkylene glycol moiety; and in certain embodiments, can be a polyethylene glycol moiety or polypropylene glycol moiety, where the polyalkylene glycol moiety has at least 1, 2, or 3 polyalkylene glycol subunits; and R''' is a lipophilic moiety; which can be an alkyl moiety having between 1 and 24 carbon atoms; and in certain embodiments, can be a lower alkyl moiety; and n and m are individually 0 or 1.

In some embodiments of conjugate according to Formula VI, the drug is a peptide or polypeptide drug as described above. The polypeptide drug can be an insulin polypeptide, a calcitonin polypeptide, or a growth hormone polypeptide. The insulin polypeptide can be insulin and can be human insulin. The calcitonin polypeptide can be salmon calcitonin or human calcitonin, and in certain embodiments, can be salmon calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs can be provided by substitution of one or more amino acids in calcitonin as described above.

Calcitonin fragments include, but are not limited to, calcitonin 1-7, human; and calcitonin 8-32, salmon. Calcitonin fragment analogs can be provided by substitution of one or more of the amino acids in a calcitonin fragment as described above.

When the drug portion of the drug-oligomer conjugate of Formula VI is human insulin, R''' can be polyethylene glycol having between a lower limit of 1, 2, 3, 4, 5, 6, or 7 polyethylene glycol subunits and an upper limit of 2, 3, 4, 5, 6, 7, 8, 9, or 10 polyethylene glycol subunits or R''' is polypropylene glycol having between a lower limit of 1, 2, 3, 4, 5, 6, or 7 polypropylene glycol subunits and an upper limit of 2, 3, 4, 5, 6, 7, 8, 9, or 10 polypropylene glycol subunits, and $R^{iv}$ can be an alkyl having 1, 2, 3, 4, 5, 6, 7, 8, 9, 10, 11, 12, 13, 14, 15, 16, 17, 18, 19, or 20 carbon atoms. In some embodiments, R''' is polyethylene glycol having between a lower limit of 1, 2, 3, or 4 polyethylene glycol subunits and an upper limit of 2, 3, 4, 5, 6, or 7 polyethylene glycol subunits or R''' is polypropylene glycol having between a lower limit of 1, 2, 3, or 4 polypropylene glycol subunits and an upper limit of 2, 3, 4, 5, 6, or 7 polypropylene glycol subunits, and $R^{iv}$ is alkyl having 1, 2, 3, 4, 5, 6, 7, 8, 9, or 10 carbon atoms. In other embodiments, R''' is polyethylene glycol having between a lower limit of 1, 2, or 3 polyethylene glycol subunits and an upper limit of 3, 4, or 5 polyethylene glycol subunits or R''' is polypropylene glycol having between a lower limit of 1, 2, or 3 polypropylene glycol subunits and an upper limit of 3, 4, or 5 polypropylene glycol subunits, and $R^{iv}$ is alkyl having 3, 4, 5, or 6 carbon atoms.

In yet other embodiments of the present invention, the drug-oligomer conjugate comprises the structure of Formula VII:

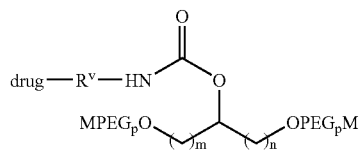

(VII)

wherein:
Drug is a drug of this invention;
$R^v$ is an alkyl or a fatty acid moiety as described herein with reference to the lipophilic moiety; and
p is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10; and
m and n are each at least 1 and m+n is from 2–17, preferably 4–15 and more preferably 4–9.

In some embodiments of conjugate according to Formula VII, the drug is a peptide or polypeptide drug as described above. The polypeptide drug can be an insulin polypeptide, a calcitonin polypeptide, or a growth hormone polypeptide. The insulin polypeptide can be insulin and can be human insulin. The calcitonin polypeptide can be salmon calcitonin or human calcitonin, and in certain embodiments, can be salmon calcitonin. However, it is to be understood that the calcitonin polypeptide can be selected from various calcitonin polypeptides known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs can be provided by substitution of one or more amino acids in calcitonin as described above. Calcitonin fragments include, but are not limited to, calcitonin 1-7, human; and calcitonin 8-32, salmon. Calcitonin fragment analogs can be provided by substitution of one or more of the amino acids in a calcitonin fragment as described above.

In various embodiments described above, the oligomer is covalently coupled to the drug. In some embodiments, the oligomer is coupled to the drug utilizing a hydrolyzable bond (e.g., an ester or carbonate bond). A hydrolyzable coupling can provide a drug-oligomer conjugate that acts as a prodrug. In certain instances, for example where the drug-oligomer conjugate is biologically inactive (i.e., the conjugate lacks the ability to affect the body through the insulin polypeptide's primary mechanism of action), a hydrolyzable coupling can provide for a time-release or controlled-release effect, providing the biologically active drug over a given time period as one or more oligomers are cleaved from their respective biologically inactive drug-oligomer conjugates to provide the biologically active drug. In other embodiments, the oligomer is coupled to the drug utilizing a non-hydrolyzable bond (e.g., a carbamate, amide, or ether bond). Use of a non-hydrolyzable bond can be preferable when it is desirable to allow the biologically inactive drug-oligomer conjugate to circulate in the bloodstream for an extended period of time, preferably at least 2 hours.

Oligomers employed in the various embodiments described above are commercially available or can be synthesized by various methods as will be understood by those skilled in the art. For example, polydispersed oligomers can be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers can be synthesized by methods provided in one or more of the following references: U.S. Pat. No. 6,835,802 to Ekwuribe et al.; U.S. Pat. No. 6,858,580 to Ekwuribe et al.; U.S. Pat. No. 6,828,297 to Ekwuribe et al.; U.S. Pat. No. 6,713,452 to Ekwuribe et al.; and U.S. Pat. No. 6,828,305 to Ekwuribe et al. Oligomers according to embodiments of the present invention can be substantially monodispersed and can also be monodispersed. Exemplary methods for synthesizing various monodispersed oligomers are provided in the Examples section provided herein.

In various embodiments described above, more than one oligomer (i.e., a plurality of oligomers) can be coupled to the drug. The oligomers in the plurality can be the same. However, it is to be understood that the oligomers in the plurality can be different from one another, or, alternatively, some of the oligomers in the plurality can be the same and some can be different. When a plurality of oligomers is coupled to the drug, one or more of the oligomers can be coupled to the drug with hydrolyzable bonds and one or more of the oligomers can be coupled to the drug with non-hydrolyzable bonds. Alternatively, all of the bonds coupling the plurality of oligomers to the drug can be hydrolyzable, but have varying degrees of hydrolyzability such that, for example, one or more of the oligomers is rapidly removed from the drug by hydrolysis in the body and one or more of the oligomers is slowly removed from the drug by hydrolysis in the body.

The oligomer can be coupled to the drug at various nucleophilic residues of the drug including, but not limited to, nucleophilic hydroxyl functions and/or amino functions. When the drug is a peptide or polypeptide, a nucleophilic hydroxyl function can be found, for example, at serine and/or tyrosine residues, and a nucleophilic amino function can be found, for example, at histidine and/or lysine residues, and/or at the one or more N-termini of the polypeptide. When an oligomer is coupled to the one or more N-termini of the insulin polypeptide, the coupling preferably forms a secondary amine. When the drug is human insulin, for example, the oligomer can be coupled to an amino functionality of the insulin, including the amino functionality of $Gly^{A1}$, the amino functionality of $Phe^{B1}$, and the amino functionality of $Lys^{B29}$. When one oligomer is coupled to the human insulin, the oligomer is preferably coupled to the amino functionality of $Lys^{B29}$. When two oligomers are coupled to the human insulin, the oligomers are preferably coupled to the amino functionality of $Phe^{B1}$ and the amino functionality of $Lys^{B29}$. While more than one oligomer can be coupled to the human insulin, a higher activity (improved glucose lowering ability) is observed for the mono-conjugated human insulin. Monoconjugates (i.e., when one oligomer is coupled to the insulin drug) can be prepared using methods described in U.S. patent application Ser. No. 10/036,744, entitled "Methods of Synthesizing Insulin Polypeptide-Oligomer Conjugates, and Proinsulin Polypeptide-Oligomer Conjugates and Methods of Synthesizing Same," published as U.S. Pub. No. U.S. 2003-0087808. the disclosure of which is incorporated herein by reference in its entirety. When the calcitonin drug is salmon calcitonin, for example, the oligomer can be coupled to an amino functionality of the salmon calcitonin, including the amino functionality of $Lys^{11}$, $Lys^{18}$ and/or the N-terminus. While one or more oligomers can be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

According to other embodiments of the present invention, a pharmaceutical composition of this invention is provided that comprises i) a drug and/or a drug-oligomer conjugate, and ii) a fatty acid component, and a bile salt component, or a bile salt component without a fatty acid component. The drug-oligomer conjugate includes a drug covalently coupled to an oligomeric moiety. The fatty acid component includes a fatty acid, and the bile salt component includes a bile salt.

The drug-oligomer conjugate includes a drug covalently coupled to an oligomeric moiety, as described herein. The fatty acid component and the bile salt component, when together, can be present in a weight-to-weight ratio of anywhere between 1:15 and 15:1, including for example, a weight-to-weight ratio of between 1:10 and 10:1, 1:5 and 5:1, 1:3 and 3:1 and/or 1:2 and 2:1, as well as any value between 1:15 and 15:1.

According to the embodiments of the present invention, the fatty acid component can be present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were present in a second amount less than the first amount. The precipitation point of the bile salt in the formulation can be at or below a pH of 6.0, and in certain embodiments, can be at or below a pH of 5.5, The pH above the precipitation point can be various pH values above the precipitation point. In some embodiments, the pH above the precipitation point is at least 0.5 pH units above the precipitation point. In other embodiments, the pH above the precipitation point is at least 0.8 pH units above the precipitation point.

In some embodiments, the first bile salt particles have an average diameter of less than 500 microns and the second bile salt particles have an average diameter of greater than 550 microns. In other embodiments, the first bile salt particles have an average diameter of less than 100 microns and the second bile salt particles have an average diameter of greater than 150 microns.

In some embodiments, the first bile salt particles are able to re-solubilize in less than 75% of the time it would have taken for the second bile salt particles to re-solubilize. In other embodiments, the first bile salt particles are able to re-solubilize in less than half the time it would have taken for the second bile salt particles to re-solubilize.

According to still other embodiments of the present invention, a pharmaceutical composition comprises a drug and/or drug-oligomer conjugate, between 0.1 and 15% (w/v) of a fatty acid component, and between 0.1 and 15% (w/v) of a bile salt component, or a bile salt alone.

The drug-oligomer conjugate includes a drug covalently coupled to an oligomeric moiety, as described herein. The fatty acid component and the bile salt component, when together, can be present in a weight-to-weight ratio of anywhere between 1:15 and 15:1, as described herein.

According to various embodiments of the present invention, the concentration of the fatty acid component can be between a lower limit of 0.1, 0.2, 0.3, 0.4, 0.5, 0.6, 0.7, 0.8, 0.9, 1, 2, 3, 4, 5, 6, 7, 8, 9, 10, 11, 12, 13, or 14% (w/v) and an upper limit of 0.2, 0.3, 0.4, 0.5, 0.6, 0.7, 0.8, 0.9, 1, 2, 3, 4, 5, 6, 7, 8, 9, 10, 11, 12, 13, 14, or 15% (w/v). The concentration of the fatty acid component can be between 0.5 and 10% (w/v), and can also be between 0.5 and 5% (w/v), and in certain embodiments, can be between 1 and 3% (w/v).

According to various embodiments of the present invention, the concentration of the bile acid component can be between a lower limit of 0.1, 0.2, 0.3, 0.4, 0.5, 0.6, 0.7, 0.8, 0.9, 1, 2, 3, 4, 5, 6, 7, 8, 9, 10, 11, 12, 13, or 14% (w/v) and an upper limit of 0.2, 0.3, 0.4, 0.5, 0.6, 0.7, 0.8, 0.9, 1, 2, 3, 4, 5, 6, 7, 8, 9, 10, 11, 12, 13, 14, or 15% (w/v). The concentration of the bile salt component can be between 0.5 and 10% (w/v), and can also be between 1 and 5% (w/v), and in certain embodiments, can be between 2 and 4% (w/v).

The present invention also provides a pharmaceutical composition comprising a drug-oligomer conjugate comprising a drug covalently coupled to an oligomeric moiety and a bile salt, in a pharmaceutically acceptable carrier.

Further provided herein is a pharmaceutical composition comprising, in a pharmaceutically acceptable carrier: a drug; a bile salt; and a fatty acid, wherein the fatty acid and the bile salt are present in a weight-to-weight ratio of between 1:5 and 5:1, and wherein the fatty acid is present in an amount wherein the solubility of the bile salt in the presence of the fatty acid is greater than the solubility of the bile salt in a corresponding composition lacking the fatty acid.

The pharmaceutical compositions of this invention can comprise a bile salt, which can be taurocholate, taurodeoxycholate, cholate, deoxycholate, glycodeoxycholate and/or mixtures thereof.

In some embodiments, the pharmaceutical composition of this invention can comprise bile salt, which can be present in a concentration in the range of about 0.15% to about 10% bile salt and/or in the range of about 0.5% to about 5% bile salt.

The pharmaceutical compositions of this invention can have a pH of between 6.2 and 9.0 and can comprise a buffering component as described herein.

In certain embodiments, the pharmaceutical composition of this invention can be a liquid pharmaceutical composition, which can be suitable for oral administration. Alternatively, the pharmaceutical composition of this invention can be a solid dosage pharmaceutical composition.

The pharmaceutical composition of this invention in various embodiments can comprise a composition suitable for a route of administration comprising buccal, transdermal, peroral and/or nasal administration.

In some embodiments of the pharmaceutical composition of the present invention, the native drug and/or the drug oligomer conjugate can be a calcitonin polypeptide, which can be salmon calcitonin. The salmon calcitonin can be coupled to two oligomeric moieties, wherein one oligomeric moiety can be coupled to the lysine at the 11 position of the salmon calcitonin and wherein one oligomeric moiety can be coupled to the lysine at the 18 position of the salmon calcitonin. In such embodiments, the oligomeric moiety coupled to the lysine at the 11 position can comprise the structure $CH_3O(C_2H_4O)_7—(CH_2)_7—C(O)—$ and the oligomeric moiety coupled to the lysine at the 18 position of the salmon calcitonin can comprise the structure $CH_3O(C_2H_4O)_7—(CH_2)_7—C(O)—$.

The pharmaceutical composition of this invention can comprise a drug-oligomer conjugate that can be present as a substantially monodispersed mixture and/or as a monodispersed mixture.

In some embodiments, the pharmaceutical composition can comprise a drug-oligomer conjugate that can be amphiphilically balanced. The oligomeric moiety can be hydrophilic (e.g., polyethylene glycol) and/or the oligomeric moiety can be lipophilic (e.g., alkane). In certain embodiments, the oligomeric moiety can comprise a hydrophilic moiety and a lipophilic moiety.

It is also contemplated that in various embodiments, the pharmaceutical compositions of this invention can comprise a fatty acid and a bile salt, wherein the fatty acid and the bile salt can be present in a weight to weight ratio of about 1:4, 1:3, 1:2 or 1:1.

The fatty acids of this invention can be one or more fatty acids and can be in the range of $C_4$ to $C_{20}$ and the fatty acids can be, but are not limited to lauric acid, capric acid, oleic acid and/or mixtures thereof.

In certain embodiments of the invention wherein the pharmaceutical composition comprises a fatty acid and a bile salt, the bile salt can be present in a range of about 0.5% to about 20% weight/volume and the fatty acid can be present in a range of about 0.2% to about 10% weight/volume. In some embodiments, the bile salt can be cholate and the fatty acid can be laurate and in some embodiments, the bile salt can be cholate and the cholate can be present in the amount of about 1.5% weight/volume and the fatty acid can be laurate and the laurate can be present in the amount of 2% weight/volume.

In certain embodiments, the fatty acid can be caprate and laurate and the bile salt and fatty acid can be present in the proportions of three parts bile salt, one part caprate and one part laurate.

The present invention additionally provides a method of treating a bone disorder in a subject in need of such treatment, said method comprising administering to the subject a therapeutically effective amount of a pharmaceutical composition of this invention.

The methods of this invention can comprise orally administering the pharmaceutical composition to the subject and/or administering the composition by buccal, transdermal, peroral and/or nasal administration.

In additional embodiments, the present invention provides herein a method of delivering a drug and/or a drug oligomer conjugate across the gut wall in a subject by simultaneously contacting the gut wall with 1) a bile salt and the drug oligomer conjugate, 2) a bile salt and the drug, 3) a bile salt, a fatty acid and the drug oligomer conjugate, and/or 4) a bile salt, a fatty acid and the drug, comprising administering to the subject the various pharmaceutical compositions of this invention comprising drugs and/or drug oligomer conjugates and comprising bile salts and fatty acids or comprising bile salts, as described herein.

In some embodiments of the methods of delivering a drug and/or drug/oligomer conjugate across the gut wall, the fatty acids can be laurate and caprate and the fatty acids and bile salts can be present in the pharmaceutical composition in the ratio of three parts bile salt, one part laurate and one part caprate.

Pharmaceutical compositions according to the present invention can further comprise a buffering component. The buffering component can comprise various buffering agents as will be understood by those skilled in the art. Exemplary buffering agents include, but are not limited to, inorganic acids (e.g., phosphoric acid), organic acids (e.g., citric acid), organic bases (e.g., tris-base (tris(hydroxymethyl)aminomethane), trolamine (triethanolamine), or histadine), and mixtures thereof. The buffering components can comprise an organic base, and can also comprise tris-base, trolamine, phosphate, or a mixture thereof. In some embodiments, the buffering component comprises an organic acid and an organic base, and can also comprise citric acid and tris-base, trolamine, phosphate, or a mixture thereof. The buffering agent can be present in an amount that will buffer the pharmaceutical composition against the acidic environment that may be experienced in the gut as will be understood by one skilled in the art.

In addition to the bile salt component and fatty acid component, or bile salt component alone, pharmaceutical compositions of the present invention can include various suitable excipients as will be understood by those skilled in the art, such as those found in the *National Formulary* 19, pages 2404–2406 (2000), the disclosure of pages 2404 to 2406 being incorporated herein in their entirety. For example, the pharmaceutical compositions can include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, and inert fillers can also be used. Examples of polyols include, but are not limited to, mannitol, sorbitol, xylitol, sucrose, maltose, glucose, lactose, dextrose, and the like. Other inert fillers which can be used encompass those which are known in the art and are useful in the manufacture of various dosage forms. If desired, the solid formulations can include other components such as bulking agents and/or granulating agents, and the like. The drug products of the invention can be formulated so as to provide quick, sustained, or delayed release of the active ingredient after administration to a subject by employing procedures well known in the art.

The pharmaceutical compositions according to the present invention include those suitable for oral, rectal, topical, inhalation (e.g., via an aerosol) buccal (e.g., sublingual), vaginal, parenteral (e.g., subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular drug-oligomer conjugate which is being used.

Pharmaceutical compositions suitable for oral administration can be presented in discrete units, such as capsules, cachets, lozenges, or tables, each containing a predetermined amount of the drug-oligomer conjugates; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the drug-oligomer conjugate, the fatty acid component, the bile salt component, and a suitable carrier (which can contain one or more accessory ingredients as noted above). In general, the pharmaceutical composition according to embodiments of the present invention are prepared by uniformly and intimately admixing the drug-oligomer conjugate, the fatty acid component, and the bile salt component with a liquid or finely divided solid carrier, or both, and then, if necessary, shaping the resulting mixture.

In some embodiments of the present invention, the pharmaceutical composition is a liquid pharmaceutical composition suitable for oral administration. When the pharmaceutical composition is a liquid pharmaceutical composition, the composition can include a buffering agent as described above. Liquid pharmaceutical compositions according to embodiments of the present invention have a pH that is physiologically compatible. Liquid pharmaceutical compositions according to embodiments of the present invention can have a pH that is between 6.2 and 9.0. In some embodiments, liquid pharmaceutical compositions according to embodiments of the present invention have a pH that is between a lower limit of 6.3, 6.4, 6.5, 6.6, 6.7, 6.8, 6.9, 7.0, 7.1, 7.2, 7.3, 7.4, 7.5, 7.6, or 7.7 and an upper limit of 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, or 8.9. In some embodiments, liquid pharmaceutical compositions according to embodiments of the present invention have a pH that is between 7.0 and 8.5. In other embodiments, liquid pharmaceutical compositions according to embodiments of the present invention have a pH that is between 7.4 and 8.2.

In other embodiments of the present invention, the pharmaceutical composition is a solid pharmaceutical composition suitable for oral administration. The solid pharmaceutical composition can be prepared by various methods as will be understood by those skilled in the art. For example, a tablet can be prepared by compressing or molding a powder or granules containing the drug-oligomer conjugate, the fatty acid component, the bile salt component, optionally with one or more accessory ingredients. Compressed tablets can be prepared by compressing, in a suitable machine, the mixture in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Pharmaceutical compositions suitable for buccal (sublingual) administration include lozenges comprising the drug and/or drug-oligomer conjugate, the fatty acid component, and the bile salt component, or the bile salt component alone in a flavored base, usually an artificial sweetener and acacia or tragacanth; and pastilles comprising the drug and/or drug-oligomer conjugate, the fatty acid component, and the bile salt component or bile salt component in an inert base such as gelatin and glycerin or sucrose and acacia.

Pharmaceutical compositions according to embodiments of the present invention suitable for parenteral administration comprise sterile aqueous and non-aqueous injection solutions comprising the drug and/or drug-oligomer conjugate, the fatty acid component, and the bile salt component or bile salt component, which preparations are preferably isotonic with the blood of the intended recipient. These preparations can contain anti-oxidants, buffers, bacteriostats and solutes which render the composition isotonic with the blood of the intended recipient. Aqueous and non-aqueous sterile suspensions can include suspending agents and thickening agents. The compositions can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, an injectable, stable, sterile composition comprising the drug and/or drug-oligomer conjugate, the fatty acid component and the bile salt component or the bile salt component without the fatty acid component in a unit dosage form in a sealed container can be provided. The mixture of the drug and/or drug-oligomer conjugate, the fatty acid component, and the bile salt component or the bile salt component is provided in the form of a lyophilizate which is capable of being reconstituted with a suitable pharmaceutically acceptable carrier to form a liquid composition suitable for injection thereof into a subject.

As used herein, a "pharmaceutically acceptable carrier" according to the present invention is a component such as a carrier, diluent, or excipient of a composition that is compatible with the other ingredients of the composition in that it can be combined with the compounds and/or compositions of the present invention without eliminating the biological activity of the compounds or the compositions, and is suitable for use in subjects as provided herein without undue adverse side effects (such as toxicity, irritation, allergic response, and death). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents.

The unit dosage form of the compositions of this invention can range from about 10 mg to about 10 grams of drug and/or drug-oligomer conjugate. When the drug and/or drug-oligomer conjugate is substantially water-insoluble, a sufficient amount of emulsifying agent which is physiologically acceptable can be employed in sufficient quantity to emulsify the drug and/or drug-oligomer conjugate in an aqueous carrier. One such useful emulsifying agent is phosphatidyl choline.

Pharmaceutical compositions suitable for rectal administration can be presented as unit dose suppositories. These can be prepared by admixing the drug and/or drug-oligomer conjugate, the fatty acid component, and the bile salt component or the bile salt component alone with one or more conventional solid carriers, for example, cocoa butter, and then shaping the resulting mixture.

Pharmaceutical compositions suitable for topical application to the skin can take the form of an ointment, cream, lotion, paste, gel, spray, aerosol, transdermal patch or oil. Carriers which can be used include petroleum jelly, lanoline, polyethylene glycols, alcohols, transdermal enhancers, and combinations of two or more thereof.

Pharmaceutical compositions suitable for transdermal administration can be presented as discrete patches adapted to remain in intimate contact with the epidermis of the recipient for a prolonged period of time. Compositions suitable for transdermal administration can also be delivered by iontophoresis (see, for example, *Pharmaceutical Research* 3 (6):318 (1986)) and typically take the form of an optionally buffered aqueous solution of the drug and/or drug-oligomer conjugate, the fatty acid component, and the bile salt component or the bile salt component without the fatty acid component. Suitable formulations comprise citrate or bis\tris buffer (pH 6) or ethanol/water and contain from 0.1 to 0.2M active ingredient.

Methods of treating a disorder in a subject in need of such treatment by administering a therapeutically effective amount of any of the various pharmaceutical compositions of the present invention are also provided. The effective amount of drug and/or of the drug-oligomer conjugate, the use of which is in the scope of present invention, will vary somewhat from drug to drug, conjugate to conjugate, and subject to subject, and will depend, for example, upon factors such as the age and condition of the subject, the severity of the condition to be treated and/or the route of delivery. An appropriate "therapeutically effective amount" in any individual case can be determined by one of ordinary skill in the art by reference to the pertinent texts and literature and/or by using routine experimentation. (See, for example, Remington, *The Science And Practice of Pharmacy* (9th Ed. 1995).

A subject of this invention can be any animal that is susceptible to any of the disorders as described herein and that would be able to be treated with the compositions of this invention. The subject can be any mammal and the mammal can be a human.

As an example, a dosage of from about 1.0 µg/kg to about 50 mg/kg, including any dosage range between these values, will have therapeutic efficacy, with all weights being calculated based upon the weight of the insulin and/or the insulin drug-oligomer conjugate. Toxicity concerns at the higher level can restrict intravenous dosages to a lower level such as up to about 10 mg/kg, with all weights being calculated based upon the weight of the active base. A dosage of from about 10 mg/kg to about 50 mg/kg can be employed for oral administration. Typically, a dosage of from about 0.5 mg/kg to 5 mg/kg can be employed for intramuscular injection. The frequency of administration can be, for example, one, two, three or more times per day or as necessary to control the condition. Control of the condition and efficacy of the treatment can be readily determined by those skilled in the art of studying and/or treating insulin deficiencies and/or related disorders. Alternatively, the pharmaceutical compositions of this invention can be administered by continuous infusion. The duration of treatment depends on the type of insulin deficiency being treated and can be for as long as the life of the subject.

Methods of treating a bone disorder in a subject in need of such treatment by administering a therapeutically effective amount of a pharmaceutical composition of this invention comprising calcitonin and/or a calcitonin drug-oligomer conjugate are also provided. The bone disorder can be characterized by excessive osteoclastic bone resorption and/or hypercalcemic serum effects, according to assays known in the art. Bone disorders that can be treated and/or prevented by methods of the present invention include, but are not limited to, osteoporosis, Paget's disease, and hypercalcemia.

The effective amount of the calcitonin and/or calcitonin drug-oligomer conjugate, the use of which is in the scope of present invention, will vary somewhat from drug to drug, conjugate to conjugate, and patient to patient, and will depend upon factors such as the age and condition of the patient and the route of delivery. Such dosages can be determined in accordance with routine pharmacological procedures known to those skilled in the art. As a general proposition, a dosage from about 1.0 µg/kg to about 50 mg/kg will have therapeutic efficacy, with all weights being calculated based upon the weight of the mixture of calcitonin and/or calcitonin drug-oligomer conjugates. Toxicity concerns at the higher level can restrict intravenous dosages to a lower level such as up to about 10 mg/kg, with all weights being calculated based upon the weight of the active base. A dosage from about 10 mg/kg to about 50 mg/kg can be employed for oral administration. The frequency of administration can be, for example, one, two, three or more times per day or as necessary to control the condition. Control of the condition and efficacy of the treatment can be readily determined by those skilled in the art of studying and/or treating insulin deficiencies and/or related disorders. Alternatively, the pharmaceutical compositions of this invention can be administered by continuous infusion. The duration of treatment depends on the type of insulin deficiency being treated and can be for as long as the life of the subject.

In another aspect of the present invention, a method of providing a pharmaceutical composition of this invention is provided herein, which comprises selecting an amount of a bile salt to include in the composition based on the ability of the bile salt to increase the solubility of a fatty acid component when the composition has a pH of 8.5 or less.

According to other embodiments of the present invention, a method of providing a pharmaceutical composition of this invention is provided herein, which comprises selecting an amount of a fatty acid to include in the composition based on the ability of the fatty acid to lower the precipitation point of a bile salt component in the composition to a pH of 5.5 or less.

According to still other embodiments of the present invention, a method of providing a pharmaceutical composition of this invention is provided herein, comprises selecting an amount of a fatty acid to include in the composition based on the ability of the fatty acid to alter the precipitation characteristics of a bile salt component in the composition.

The present invention will now be described with reference to the following examples. It should be appreciated that these examples are for the purposes of illustrating aspects of the present invention, and do not limit the scope of the invention as defined by the claims.

EXAMPLES

Example 1

Synthesis of 6-(2-{2-[2-(2-{2-[2-(2-methoxyethoxy) ethoxy]-ethoxy}-ethoxy)-ethoxy]-ethoxy}-ethoxy)-hexanoic acid 2,5-dioxo-pyrrolidin-1-yl ester (8)

Hexaethylene glycol monobenzyl ether (1). An aqueous sodium hydroxide solution prepared by dissolving 3.99 g (100 mmol) NaOH in 4 ml water was added slowly to monodispersed hexaethylene glycol (28.175 g, 25 ml, 100 mmol). Benzyl chloride (3.9 g, 30.8 mmol, 3.54 ml) was added and the reaction mixture was heated with stirring to 100° C. for 18 hours. The reaction mixture was then cooled, diluted with brine (250 ml) and extracted with methylene chloride (200 ml×2). The combined organic layers were washed with brine once, dried over $Na_2SO_4$, filtered and concentrated in vacuo to a dark brown oil. The crude product mixture was purified via flash chromatography (silica gel, gradient elution: ethyl acetate to 9/1 ethyl acetate/methanol) to yield 8.099 g (70%) of monodispersed compound 1 as a yellow oil.

Ethyl 6-methylsulfonyloxyhexanoate (2). A solution of monodispersed ethyl 6-hydroxyhexanoate (50.76 ml, 50.41 g, 227 mmol) in dry dichloromethane (75 ml) was chilled in an ice bath and placed under a nitrogen atmosphere. Triethylamine (34.43 ml, 24.99 g, 247 mmol) was added. A solution of methanesulfonyl chloride (19.15 ml, 28.3 g, 247 mmol) in dry dichloromethane (75 ml) was added dropwise from an addition funnel. The mixture was stirred for three and one half hours, slowly being allowed to come to room temperature as the ice bath melted. The mixture was filtered through silica gel, and the filtrate was washed successively with water, saturated $NaHCO_3$, water and brine. The organics were dried over $Na_2SO_4$, filtered and concentrated in vacuo to a pale yellow oil. Final purification of the crude product was achieved by flash chromatography (silica gel, 1/1 hexanes/ethyl acetate) to give the monodispersed compound 2 (46.13 g, 85%) as a clear, colorless oil. FAB MS: m/e 239 (M+H), 193 (M−$C_2H_5O$).

6-{2-[2-(2-{2-[2-(2-Benzyloxyethoxy)ethoxy]ethoxy}-ethoxy)-ethoxy]-ethoxy}-hexanoic acid ethyl ester (3). Sodium hydride (3.225 g or a 60% oil dispersion, 80.6 mmol) was suspended in 80 ml of anhydrous toluene, placed under a nitrogen atmosphere and cooled in an ice bath. A solution of the monodispersed alcohol 9 (27.3 g, 73.3 mmol) in 80 ml dry toluene was added to the NaH suspension. The mixture was stirred at 0° C. for thirty minutes, allowed to come to room temperature and stirred for another five hours, during which time the mixture became a clear brown solution. The monodispersed mesylate 10 (19.21 g, 80.6 mmol) in 80 ml dry toluene was added to the NaH/alcohol mixture, and the combined solutions were stirred at room temperature for three days. The reaction mixture was quenched with 50 ml methanol and filtered through basic alumina. The filtrate was concentrated in vacuo and purified by flash chromatography (silica gel, gradient elution: 3/1 ethyl acetate/hexanes to ethyl acetate) to yield the monodispersed compound 3 as a pale yellow oil (16.52 g, 44%). FAB MS: m/e 515 (M+H).

6-{2-[2-(2-{2-[2-(2-hydroxyethoxy)ethoxy]ethoxy}-ethoxy)-ethoxy]-ethoxy}-hexanoic acid ethyl ester (4). Substantially monodispersed benzyl ether 3 (1.03 g, 2.0 mmol) was dissolved in 25 ml ethanol. To this solution was added 270 mg 10% Pd/C, and the mixture was placed under a hydrogen atmosphere and stirred for four hours, at which time TLC showed the complete disappearance of the starting material. The reaction mixture was filtered through Celite 545 to remove the catalyst, and the filtrate was concentrated in vacuo to yield the monodispersed compound 4 as a clear oil (0.67 g, 79%). FAB MS: m/e 425 (M+H), 447 (M+Na).

6-{2-[2-(2-{2-[2-(2-methylsulfonylethoxy)ethoxy] ethoxy}-ethoxy)-ethoxy]-ethoxy}-hexanoic acid ethyl ester (5). The monodispersed alcohol 4 (0.835 g, 1.97 mmol) was dissolved in 3.5 ml dry dichloromethane and placed under a nitrogen atmosphere. Triethylamine (0.301 ml, 0.219 g, 2.16 mmol) was added and the mixture was chilled in an ice bath. After two minutes, the methanesulfonyl chloride (0.16 ml, 0.248 g, 2.16 mmol) was added. The mixture was stirred for 15 minutes at 0° C., then at room temperature for two hours. The reaction mixture was filtered through silica gel to remove the triethylammonium chloride, and the filtrate was washed successively with water, saturated $NaHCO_3$, water and brine. The organics were dried over $Na_2SO_4$, filtered and concentrated in vacuo. The residue was purified by column chromatography (silica gel, 9/1 ethyl acetate/methanol) to give monodispersed compound 5 as a clear oil (0.819 g, 83%). FAB MS: m/e 503 (M+H).

6-(2-{2-[2-(2-{2-[2-(2-methoxyethoxy)ethoxy]-ethoxy}-ethoxy)-ethoxy]-ethoxy}-ethoxy)-hexanoic acid ethyl ester (6). NaH (88 mg of a 60% dispersion in oil, 2.2 mmol) was suspended in anhydrous toluene (3 ml) under $N_2$ and chilled to 0° C. Monodispersed diethylene glycol monomethyl ether (0.26 ml, 0.26 g, 2.2 mmol) that had been dried via azeotropic distillation with toluene was added. The reaction mixture was allowed to warm to room temperature and stirred for four hours, during which time the cloudy grey suspension became clear and yellow and then turned brown. Mesylate 5 (0.50 g, 1.0 mmol) in 2.5 ml dry toluene was added. After stirring at room temperature over night, the reaction was quenched by the addition of 2 ml of methanol and the resultant solution was filtered through silica gel. The filtrate was concentrated in vacuo and the FAB MS: m/e 499 (M+H), 521 (M+Na). Additional purification by preparatory chromatography (silica gel, 19/3 chloroform/methanol) provided the monodispersed compound 6 as a clear yellow oil (0.302 g 57%). FAB MS: m/e 527 (M+H), 549 (M+Na).

6-(2-{2-[2-(2-{2-[2-(2-methoxyethoxy)ethoxy]-ethoxy}-ethoxy)-ethoxy]-ethoxy}-ethoxy)-hexanoic acid (7). Monodispersed ester 6 (0.25 g, 0.46 mmol) was stirred for 18 hours in 0.71 ml of 1 N NaOH. After 18 hours, the mixture was concentrated in vacuo to remove the alcohol and the residue dissolved in a further 10 ml of water. The aqueous solution was acidified to pH 2 with 2 N HCl and the product was extracted into dichloromethane (30 ml×2). The combined organics were then washed with brine (25 ml× 2), dried over $Na_2SO_4$, filtered and concentrated in vacuo to yield the monodispersed compound 15 as a yellow oil (0.147 g, 62%). FAB MS: m/e 499 (M+H), 521 (M+Na).

6-(2-{2-[2-(2-{2-[2-(2-methoxyethoxy)ethoxy]-ethoxy}-ethoxy)-ethoxy]-ethoxy}-ethoxy)-hexanoic acid 2,5-dioxo-pyrrolidin-1-yl ester (8). Monodispersed acid 7 (0.209 g, 0.42 mmol) was dissolved in 4 ml of dry dichloromethane and added to a dry flask already containing NHS (N-hydroxysuccinimide) (57.8 mg, 0.502 mmol) and EDC (1-(3-dimethylaminopropyl)-3-ethylcarbodiimide hydrochloride) (98.0 mg, 0.502 mmol) under a $N_2$ atmosphere. The solution was stirred at room temperature overnight and filtered through silica gel to remove excess reagents and the urea formed from the EDC. The filtrate was concentrated in vacuo to provide the activated monodispersed oligomer 8 as a dark yellow oil (0.235 g, 94%). FAB MS: m/e 596 (M+H), 618 (M+Na).

Example 2

Synthesis of Activated MPEG$_7$-C$_8$ (14)

Mesylate of triethylene glycol monomethyl ether (9). To a solution of CH$_2$Cl$_2$ (100 mL) cooled to 0° C. in an ice bath was added monodispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL CH$_2$Cl$_2$). The reaction mixture was stirred for 30 min at 0° C., allowed to warm to room temperature, and then stirred for 2 h. The crude reaction mixture was filtered through Celite (washed CH$_2$Cl$_2$~200 mL), then washed with H$_2$O (300 mL), 5% NaHCO$_3$ (300 mL), H$_2$O (300 mL), sat. NaCl (300 mL), dried MgSO$_4$, and evaporated to dryness. The oil was then placed on a vacuum line for ~2h to ensure dryness and afforded the monodispersed compound 9 as a yellow oil (29.15 g, 80% yield).

Heptaethylene glycol monomethyl ether (10). To a solution of monodispersed tetraethylene glycol (51.5 g, 0.27 mol) in THF (1 L) was added potassium t-butoxide (14.8 g, 0.13 mol, small portions over ~30 min). The reaction mixture was then stirred for 1 h and then 9 (29.15 g, 0.12 mol) dissolved in THF (90 mL) was added dropwise and the reaction mixture was stirred overnight. The crude reaction mixture was filtered through Celite (washed CH$_2$Cl$_2$, ~200 mL) and evaporated to dryness. The oil was then dissolved in HCl (250 mL, 1 N) and washed with ethyl acetate (250 mL) to remove excess 9. Additional washings of ethyl acetate (125 mL) may be required to remove remaining 9. The aqueous phase was washed repetitively with CH$_2$Cl$_2$ (125 mL volumes) until most of the compound 18 has been removed from the aqueous phase. The first extraction will contain 9, 10, and dicoupled side product and should be back extracted with HCl (125 mL, 1N). The organic layers were combined and evaporated to dryness. The resultant oil was then dissolved in CH$_2$Cl$_2$ (100 mL) and washed repetitively with H$_2$O (50 mL volumes) until 10 was removed. The aqueous fractions were combined, total volume 500 mL, and NaCl was added until the solution became cloudy and then was washed with CH$_2$Cl$_2$ (2×500 mL). The organic layers were combined, dried MgSO$_4$, and evaporated to dryness to afford the monodispersed compound 10 as an oil (16.9 g, 41% yield). It may be desirable to repeat one or more steps of the purification procedure to ensure high purity.

8-Bromooctanoate (11). To a solution of monodispersed 8-bromooctanoic acid (5.0 g, 22 mmol) in ethanol (100 mL) was added H$_2$SO$_4$ (0.36 mL, 7.5 mmol) and the reaction was heated to reflux with stirring for 3 h. The crude reaction mixture was cooled to room temperature and washed H$_2$O (100 mL), sat. NaHCO$_3$ (2×100 mL), H$_2$O (100 mL), dried MgSO$_4$, and evaporated to dryness to afford a clear oil 11 (5.5 g, 98% yield).

MPEG$_7$-C$_8$ ester (12). To a solution of the monodispersed compound 10 (3.0 g, 8.8 mmol) in ether (90 mL) was added potassium t-butoxide (1.2 g, 9.6 mmol) and the reaction mixture was stirred for 1 h. Then dropwise addition of the monodispersed compound 11 (2.4 g, 9.6 mmol), dissolved in ether (10 mL), was added and the reaction mixture was stirred overnight. The crude reaction mixture was filtered through Celite (washed CH$_2$Cl$_2$, ~200 mL) and evaporated to dryness. The resultant oil was dissolved in ethyl acetate and washed H$_2$O (2×200 mL), dried MgSO$_4$, and evaporated to dryness. Column chromatography (Silica, ethyl acetate to ethyl acetate/methanol, 10:1) was performed and afforded the monodispersed compound 12 as a clear oil (0.843 g, 19% yield).

MPEG$_7$-C$_8$ acid (13). To the oil of the monodispersed compound 12 (0.70 g, 1.4 mmol) was added 1N NaOH (2.0 mL) and the reaction mixture was stirred for 4 h. The crude reaction mixture was concentrated, acidified (pH~2), saturated with NaCl, and washed CH$_2$Cl$_2$ (2×50 mL). The organic layers were combined, washed sat. NaCl, dried MgSO$_4$, and evaporated to dryness to afford the monodispersed compound 13 as a clear oil (0.35 g, 53% yield).

Activation of MPEG$_7$-C$_8$ acid. Monodispersed mPEG7-C8-acid 13 (0.31 g, 0.64 mmol) was dissolved in 3 ml of anhydrous methylene chloride and then solution of N-hydroxysuccinimide (0.079 g, 0.69 mmol) and EDCl.HCl (135.6 mg, 0.71 mmol) in anhydrous methylene chloride added. Reaction was stirred for several hours, then washed with 1N HCl, water, dried over MgSO$_4$, filtered and concentrated. Crude material was purified by column chromatography, concentrated to afford monodispersed activated MPEG$_7$-C$_8$ 14 as a clear oil and dried via vacuum.

Example 3

Synthesis of Activated MPEG$_7$-C$_{10}$ (19)

10-hydroxydecanoate (15). To a solution of monodispersed 10-hydroxydecanoic acid (5.0 g, 26.5 mmol) in ethanol (100 mL) was added H$_2$SO$_4$ (0.43 mL, 8.8 mmol) and the reaction was heated to reflux with stirring for 3 h. The crude reaction mixture was cooled to room temperature and washed H$_2$O (100 mL), sat. NaHCO$_3$ (2×100 mL), H$_2$O (100 mL), dried MgSO$_4$, and evaporated to dryness to afford the monodispersed compound 15 as a clear oil (6.9 g, 98% yield).

Mesylate of 10-hydroxydecanoate (16). To a solution of CH$_2$Cl$_2$ (27 mL) was added monodispersed 10-hydroxydecanoate 15 (5.6 g, 26 mmol) and cooled to 0° C. in an ice bath. Then triethylamine (5 mL, 37 mmol) was added and the reaction mixture was stirred for 15 min at 0° C. Then methanesulfonyl chloride (2.7 mL, 24 mmol) dissolved in CH$_2$Cl$_2$ (3 mL) was added and the reaction mixture was stirred at 0° C. for 30 min, the ice bath was removed and the reaction was stirred for an additional 2 h at room temperature. The crude reaction mixture was filtered through Celite (washed CH$_2$Cl$_2$, 80 mL) and the filtrate was washed H$_2$O (100 mL), 5% NaHCO$_3$ (2×100 mL), H$_2$O (100 mL), sat. NaCl (100 mL), dried MgSO$_4$, and evaporated to dryness to afford the monodispersed compound 16 as a yellowish oil (7.42 g, 97% yield).

MPEG$_7$-C$_{10}$ Ester (17). To a solution of substantially monodispersed heptaethylene glycol monomethyl ether 10 (2.5 g, 7.3 mmol) in tetrahydrofuran (100 mL) was added sodium hydride (0.194 g, 8.1 mmol) and the reaction mixture was stirred for 1 h. Then dropwise addition of mesylate of monodispersed 10-hydroxydecanoate 16 (2.4 g, 8.1 mmol), dissolved in tetrahydrofuran (10 mL), was added and the reaction mixture was stirred overnight. The crude reaction mixture was filtered through Celite (washed CH$_2$Cl$_2$, ~200 mL) and evaporated to dryness. The resultant oil was dissolved in ethyl acetate and washed H$_2$O (2×200 mL), dried MgSO$_4$, evaporated to dryness, chromatographed (silica, ethyl acetate/methanol, 10:1), and chromatographed (silica, ethyl acetate) to afford the monodispersed compound 17 as a clear oil (0.570 g, 15% yield).

MPEG$_7$-C$_{10}$ Acid (18). To the oil of the monodispersed mPEG$_7$-C$_{10}$ ester 17 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the monodispersed compound 18 as a clear oil (0.340 g, 62% yield).

Activation of $MPEG_7$-$C_{10}$ Acid. The monodispersed acid 18 was activated using procedures as described herein to provide activated $MPEG_7$-$C_{10}$ Oligomer 19.

Example 4

Synthesis of Activated $C_{18}(PEG_6)$ Oliomer (22)

Synthesis of $C_{18}(PEG_6)$ Oligomer (20). Monodispersed stearoyl chloride (0.7 g, 2.31 mmol) was added slowly to a mixture of monodispersed $PEG_6$ (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over $MgSO_4$, concentrated and dried via vacuum. Purified monodispersed compound 20 was analyzed by FABMS: m/e 549/$M^+H$.

Activation of $C_{18}(PEG_6)$ Oligomer. Activation of monodispersed $C_{18}(PEG_6)$ oligomer was accomplished in two steps:

1) Monodispersed stearoyl-$PEG_6$ 20 (0.8 g, 1.46 mmol) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining substantially monodispersed stearoyl PEG6 chloroformate 21 was dried over $P_2O_5$ overnight.

2) To a solution of monodispersed stearoyl-$PEG_6$ chloroformate 21 (0.78 g, 1.27 mmol) and TEA (128 mg, 1.27 mmol) in anhydrous methylene chloride, N-hydroxy succinimide (NHS) solution in methylene chloride was added. The reaction mixture was stirred for 16 hours, then washed with water, dried over $MgSO_4$, filtered, concentrated and dried via vacuum to provide the monodispersed activated $C_{18}(PEG_6)$ oligomer 22.

Example 5

Synthesis of Activated $C_{18}(PEG_8)$ Oligomer (28)

Tetraethylene glycol monobenzylether (23). To the oil of monodispersed tetraethylene glycol (19.4 g, 0.10 mol) was added a solution of NaOH (4.0 g in 4.0 mL) and the reaction was stirred for 15 mm. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed $CH_2Cl_2$ (2×200 mL). The organic layers were combined, washed sat. NaCl, dried $MgSO_4$, and chromatographed (silica, ethyl acetate) to afford the monodispersed compound 23 as a yellow oil (6.21 g, 71% yield).

Mesylate of tetraethylene glycol monobenzylether (24). To a solution of $CH_2Cl_2$ (20 mL) was added monodispersed tetraethylene glycol monobenzylether 23 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in $CH_2Cl_2$ (2 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), and dried $MgSO_4$. The resulting yellow oil was chromatographed on a pad of silica containing activated carbon (10 g) to afford the monodispersed compound 24 as a clear oil (7.10 g, 89% yield).

Octaethylene glycol monobenzylether (25). To a solution of tetrahydrofuran (140 mL) containing sodium hydride (0.43 g, 18 mmol) was added dropwise a solution of monodispersed tetraethylene glycol (3.5 g, 18 mmol) in tetrahydrofuran (10 mL) and the reaction mixture was stirred for 1 h. Then mesylate of monodispersed tetraethylene glycol monobenzylether 24 (6.0 g, 16.5 mmol) dissolved in tetrahydrofuran (10 mL) was added dropwise and the reaction mixture was stirred overnight. The crude reaction mixture was filtered through Celite (washed, $CH_2Cl_2$, 250 mL) and the filtrate was washed $H_2O$, dried $MgSO_4$, and evaporated to dryness. The resultant oil was chromatographed (silica, ethyl acetate/methanol, 10:1) and chromatographed (silica, chloroform/methanol, 25:1) to afford the monodispersed compound 25 as a clear oil (2.62 g, 34% yield).

Synthesis of Stearate $PEG_8$-Benzyl (26). To a stirred cooled solution of monodispersed octaethylene glycol monobenzylether 25 (0.998 g, 2.07 mmol) and pyridine (163.9 mg, 2.07 mmol) was added monodispersed stearoyl chloride (627.7 mg, 2.07 mmol) in benzene. The reaction mixture was stirred overnight (18 hours). The next day the reaction mixture was washed with water, dried over $MgSO_4$, concentrated and dried via vacuum. Then the crude product was chromatographed on flash silica gel column, using 10% methanol/90% chloroform. The fractions containing the product were combined, concentrated and dried via vacuum to afford the monodispersed compound 26.

Hydrogenolysis of Stearate-$PEG_8$-Benzyl. To a methanol solution of monodispersed stearate-$PEG_8$-Bzl 26 (0.854 g 1.138 mmol) Pd/C(10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with $R_f$=0.6 collected, concentrated and dried to provide the monodispersed acid 27.

Activation of $C_{18}(PEG_8)$ Oligomer. Two step activation of monodispersed stearate-PEG8 oligomer 27 was performed as described for stearate-$PEG_6$ as described herein to provide the monodispersed activated $C_{18}(PEG_8)$ oligomer 28.

Example 6

Synthesis of Activated Triethylene Glycol Monomethyl Oligomers

A solution of toluene containing 20% phosgene (100 ml, approximately 18.7 g, 189 mmol phosgene) was chilled to 0° C. under a $N_2$ atmosphere. Monodispersed mTEG (triethylene glycol, monomethyl ether, 7.8 g, 47.5 mmol) was dissolved in 25 mL anhydrous ethyl acetate and added to the chilled phosgene solution. The mixture was stirred for one hour at 0° C., then allowed to warm to room temperature and stirred for another two and one half hours. The remaining phosgene, ethyl acetate and toluene were removed via vacuum distillation to leave the monodispersed mTEG chloroformate as a clear oily residue.

The monodispersed nTEG chloroformate was dissolved in 50 mL of dry dichloromethane to which was added TEA (triethyleamine, 6.62 mL, 47.5 mmol) and NHS (N-hydroxysuccinimide, 5.8 g, 50.4 mmol). The mixture was stirred at room temperature under a dry atmosphere for twenty hours during which time a large amount of white precipitate appeared. The mixture was filtered to remove this precipitate and concentrated in vacuo. The resultant oil was taken up in dichloromethane and washed twice with cold deionized water, twice with 1N HCl and once with brine. The organics were dried over $MgSO_4$, filtered and concentrated to provide the monodispersed title compound as a clear, light yellow oil. If necessary, the NHS ester could be further purified by flash chromatography on silica gel using EtOAc as the elutant.

Example 7

Synthesis of Activated Palmitate-TEG Oligomers

Monodispersed palmitic anhydride (5 g; 10 mmol) was dissolved in dry THF (20 mL) and stirred at room temperature. To the stirring solution, 3 mol excess of pyridine was added followed by monodispersed triethylene glycol (1.4 mL). The reaction mixture was stirred for 1 hour (progress of the reaction was monitored by TLC; ethyl acetate-chloroform; 3:7). At the end of the reaction, THF was removed and the product was mixed with 10% $H_2SO_4$ acid and extracted ethyl acetate (3×30 mL). The combined extract was washed sequentially with water, brine, dried over $MgSO_4$, and evaporated to give monodispersed palmitate-TEG oligomers.

A solution of N,N'-disuccinimidyl carbonate (3 mmol) in DMF (~10 mL) is added to a solution of the monodispersed palmitate-TEG oligomers (1 mmol) in 10 mL of anhydrous DMF while stirring. Sodium hydride (3 mmol) is added slowly to the reaction mixture. The reaction mixture is stirred for several hours (e.g., 5 hours). Diethyl ether is added to precipitate the monodispersed activated title oligomer. This process is repeated 3 times and the product is finally dried.

Example 8

Synthesis of Activated Hexaethylene Glycol Monomethyl Oligomers

Monodispersed activated hexaethylene glycol monomethyl ether was prepared analogously to that of monodispersed triethylene glycol as described herein. A 20% phosgene in toluene solution (35 mL, 6.66 g, 67.4 mmol phosgene) was chilled under a $N_2$ atmosphere in an ice/salt water bath. Monodispersed hexaethylene glycol (1.85 mL, 2.0 g, 6.74 mmol) was dissolved in 5 mL anhydrous EtOAc and added to the phosgene solution via syringe. The reaction mixture was kept stirring in the ice bath for one hour, removed and stirred a further 2.5 hours at room temperature. The phosgene, EtOAc, and toluene were removed by vacuum distillation, leaving monodispersed methyl hexaethylene glycol chloroformate as a clear, oily residue.

The monodispersed chloroformate was dissolved in 20 mL dry dichloromethane and placed under a dry, inert atmosphere. Triethylamine (0.94 mL, 0.68 g, 6.7 mmol) and then NHS (N-hydroxy succinimide, 0.82 g, 7.1 mmol) were added, and the reaction mixture was stirred at room temperature for 18 hours. The mixture was filtered through silica gel to remove the white precipitate and concentrated in vacuo. The residue was taken up in dichloromethane and washed twice with cold water, twice with 1 N HCl and once with brine. The organics were dried over $Na_2SO_4$, filtered and concentrated. Final purification was done via flash chromatography (silica gel, EtOAc) to obtain the activated monodispersed hexaethylene monomethyl ether.

Example 9

Synthesis of Activated Heptaethylene Glycol Monomethyl Ether

8-Methoxy-1-(methylsulfonyl)oxy-3,6-dioxaoctane (29). A solution of monodispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC ($CHCl_3$ with 15% MeOH as the elutant) showed no remaining triethylene glycol monomethyl ether.

The reaction mixture was diluted with another 75 mL of dichloromethane and washed successively with saturated $NaHCO_3$, water and brine. The organics were dried over $Na_2SO_4$, filtered and concentrated in vacuo to give a monodispersed mixture of compounds 29 as a clear oil (5.31 g, 86%).

Heptaethylene glycol mono methyl ether (30). To a stirred solution of monodispersed tetraethylene glycol (35.7 mmol) in dry DMF (25.7 mL), under $N_2$ was added in portion a 60% dispersion of NaH in mineral oil, and the mixture was stirred at room temperature for 1 hour. To the resulting sodium salt of the tetraethylene glycol was added a solution of monodispersed mesylate 29 (23.36) in dry DMF (4 ml) in a single portion, and the mixture was stirred at room temperature for 3.5 hours. Progress of the reaction was monitored by TLC (12% $CH_3OH$—$CHCl_3$). The reaction mixture was diluted with an equal amount of 1N HCl, and extracted with ethyl acetate (2×20 ml) and discarded. Extraction of aqueous solution and work-up gave monodispersed heptaethylene glycol monomethyl ether 30 (82–84% yield). Oil; Rf 0.46 (methanol:chloroform=3:22); MS m/z calc'd for $C_{15}H_{32}O_8$ 340.21 ($M^+$+1), found 341.2.

Activation of heptaethylene glycol monomethyl ether. Monodispersed heptaethylene glycol monomethyl ether 30 is activated by a procedure as described herein to activate triethylene glycol monomethyl ether to provide the activated heptaethylene glycol monomethyl ether.

Example 10

Synthesis of Activated Decaethylene Glycol Monomethyl Ether (33)

20-methoxy-1-(methylsulfonyl)oxy-3,6,9,12,15,18-hexaoxaeicosane (31). Monodispersed compound 31 was obtained in quantitative yield from compound 30 and methanesulfonyl chloride as described for 29 in Example 9 above, as an oil; Rf 0.4 (ethyl acetate:acetonitrile=1:5); MS m/z calc'd for $C_{17}H_{37}O_{10}$ 433.21 ($M^+$+1), found 433.469.

Decaethylene glycol monomethyl ether (32). Monodispersed compound 32 was prepared from compound 31 and monodispersed triethylene glycol using the procedure described above in Example 17. Oil; Rf 0.41 (methanol:chloroform=6:10); MS m/z calc'd for $C_{21}H_{44}O_{11}$ 472.29 ($M^{+}+1$), found 472.29.

Activation of decaethylene glycol mono methyl ether. Monodispersed decaethylene glycol monomethyl ether 32 is activated by a procedure as described above to activate triethylene glycol monomethyl ether to provide the activated decaethylene glycol monomethyl ether 33.

Example 11

HIM2 Oral Liquid Process

A general procedure to manufacture an oral liquid pharmaceutical composition of the present invention is shown below: The process involves making a premix without the drug, filtering the premix, then adding the premix and drug solution together.

Quantitative Composition of HIM2 Oral Liquid, 6 mg/mL

| Excipient | Composition % w/v | mg/mL | Quantity per Batch (g) |
|---|---|---|---|
| HIM2 | 0.6 | 6 | 6.0[1] |
| Sodium Cholate | 3.0 | 30 | 30.0 |
| Oleic Acid, NF | 1.0 | 10 | 10.0 |
| Sucralose, 25% | 0.8 | 8 | 8.0 |
| Strawberry Flavor | 0.4 | 4 | 4.0 |
| Capric Acid | 0.5 | 5 | 5.0 |
| Lauric Acid | 0.5 | 5 | 5.0 |
| Citric Acid Anhydrous, USP | 6.72 | 67.2 | 67.2 |
| Trolamine, NF | 5.22 | 52.2 | 52.2 |
| Tromethamine, USP | 4.24 | 42.4 | 42.4 |
| Sodium Hydroxide, NF | 1.88 | 18.8 | 18.8 |
| Sodium Hydroxide, 5 N | QS | QS | QS |
| Hydrochloric Acid, 5N | QS | QS | QS |
| Sterile Water for Irrigation, USP | QS | QS | QS |
| Total | 100% | 1.0 mL | 1077.4 g |

[1]Weight adjusted for protein content.

Preparation of Premix for HIM2 Oral Liquid
1. Add 94.3% of the tromethamine and the trolamine, citric acid and sodium hydroxide (NF) to 350 g sterile water for irrigation and stir until completely dissolved.
2. Moderately heat and maintain the temperature through steps 3 & 4, below.
3. Add the sodium cholate to step 2 and stir until dissolved.
4. Add the oleic acid, capric acid, lauric acid, sucralose solution and strawberry flavor to step 3 and stir until dissolved.
5. Adjust the temperature to approximately room temperature.
6. Adjust the pH of step 5. if necessary, to 7.8±0.1 using 5N Sodium Hydroxide or 5N hydrochloric acid.
7. QS to the pre-mix batch weight with sterile water for irrigation.
8. Filter the step 7 product.

Preparation of HIM2 Oral Liquid, 6 mg/mL
1. Dispense the required quantity of the Premix for HIM2 Oral Liquid and continue stirring while performing steps 2 through 4 below.
2. Add the remaining tromethamine to 140 g of the sterile water for irrigation and stir until dissolved.
3. Adjust the pH of step 2, if necessary, to 7.7±0.2 using 5N sodium hydroxide or 5N hydrochloric acid.
4. Filter the step 3 liquid.
5. Add all of the HIM2 to step 4.and stir until completely dissolved.
6. Add all of step 5 to step 1 and stir.
7. Adjust the temperature to approximately room temperature, if necessary
8. Adjust the pH of step 7, if necessary, to 7.6–7.9 using 5N sodium hydroxide or 5N hydrochloric acid.

Example 12

HIM2 Oral Tablet Process

A general procedure to manufacture an oral tablet formulation of the present invention is shown below: The process involves making a lyophilized powder, adding tableting excipients and compressing.

Quantitative Composition of HIM2 Oral Tablets, 10 mg

| Excipient Lyo Portion | Quantity per Batch (g) |
|---|---|
| HIM2 | 2.50[1] |
| Sodium Cholate | 30.0 |
| Oleic Acid, NF | 10.0 |
| Sucralose, 25% | 8.0 |
| Strawberry Flavor | 4.0 |
| Capric Acid | 5.0 |
| Lauric Acid | 5.0 |
| Citric Acid Anhydrous, USP | 67.2 |
| Trolamine, NF | 52.2 |
| Tromethamine, USP | 42.4 |
| Sodium Hydroxide, NF | 18.8 |
| Sodium Hydroxide, 5 N | QS |
| Hydrochloric Acid, 5N | QS |
| Sterile Water for Irrigation, USP | QS |
| Total | 1077.4 g |
| Tablet Portion | |
| Lyo Portion | 127.6 |
| Citric Acid | 29.7 |
| Sodium Citrate dihydrate | 84.2 |
| Tris Base (tris(hydroxymethyl)aminomethane) | 106.7 |
| Microcrystilline Cellulose | 24.8 |
| Explotab | 9.4 |
| Total | 382.3 |

[1]Weight adjusted for protein content.

Procedure:
1. Dispense the required ingredients with the exception of the Sterile Water for Irrigation, USP,
2. Dispense 1500 g of Sterile Water for Irrigation, USP, and add to the processing vessel above.
3. Add the following ingredients to step 2 and mix until dissolved completely:
    a. all of the Sodium Cholate
    b. all of the Dibasic Sodium Phosphate Heptahydrate, USP
4. Add the following ingredients to step 3 and mix vigorously.
    a. All of the Gapric Acid
    b. All of the Lauric Acid
    c. All of the Sodium Hydroxide, NF (Note: Heat will be generated by the addition of Sodium Hydroxide, NF.)
5. Adjust the step 4 solution to a temperature between 45° C. and 50° C., and mix until a clear solution results.

6. Cool to room temperature and, if necessary, adjust the step 5 pH to 7.2–7.8 using Sodium Hydroxide, 1N, or Hydrochloric Acid, 1N.
7. Add all of the HIM2 PEG 7 to step 6 and mix vigorously until a clear solution results.
8. Determine the amount of additional Sterile Water for Irrigation, USP, to add (if necessary)
9. Lyophilize this solution until a white amorphous powder results.
10. Blend the lyo portion with the tableting excipients.
11. Compress on a tablet press to achieve desired size, shape and hardness.

Example 13

Calcitonin-Oligomer Conjugate Oral Liquid Process

A general procedure to manufacture an oral liquid pharmaceutical composition of the present invention is shown below: The process involves making a premix without the drug, filtering the premix, then adding the premix and drug solution together.

Quantitative Composition of CT-025 Oral Liquid, 25 ug/mL

| Ingredient | Concentration (% w/w) | Concentration (mg/mL) |
|---|---|---|
| Modified calcitonin as protein | 0.00242 | 0.025 |
| Capric acid | 1.72 | 17.8 |
| Lauric acid | 2.00 | 20.7 |
| Sodium hydroxide, NF | 0.77 | 7.96 |
| Sodium cholate | 4.30 | 44.4 |
| Sucralose solution, 25% liquid concentrate | 2.00 | 20.7 |
| Strawberry flavor No. 45056 | 0.500 | 5.17 |
| Sodium chloride, USP | 0.200 | 2.07 |
| Sodium phosphate, monobasic, monohydrate, USP | 0.460 | 4.76 |
| Sodium phosphate, dibasic, heptahydrate, USP | 4.92 | 50.9 |
| Sterile water for irrigation, USP | qs to 100% | qs to 1 mL |

* CT-025 amount (25 µg/mL) is adjusted based on salmon calcitonin equivalents

CT-025 Oral Liquid Process

Method of Manufacture of Concentrated Base Solution
1. Place sterile water for irrigation, USP (80% of batch amount) in a stainless steel container.
2. Add the buffer components, sodium phosphate monobasic and dibasic, to the water and mix to dissolve.
3. Add the sodium cholate to the solution in step 2 and mix to dissolve.
4. Add the sodium hydroxide pellets, NF to the solution in step 3 and mix to dissolve. Adjust the temperature to 55–60° C. before proceeding to next step.
5. Add the fatty acids, capric acid and lauric acid, to the solution in step 4 and maintain the temperature at 55–60° C. until ingredients are completely dissolved. Then adjust the temperature of the liquid to 23–27° C.
6. Add the taste masking ingredients: sucralose, strawberry flavor, and sodium chloride, to the solution in step 6. Mix to dissolve.
7. QS with sterile water for irrigation.
8. Filter solution through a 5-micron filter to remove any particulate matter.
9. Keep the base solution in a sealed container until ready for use to make the final oral liquid formulation.

Manufacture of CT-025 Oral liquid
10. Place portion of base solution in a stainless steel container. Start mixing and continue mixing throughout processing.
11. Dispense sterile water for irrigation in a separate container. Add the amount of CT-025 required based upon protein content value to the water and mix to dissolve.
12. Add CT-025 solution in step 11 to base solution in step 10. Rinse container with sterile water and add rinse to solution provided in step 12.
13. QS with sterile water for irrigation.

Example 14

Calcitonin-Oligomer Conjugate Oral Tablet Process

A general procedure to manufacture an oral tablet formulation of the present invention is shown below: The process involves making a lyophilized powder, adding tableting excipients and compressing.

Quantitative Composition of CT-025 Oral Tablets, 53 to 320 ug/tab

| Ingredient | % w/w |
|---|---|
| Modified calcitonin as Protein | 0.006–0.036 |
| Milled Powder Blend* | 50.3 |
| Mannitol | 34.6 |
| Croscarmellose sodium | 10.1 |
| Sorbitol | 5.03 |
| Sodium Stearyl Fumarate | 0.50 |
| Sorbitol | |

*composed of sodium cholate, sodium caprate and sodium laurate

CT-025 Oral Tablets Process.
1. Weigh out and dispense mannitol, sorbitol, and croscarmellose sodium in sufficient quantities to produce blend for all four of the development batches.
2. Pass the mannitol, sorbitol, and croscarmellose sodium through a #10 screen and layer the excipients in both arms of a 32 quart V-blender, alternating part of the Jet Milled Penetration Enhancer Blend with another excipient.
3. Blend for approximately 10 minutes.
4. Discharge the blend into a tared container lined with a LDPE bag and label as "Bulk Blend of Excipients".
5. Divide the blend into four equal parts by weighing out the blend into a tared container lined with a LDPE bag.

Wet Granulation (Prepared as Two Sublots A and B):

Preparation of Each Sublot
6. Weigh 626.85 g of the "Bulk Blend of Excipients" and transfer into the key granulator.
7. Weigh half the required amount of CT-025* for the first sublot and transfer into a clean glass container.
   * Note: The CT-025 is removed from the freezer and left "as is" at ambient conditions for approximately 1 hour. The CT-025 is equilibrated by removing the lid of the bottle for at least 2 hours prior to weighing.
8. Pipette out 45 mL of 1% acetic acid solution into the glass container. Dissolve the CT-025 by swirling gently from side to side.

9. Start the granulation and add the CT-025 solution as the granulating fluid using a 60-cc syringe with a needle.
10. Add more 1% acetic acid solution as needed using a 10-cc syringe with needle.
11. Transfer the wet granules from the granulator into a LDPE bag.

Wet Granulation (Prepared as Two Sublots A and B), Continued:

Preparation of Each Sublot
12. Layer a tray with aluminum foil and spread the wet granules evenly on the foil. Put into the oven previously set at 37° C.
13. Repeat steps 6–12 for second sublot.

Drying:
14. Dry granules in an oven at 37° C. for approximately 16–24 hours. Determine Loss On Drying. Each sublot is dried separately. Target moisture content is <3% upon removal from the oven.

Milling:
15. The dry granules of each sublot are passed through a #10 or #12 sieve.
16. The coarse granules retained are passed through a Quadro Comil equipped with a 0.125" screen.
17. Mix the sublots after the milling.
18. Weigh the total amount of granules collected.

Blending of Lubricant:
19. Load a 8 quart V-blender with granules from sublot A and B. Blend for approximately 5 minutes.
20. Weigh the required amount of sodium stearyl fumarate.
21. Remove one scoop of the granulation from each arm of the blender into a LDPE bag.
22. Add the sodium stearyl fumarate to the granules in the blender divided into both arms. Replace the granulation scooped out covering the sodium stearyl fumarate. Blend for approximately 2 minutes.
23. Discharge the final blend into a tared container lined with a LDPE bag. Sample final blend from various locations in the bag. Double bag the final blend for storage and label according to the sample label.

Tableting:
24. Use a single station press with caplet tooling to produce target weight per tablet of 900 mg (±5%, 855–945 mg).

Example 15

Liquid oral pharmaceutical compositions formulated as described herein were administered to healthy human volunteers in a 4-way crossover study both pre-prandial and post-prandial. The insulin conjugate HIM2 was provided at concentrations of 0.125. 0.25 and 0.5 mg/ml and these were compared to baseline values where no dosing occurred. 20 mL oral doses were provided followed by 70 mL of water.

Figure 2:
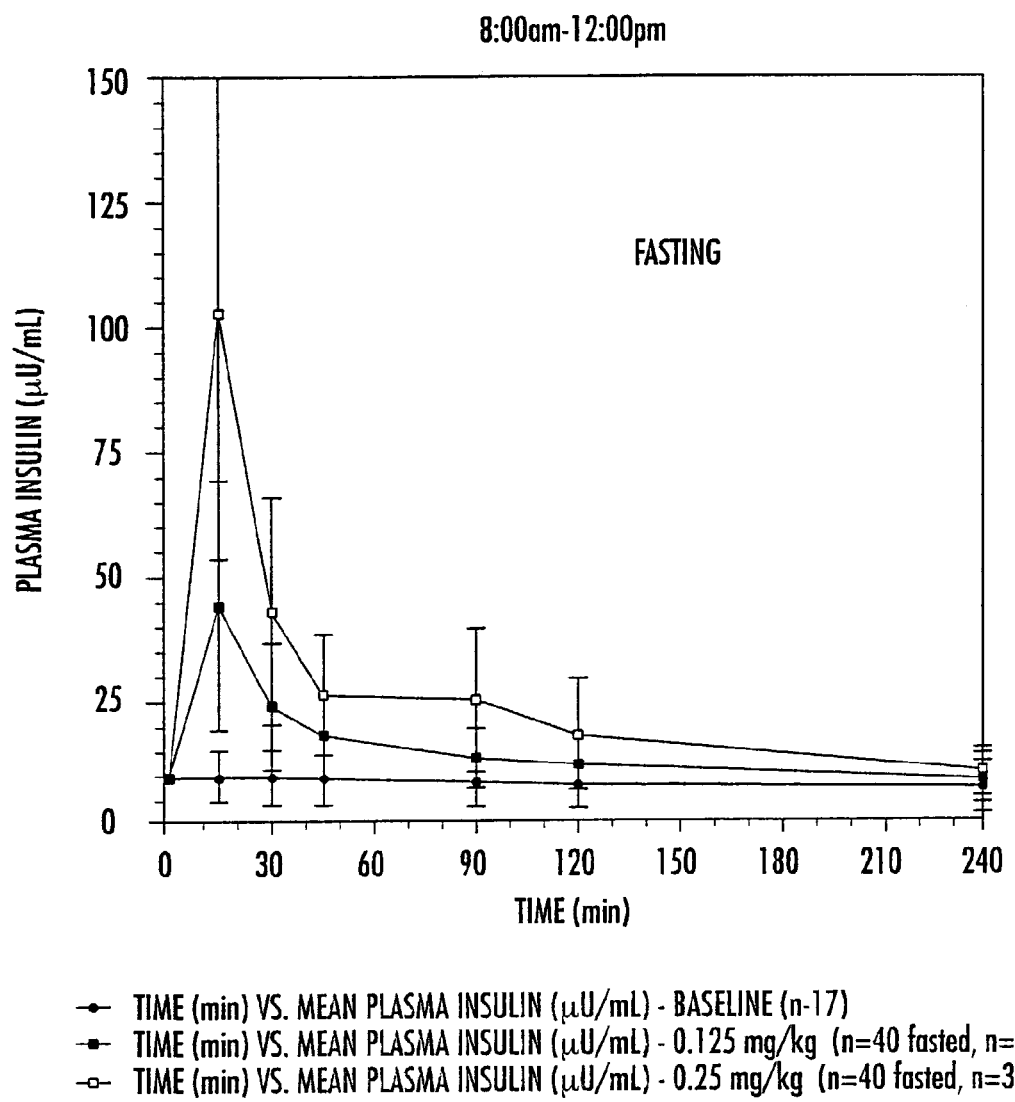
FIG. 2 illustrates a comparison of mean plasma insulin vs. time curve resulting from oral administration of various doses of embodiments of the present invention in fasting, non-diabetic subjects compared with a mean plasma insulin vs. time curve for baseline plasma insulin.
Figure 3:
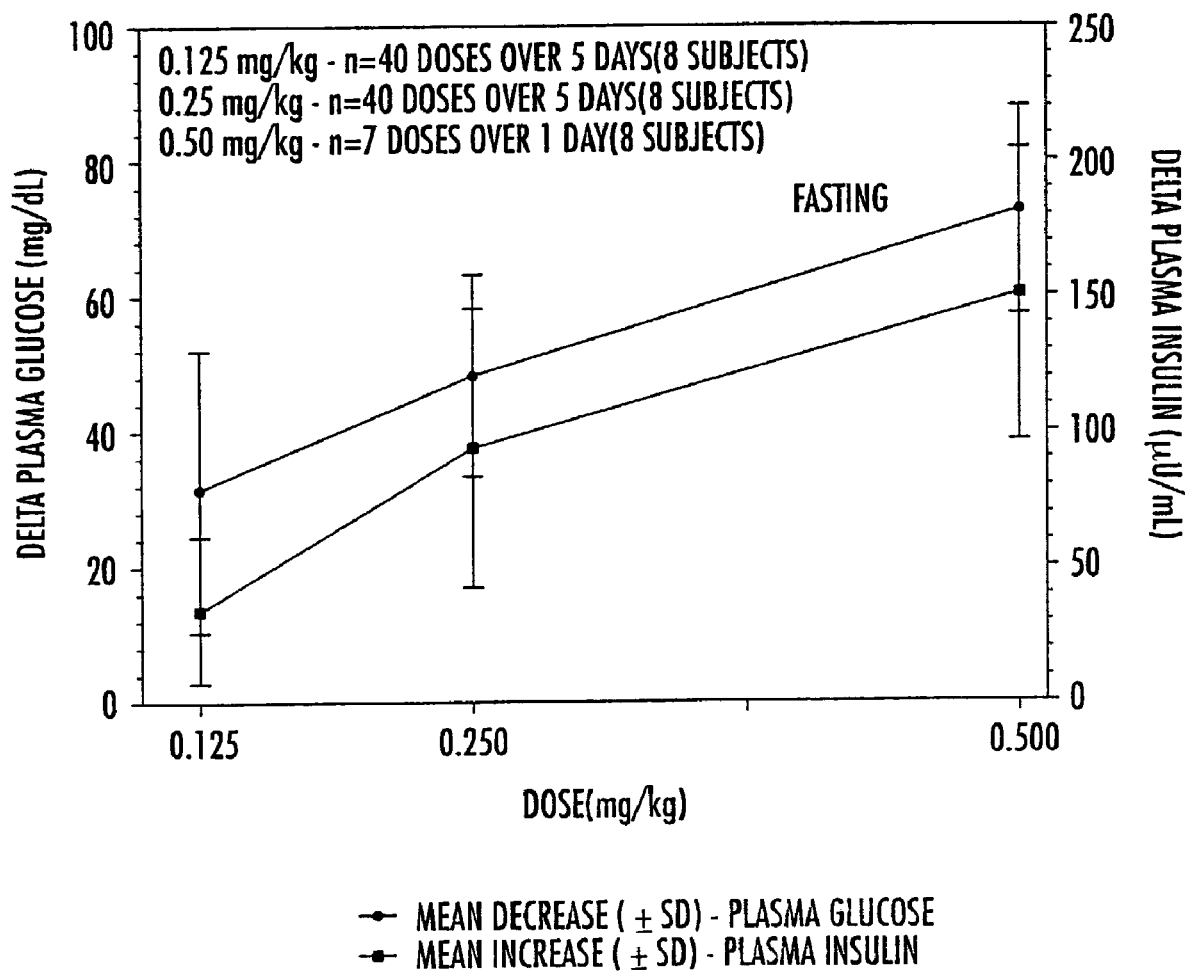
FIG. 3 illustrates glucose and insulin dose responses resulting from oral administration of embodiments of the present invention in fasting, non-diabetic subjects.

For the pre-prandial phase (fasted), subjects were fasted overnight and a single dose was administered in the morning. If blood glucose levels fell below 50 mg/dL, the subjects were rescued with a dextrose infusion. The effect of the conjugate HIM2 on blood glucose levels is illustrated in FIG. 1. HIM2 plasma levels (expressed in insulin equivalents) are shown in FIG. 2. The glucose/dose response and HIM2/dose response is shown in FIG. 3.

Figure 4:
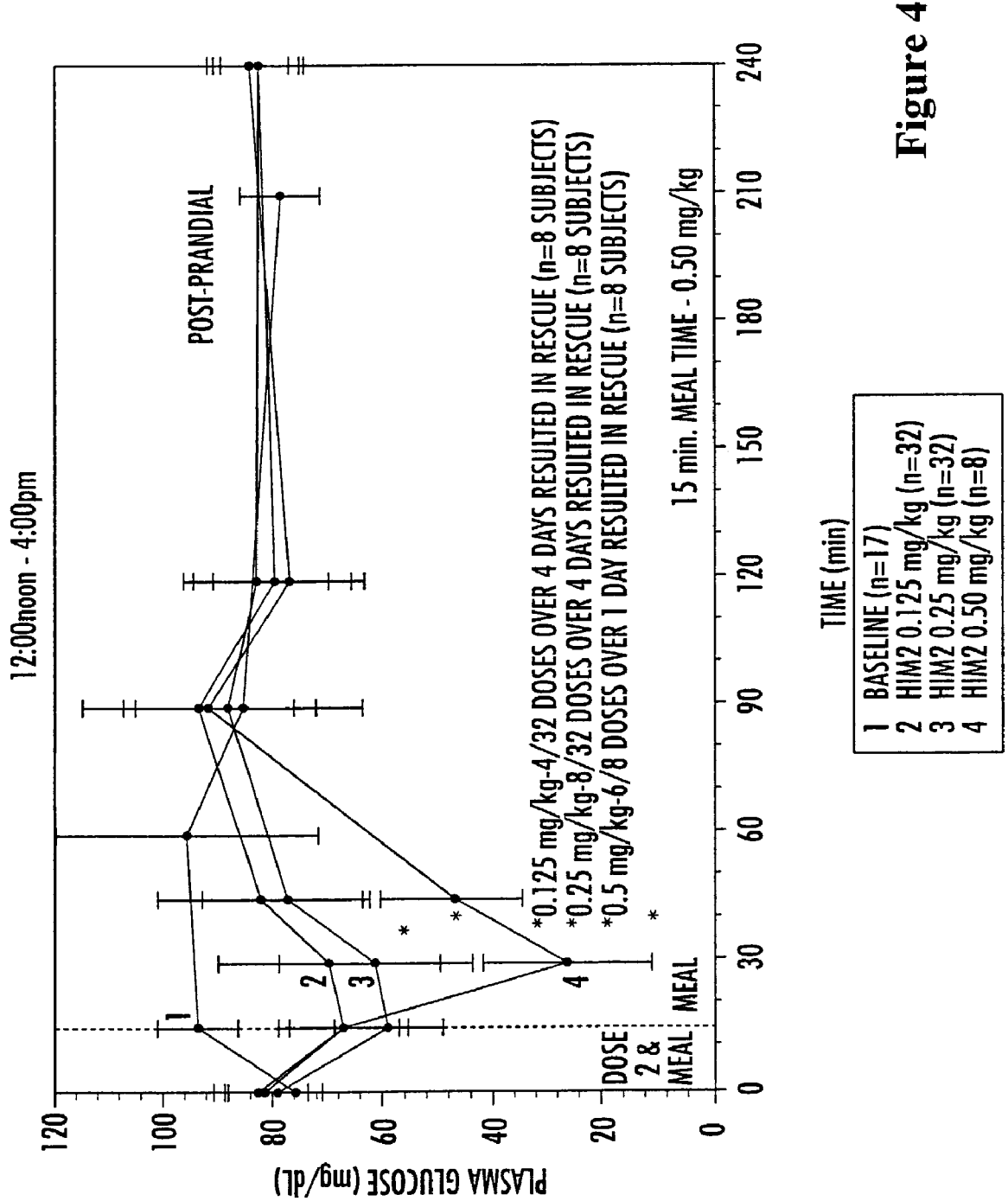
FIG. 4 illustrates a comparison of mean plasma glucose vs. time curves resulting from post-prandial, oral administration of various doses of embodiments of the present invention in non-diabetic subjects compared with a mean plasma glucose vs. time curve for baseline plasma glucose.
Figure 5:
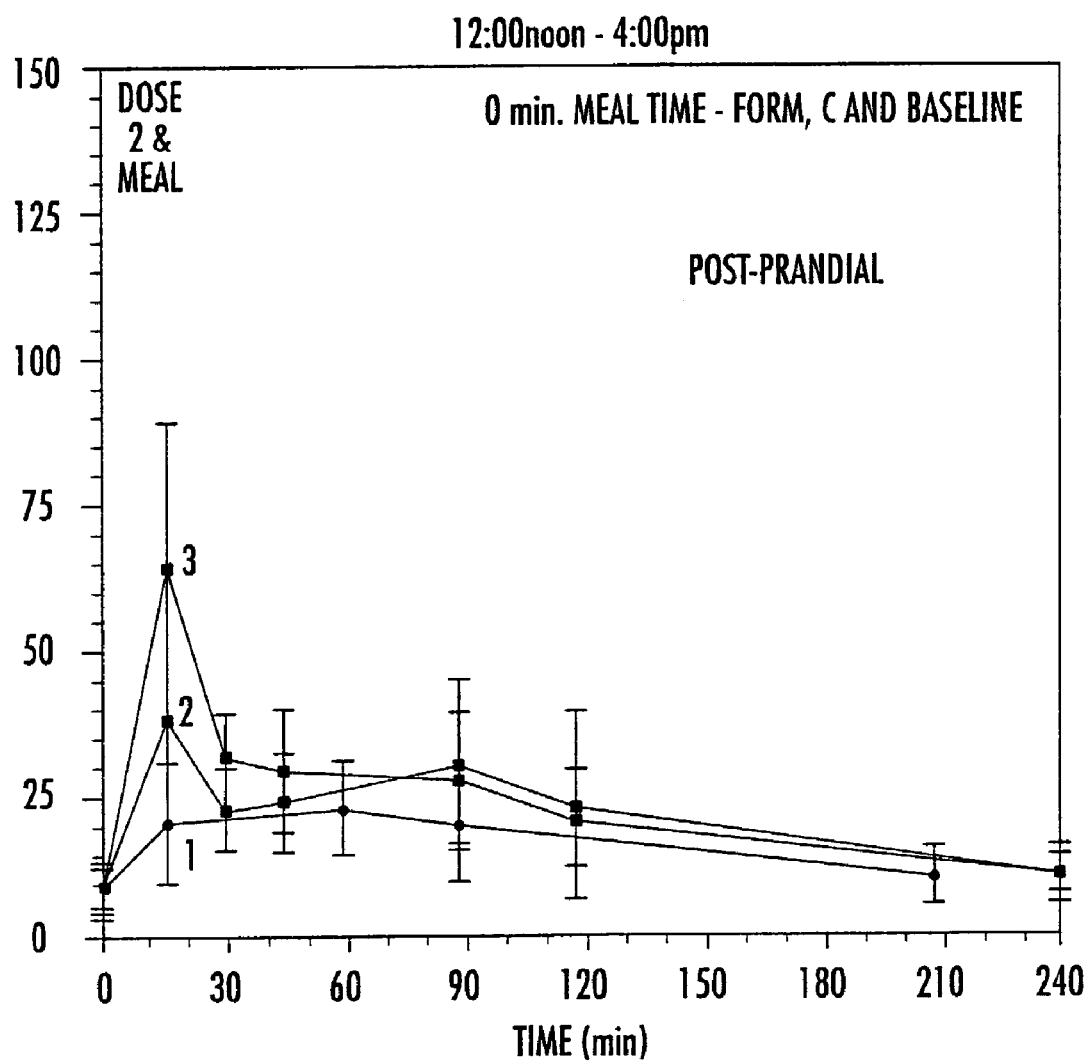
FIG. 5 illustrates a comparison of mean plasma insulin vs. time curve resulting from post-prandial, oral administration of various doses of embodiments of the present invention in non-diabetic subjects compared with a mean plasma insulin vs. time curve for baseline plasma insulin.
Figure 6:
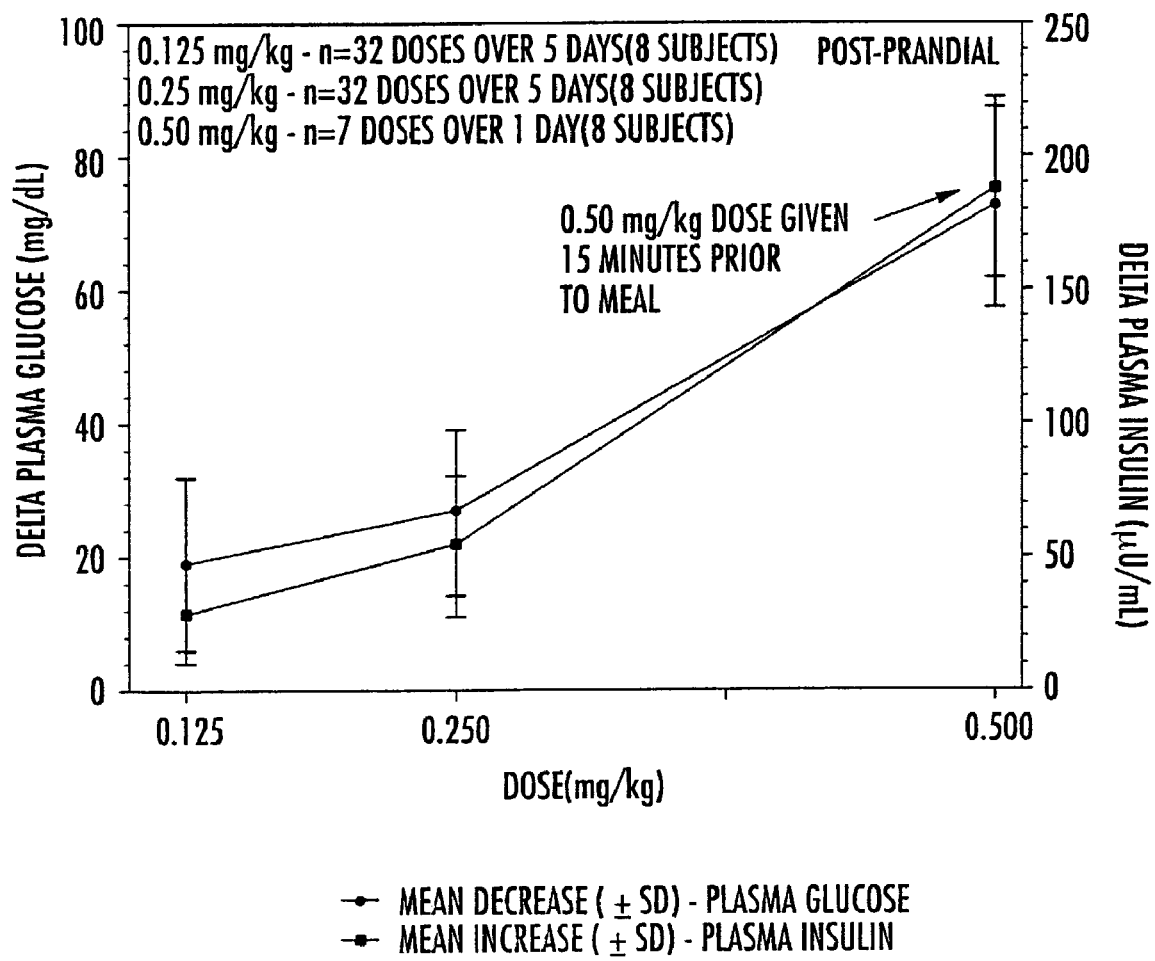
FIG. 6 illustrates glucose and insulin dose responses resulting from post-prandial oral administration of embodiments of the present invention in non-diabetic subjects.

For the post-prandial phase (fed), subjects received a single dose followed 15 minutes later by a meal. If blood glucose levels fell below 50 mg/dL, the subjects were rescued with a dextrose infusion. The effect of the conjugate HIM2 on blood glucose levels is illustrated in FIG. 4. HIM2 plasma levels (expressed in insulin equivalents) are shown in FIG. 5. The glucose/dose response and HIM2/dose response is shown in FIG. 6.

Example 16

Liquid oral pharmaceutical compositions formulated as described herein were administered to male CF-1 mice (~20–25 g). The animals were fasted overnight and deprived of food during the experiment. Water was provided ad libitum. The mice were maintained in cages with 5 animals per cage and kept in a room with a 12:12 L:D cycle (6:00 a.m.–6:00 p.m.). The mice were tested in groups of 5 animals per dose. Each group of mice (N=5) received either insulin conjugate-075, insulin conjugate-076, insulin-conjugate-084, insulin conjugate-106 or HIM2 orally at 1.25 and 2.5 mg/kg.

Figure 7:
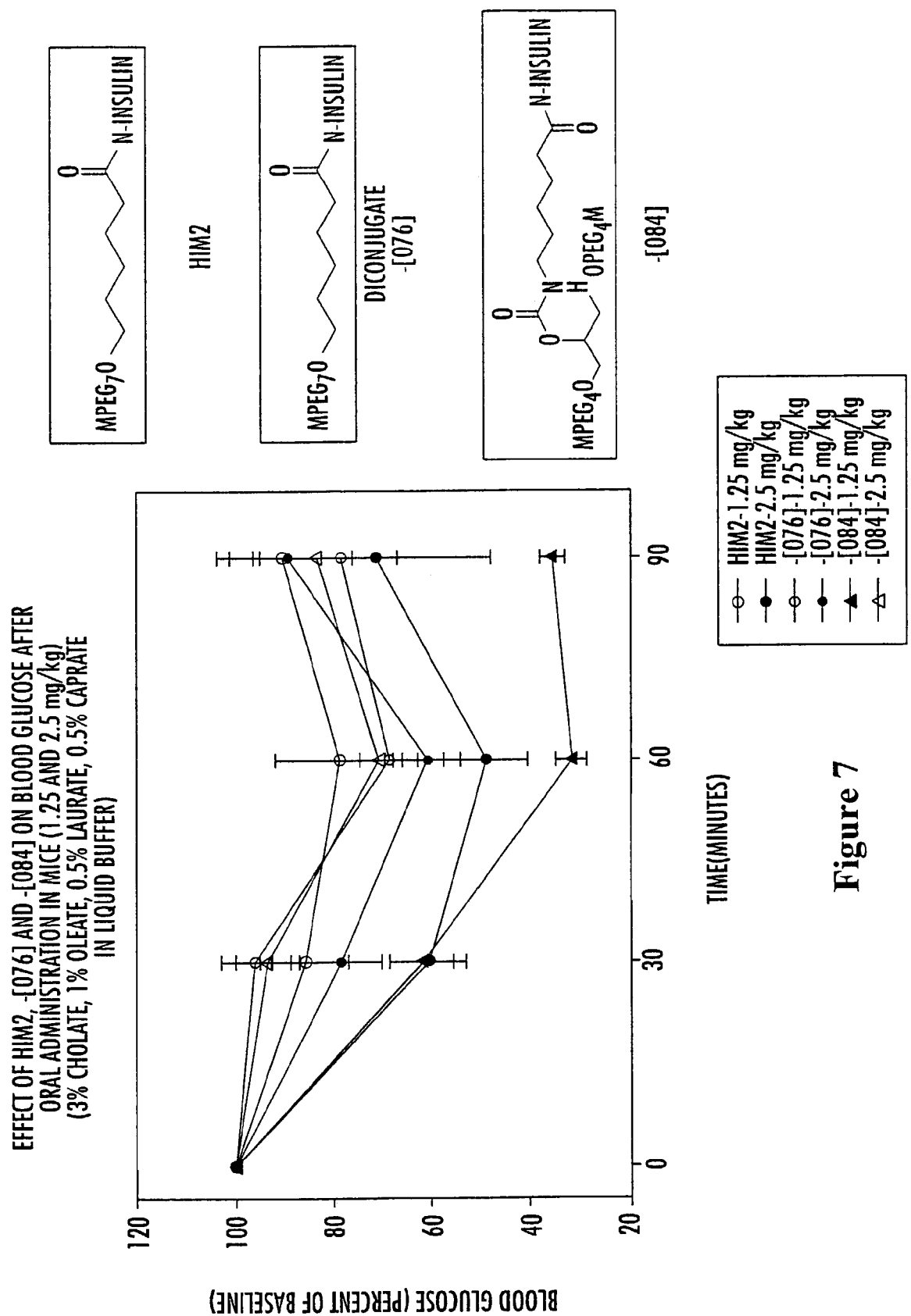
FIG. 7 illustrates a blood glucose vs. time curve resulting from oral administration of embodiments of the present invention in mice.
Figure 8:
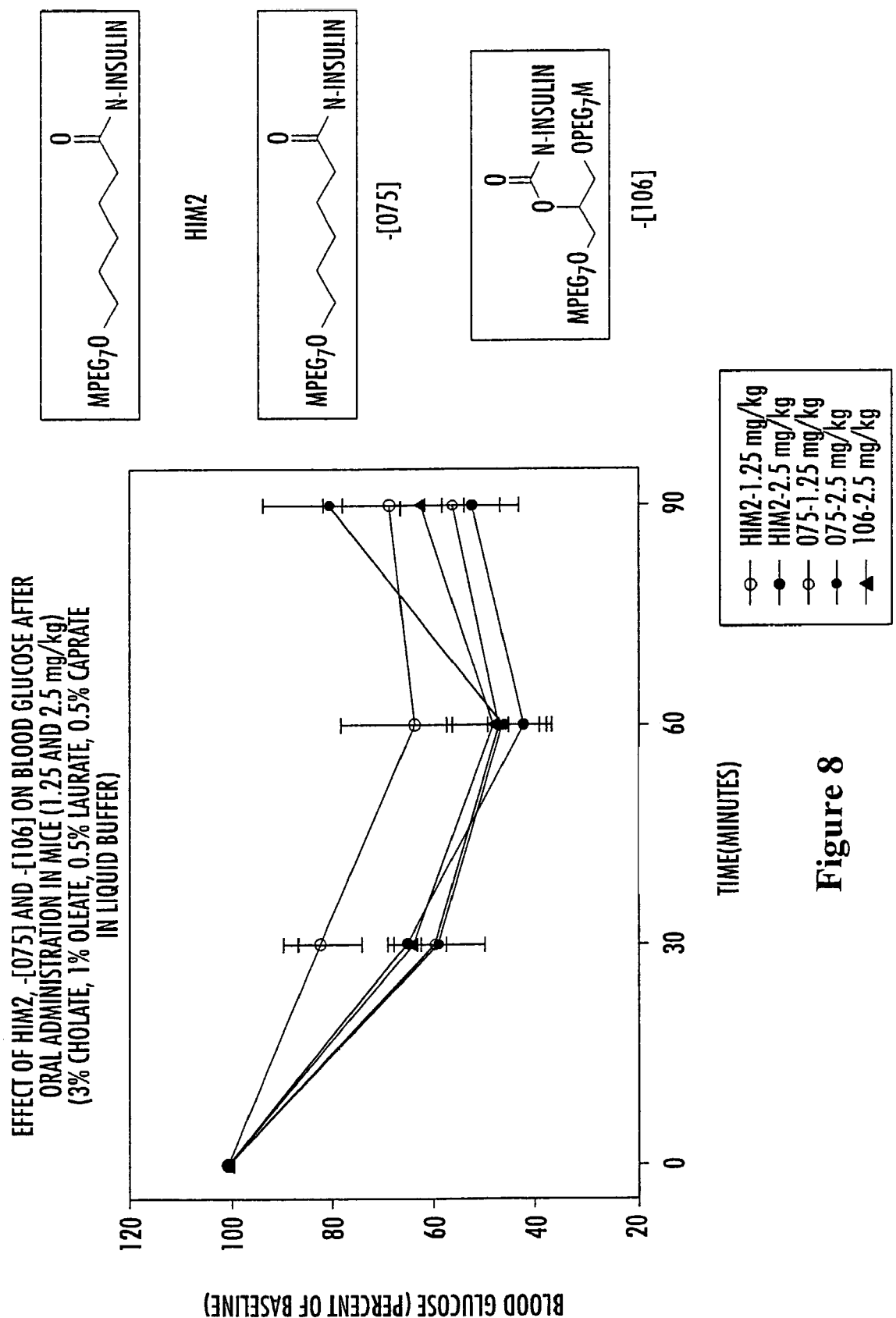
FIG. 8 illustrates a blood glucose vs. time curve resulting from oral administration of embodiments of the present invention in mice.
Figure 9:
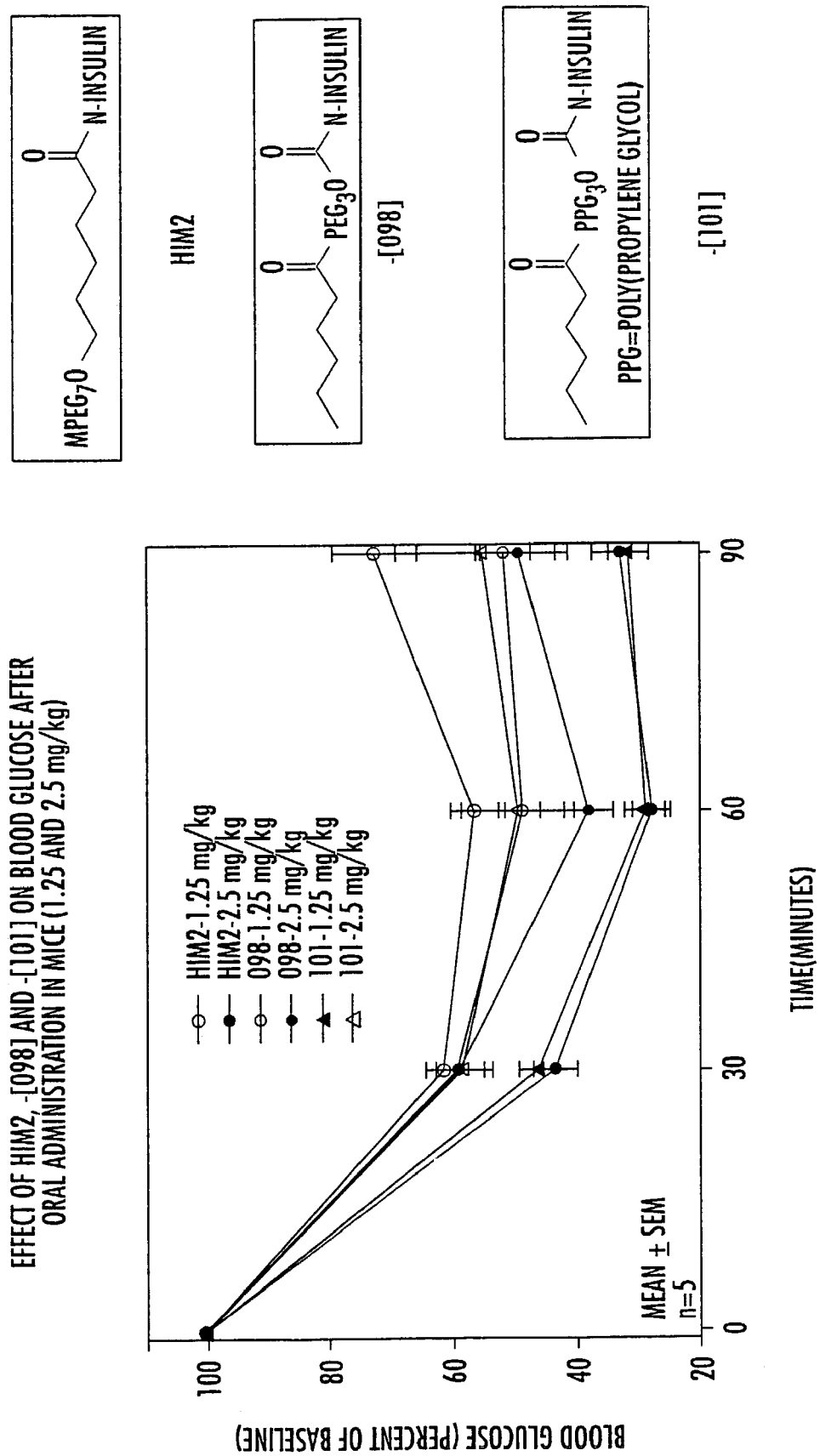
FIG. 9 illustrates a blood glucose vs. time curve resulting from oral administration of embodiments of the present invention in mice.

The insulin conjugates and HIM2 were provided at concentrations of 0.125 and 0.25 mg/ml. The dosing volume was 10.0 mL/kg. Total doses (each compound) that the animals received were 1.25 and 2.5 mg/kg. Oral doses were administered using a gavaging needle (Popper gavage needle for mice #20; 5 cm from hub to bevel). The effect of the various conjugates on blood glucose level is illustrated in FIGS. 7, 8, and 9.

Example 17

Adult, male beagles dogs having a body weight of 8–15 kg were fasted overnight. The dogs were distributed equally by body weight among treatment groups with N=4/group. Tap water was provided ad libitum. The dogs were maintained in their assigned groups per protocol. The dogs were tested in groups of 4 animals per dose. The route of administration was bolus oral administration. Each group of dogs (n=4) received CT-025 at 25 µg/kg of liquid or ~10–23 µg/kg of tablet formulations in groups of 4 animals per dose. The dosing volume was 0.2 mL/kg. Liquids were administered by applying to the back of the throat using an appropriate-sized gavaging syringe. One or two tablets were administered per dog. The CT-025 was provided at concentrations of 125 ug/mL of liquid formulation or 125 ug per tablet weight. The dogs were re-fed approximately one hour after the final blood sampling.

Figure 10:
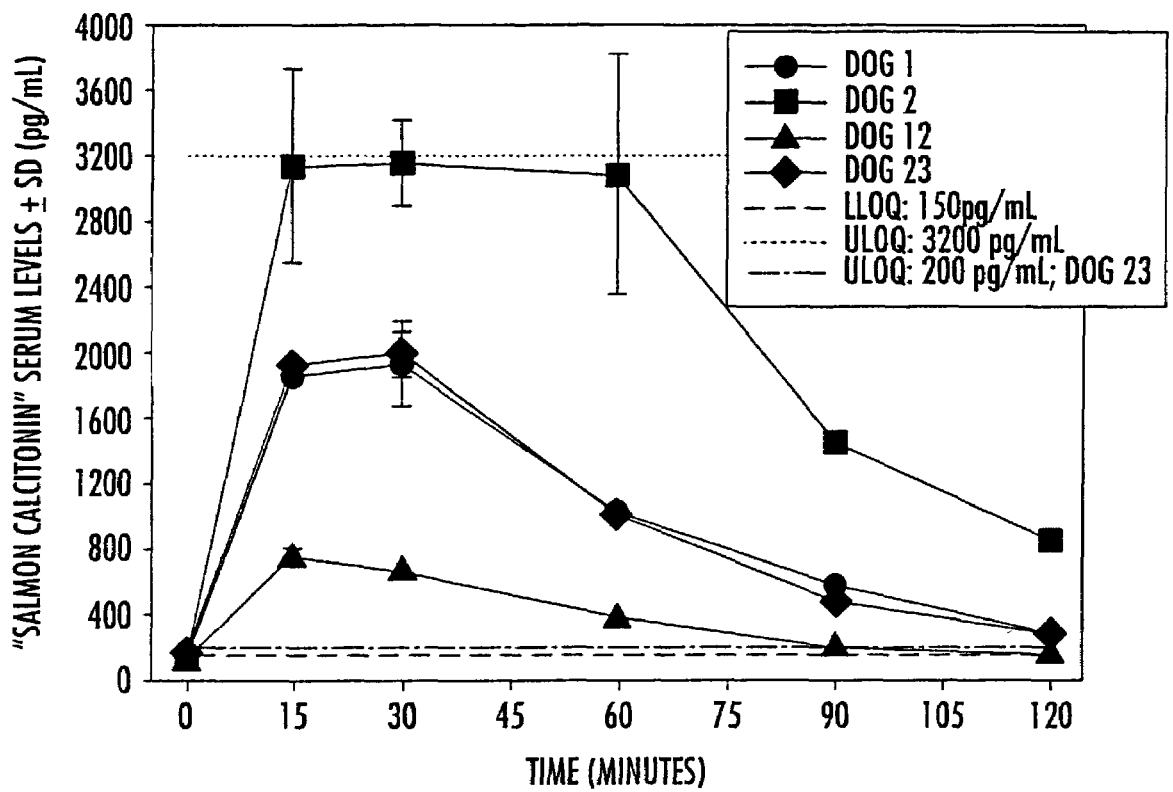
FIG. 10 illustrates a calcitonin serum level vs. time curve resulting from oral administration of liquid formulation embodiments of the present invention in beagle dogs.

FIG. 10 illustrates the effect of CT-025 conjugate administered as described above using the following liquid formulation, which was prepared using a procedure as described above in Example 13.

| Ingredient | Percent |
| --- | --- |
| CT-025 | 125 µg/ml |
| Phosphate buffer | 88.84 |
| Sodium caprate | 1.94 |
| Sodium laurate | 2.22 |
| Sodium chloride | 0.2 |
| Sodium cholate | 4.3 |
| Sucralose | 2 |
| Strawberry flavor | 0.5 |

Figure 11:
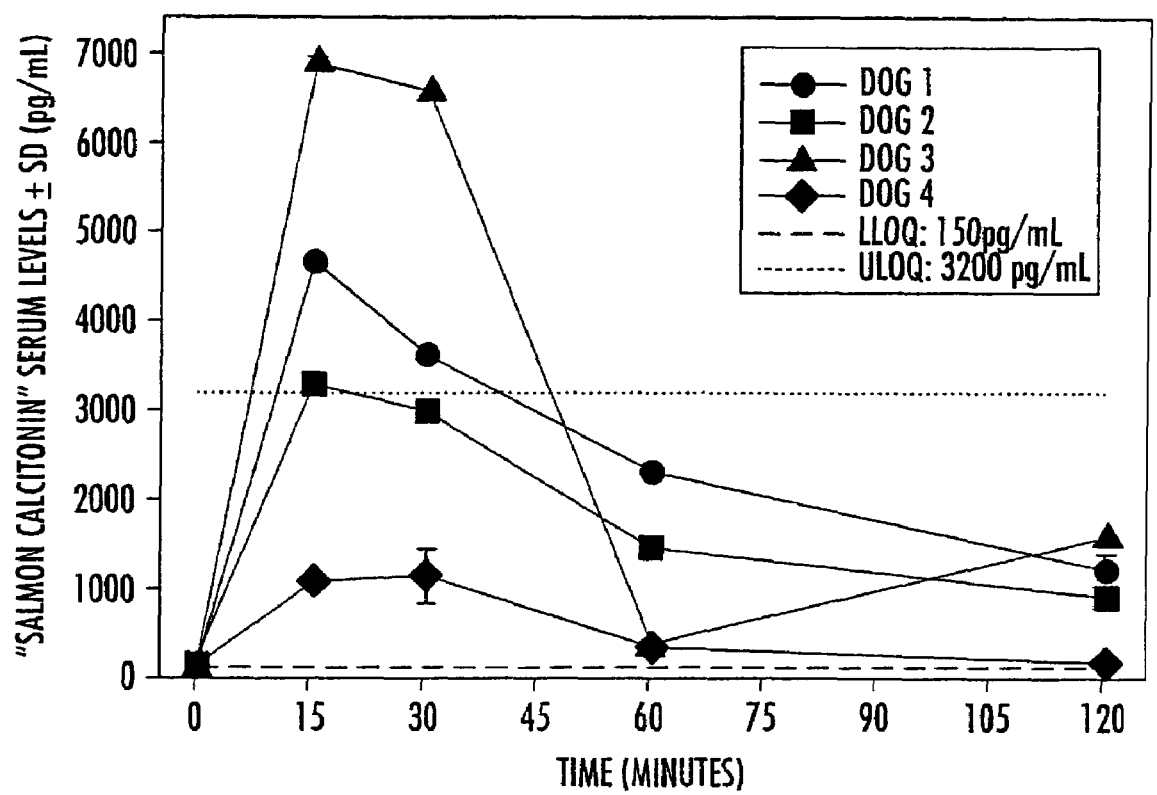
FIG. 11 illustrates a calcitonin serum level vs. time curve resulting from oral administration of liquid formulation embodiments of the present invention in beagle dogs.

FIG. 11 illustrates the effect of CT-025 conjugate administered as described above using the following liquid formulation, which was prepared using a procedure as described herein.

| Ingredient | Percent |
| --- | --- |
| CT-025 | 125 µg/ml |
| Phosphate buffer | 88.51 |
| Capric acid | 1.72 |
| Lauric acid | 2 |
| Sodium chloride | 0.2 |
| Sodium cholate | 4.3 |
| Sodium hydroxide pellets | 0.77 |
| Sucralose | 2 |
| Strawberry flavor | 0.5 |

Figure 12:
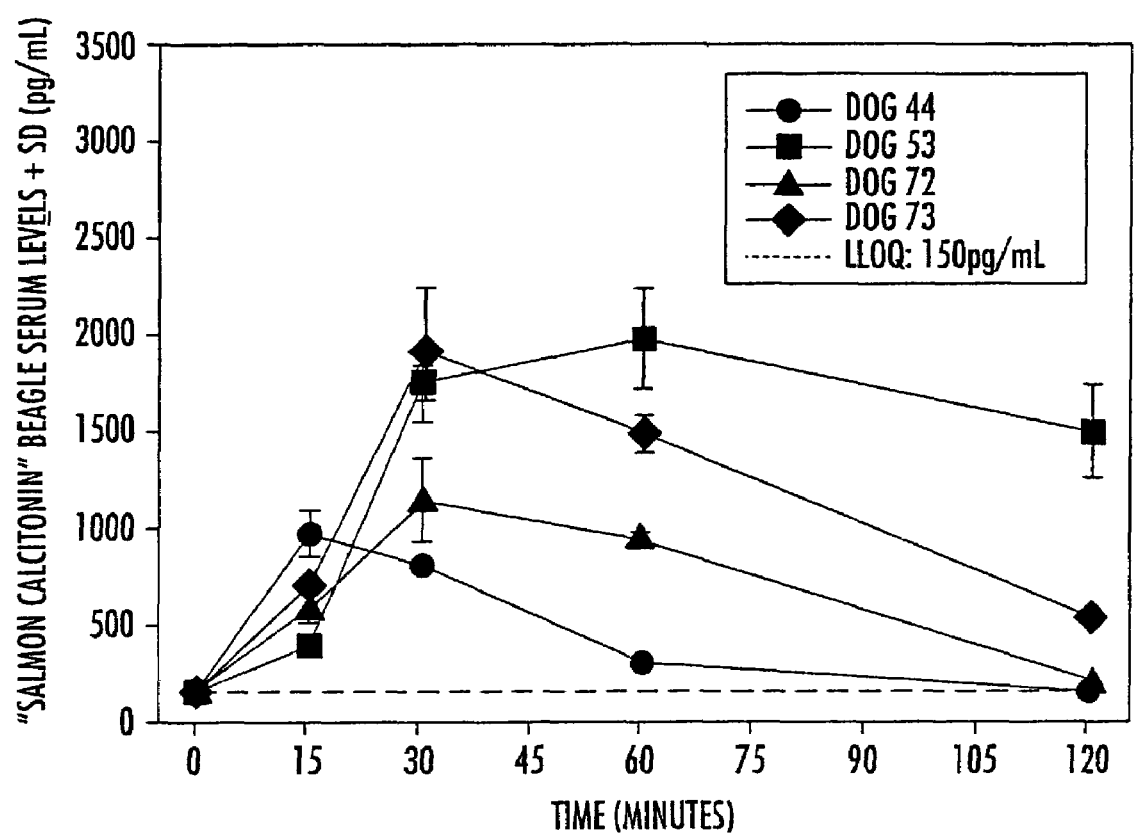
FIG. 12 illustrates a calcitonin serum level vs. time curve resulting from oral administration of solid formulation embodiments of the present invention in beagle dogs.

FIG. 12 illustrates the effect of CT-025 conjugate administered as described above using a formulation as described herein

Example 18

Oral Dosing of C-Peptide Conjugate & Its Blood Levels in Mice

Figure 13:
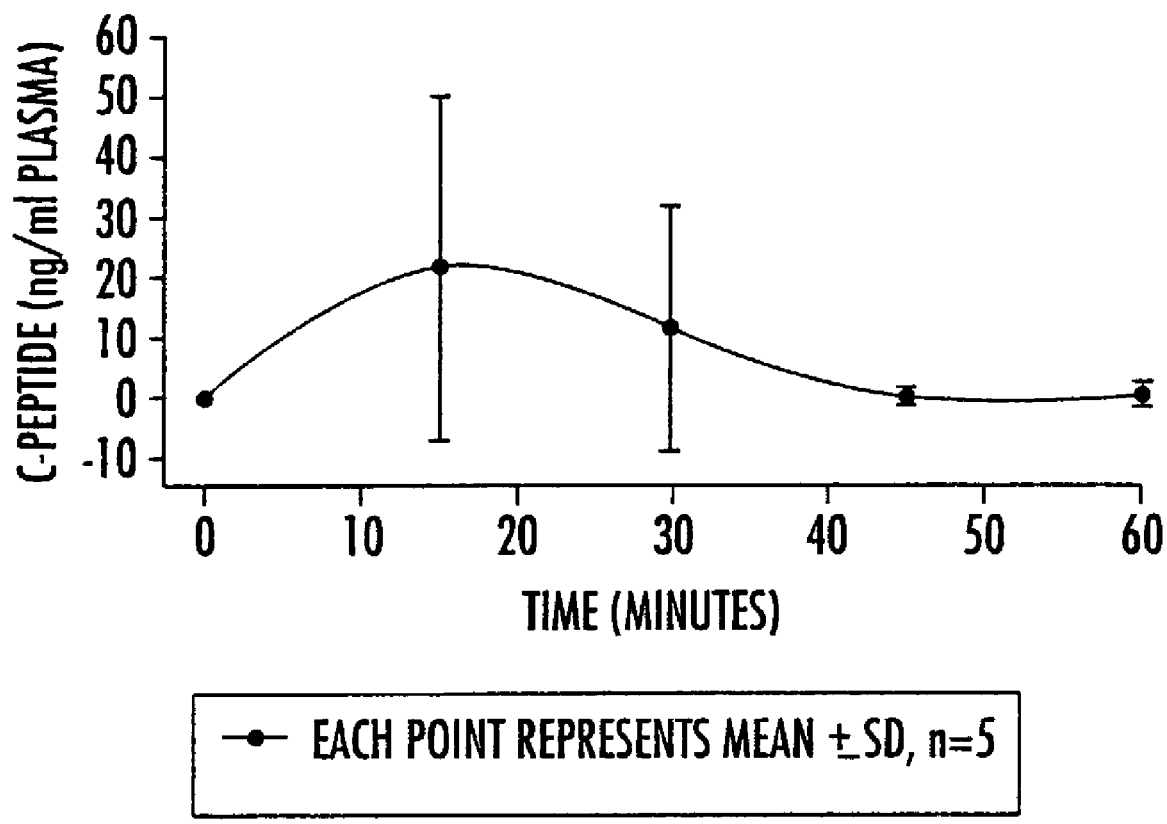
FIG. 13 illustrates a plasma concentration of C-peptide resulting from oral administration of liquid formulation embodiments of the present invention in mice.

Mice (fasted over-night) were orally administered C-peptide conjugate (1.92 mg/kg bw) in a liquid formulation (200 µg/mL) as described herein. The C-peptide conjugate was human C-peptide, having glutamate at its N-terminus and lysine at its C-terminus, with an oligomer having the structure $CH_3O(C_2H_4O)C(O)$— attached by an amide bond to the lysine of the human C-peptide. At each time intervals of 15, 30, 45, & 60 minutes, mice were anesthetized with ether and blood collected from the vena cava with heparinized syringes. Plasma was separated, stored at −80° C., and transferred for analysis of C-peptide conjugate in plasma. The plasma effects of the orally administered C-peptide conjugate are shown in FIG. 13.

Example 19

Preparation of Formulations. Bile salts, sodium phosphate, and HIM2 were dissolved in purified water and adjusted to pH 7.8.

Mouse Model. CF1 mice of 20 to 25 g were administered intragastric boluses of 10 mL/kg of formulations containing 1.0 mg/mL HIM2 and sodium taurocholate or sodium taurodeoxycholate (5% bile salt and 1.5% bile salt) or formulations containing 0.5 mg/mL HIM2 and sodium glyocholate or sodium ursodeoxycholate (0.15% bile salt, 0.5% bile salt, 1.5% bile salt or 5% bile salt). Blood glucose was measured prior to and 60 minutes after dosing. Results are expressed as the ratio of 60 and 0 minute tail artery blood glucometer readings.

Dog Model. Adult male beagle dogs were fasted overnight. Oral doses of 0.2 mL/kg of formulations containing 5 mg/mL HIM2 (1 mg/kg) and various levels (0.15%, 0.5%, 1.5%; 5%, 10%) of four different bile salts (TDc, DC, UDC, cholate) were followed by a water chaser of 1.0 mL/kg. Blood was sampled prior to and 15, 30, 60, and 120 minutes after dosing.

Calculation of Glucose Area Over the Curve (AOC). AOC was calculated by the trapezoid rule as the integral of percent blood glucose drop with time.

Figure 14:
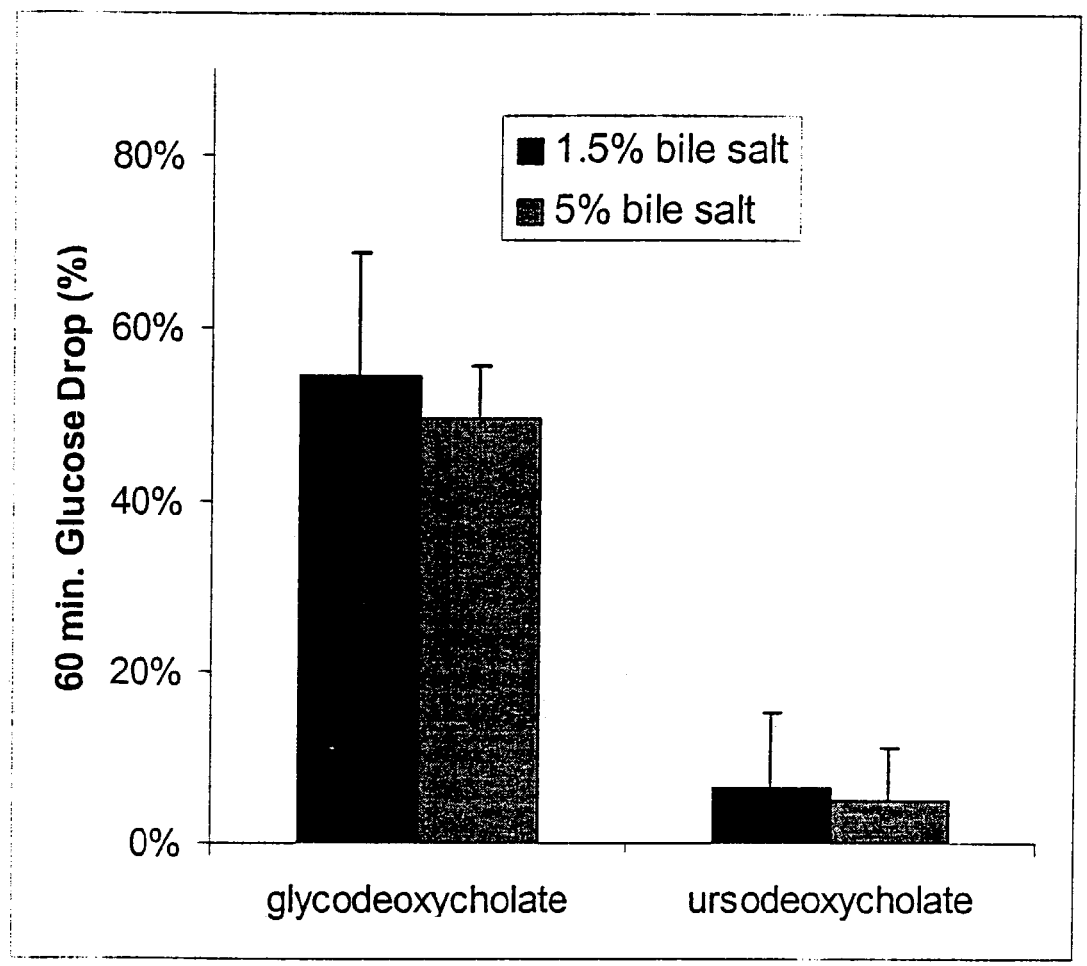
FIG. 14 illustrates a comparison of the percent drop in glucose over 60 minutes after administration of an intragastric bolus of 10 mL/kg of embodiments of the present invention in mice (error bars represent standard error (n=5))
Figure 15:
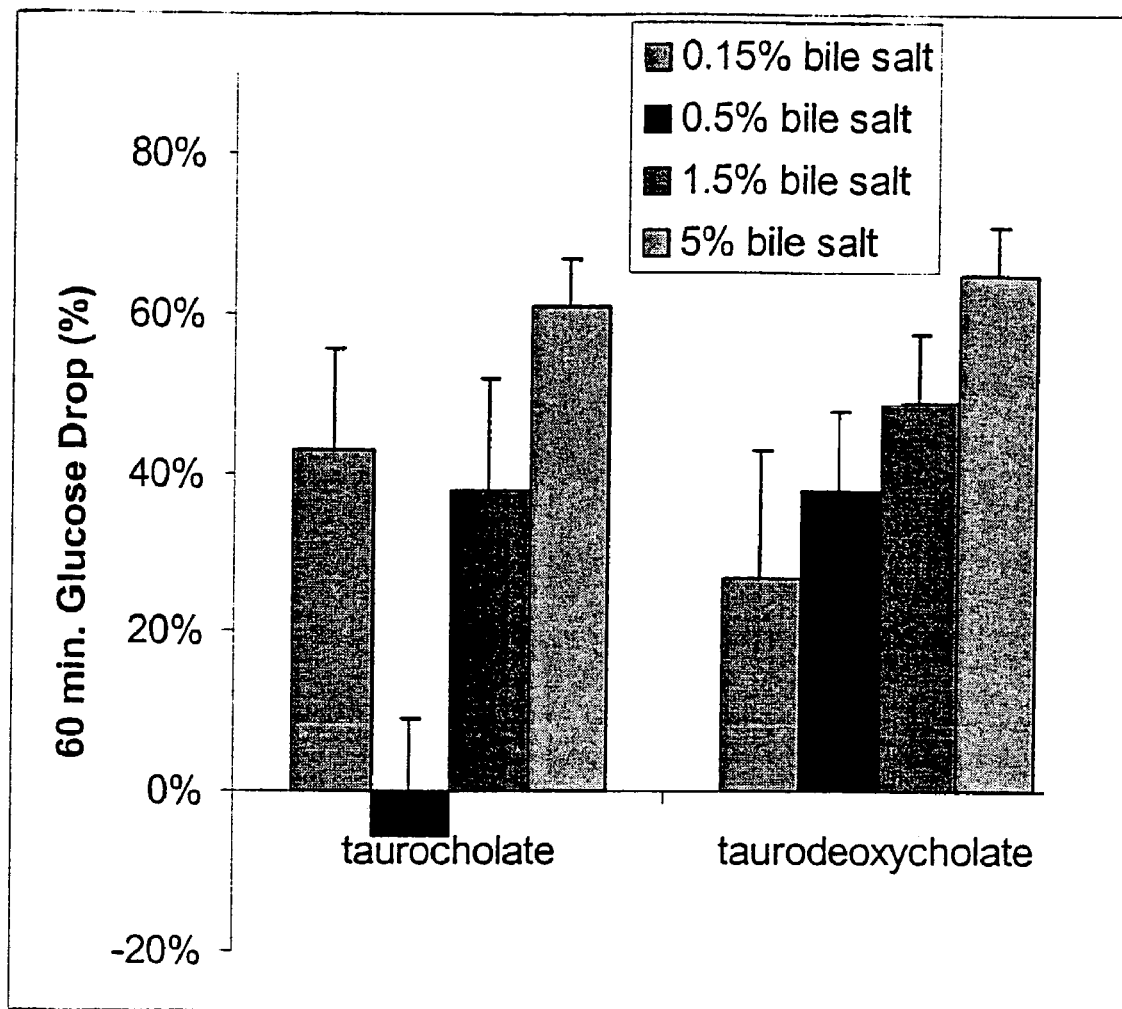
FIG. 15 illustrates a comparison of the percent drop in glucose over 60 minutes after administration of an intragastric bolus of 10 mL/kg of embodiments of the present invention in mice (error bars represent standard error (n=5))
Figure 16:
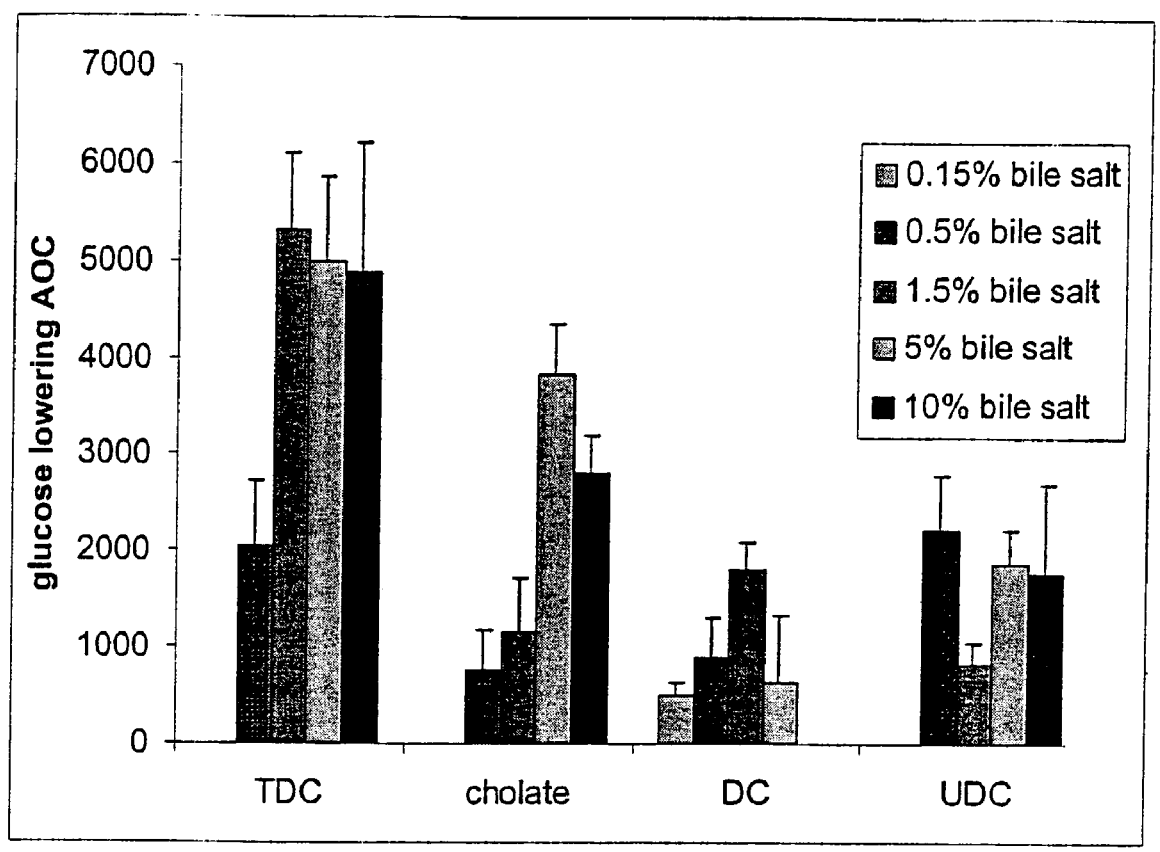
FIG. 16 illustrates a comparison of glucose lowering in dogs, calculated as Area Over the Curve (AOC), after administration of an oral dose of 0.2 mL/kg of embodiments of the present invention followed by a water chaser of 1.0 mL/kg. TDC=taurodeoxycholate, DC=deoxycholate, UDC=ursodeoxycholate.

Results of administering HIM2 in bile salt solutions to mice are shown in FIGS. 14 and 15. Dog study results are given in FIG. 16. In almost all cases, substantial reductions in blood glucose were observed as the result of co-administration of HIM2 and bile salts.

Similar levels of glucose reduction were observed in mice when HIM2 was administered with taurocholate, taurodeoxycholate or glycodeoxycholate (FIGS. 14 and 15). Ursodeoxycholate was significantly less effective than glycodeoxycholate ($p<0.05$).

In dogs a clear response to different bile salt levels was observed. For example, blood glucose Area Over the Curve (AOC) values were significantly higher ($p<0.05$) for HIM2 in 5% sodium cholate than for HIM2 in 0.5% or 1.5% sodium cholate. Likewise deoxycholate was significantly more effective at 1.5% than at 0.15% and taurodeoxycholate was more effective at 1.5% than at 0.5%. Ursodeoxycholate was the only bile salt that did not show a significant concentration effect in dogs.

All of the bile salts were effective at a level of 1.5%. This corresponds to about 500 micromoles per dose, or about 2% of mean daily bile salt secretion for non-obese humans (Reuben et al. 1985, "Bile salt secretion in obese and on-obese individuals with and without gallstones" *Clin. Sci,* (Lond.) 69(1)"71–9). Thus, absorption of HIM2 is enhanced using bile salts at levels that represent a small fraction of physiological secretion.

Example 20

A single-centered, randomized, open-label, 2-way crossover study on Hexyl-Insulin Monoconjugate 2 (HIM2) and regular recombinant insulin was conducted. The drug compounds were administered orally in liquid formulation according to example 11 to healthy adult subjects. Each subject received a dose that was prepared individually to account for that subject's body weight and for the dose that subject was to receive. The 6 mg/mL concentrate prepared in example 11 was mixed with a matching diluent to deliver the desired dose (0.06 mg/kg or 0.125 mg/kg or 0.25 mg/kg of HIM2 or regular insulin) in 20 mL of the mixture.

Twelve subjects were fasted overnight and given a single dose in the morning. Blood samples were collected at 0, 10, 15, 20, 30, 45, 90, 120, and 240 minutes post-dose while the subjects remained in the fasted state. Plasma insulin concentrations and plasma glucose concentrations were determined for each subject.

Figure 17:
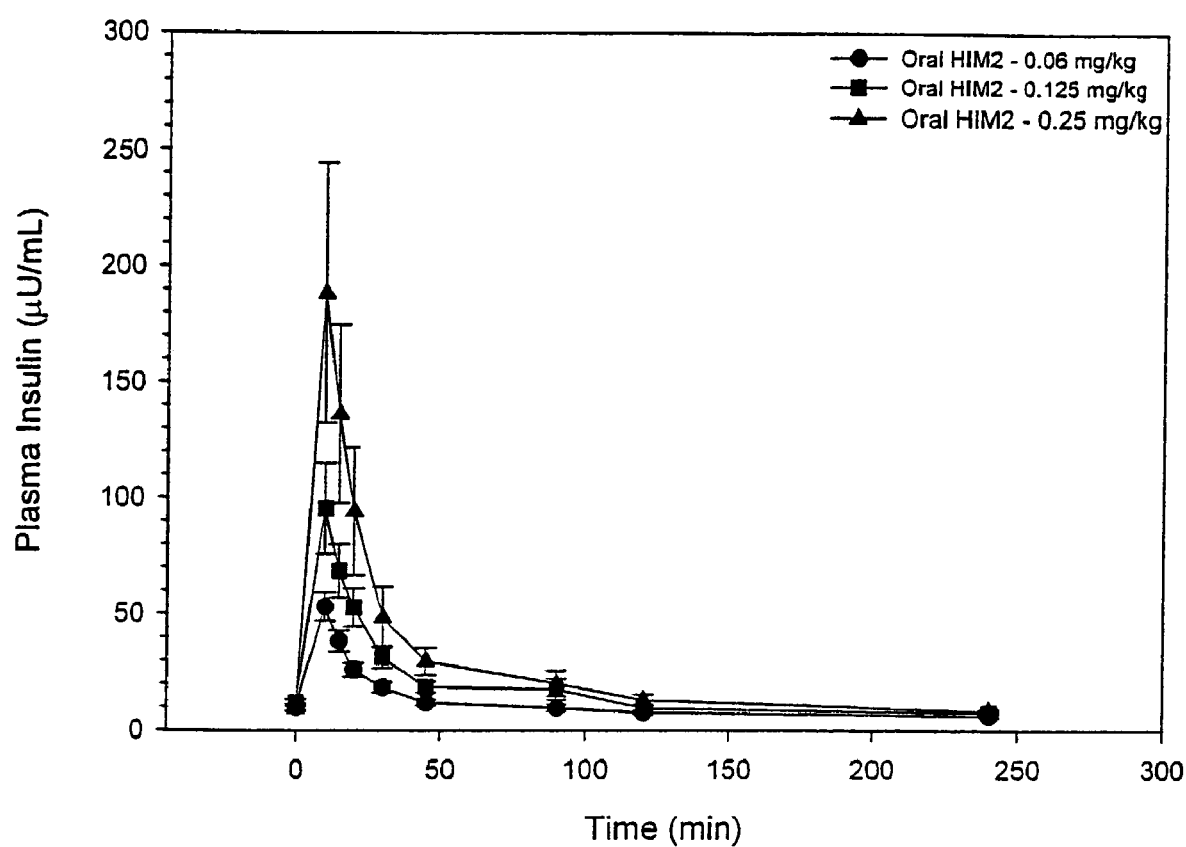
FIG. 17 illustrates a plasma insulin versus time curve resulting from oral administration of a composition of this invention comprising HIM2 to humans.
Figure 18:
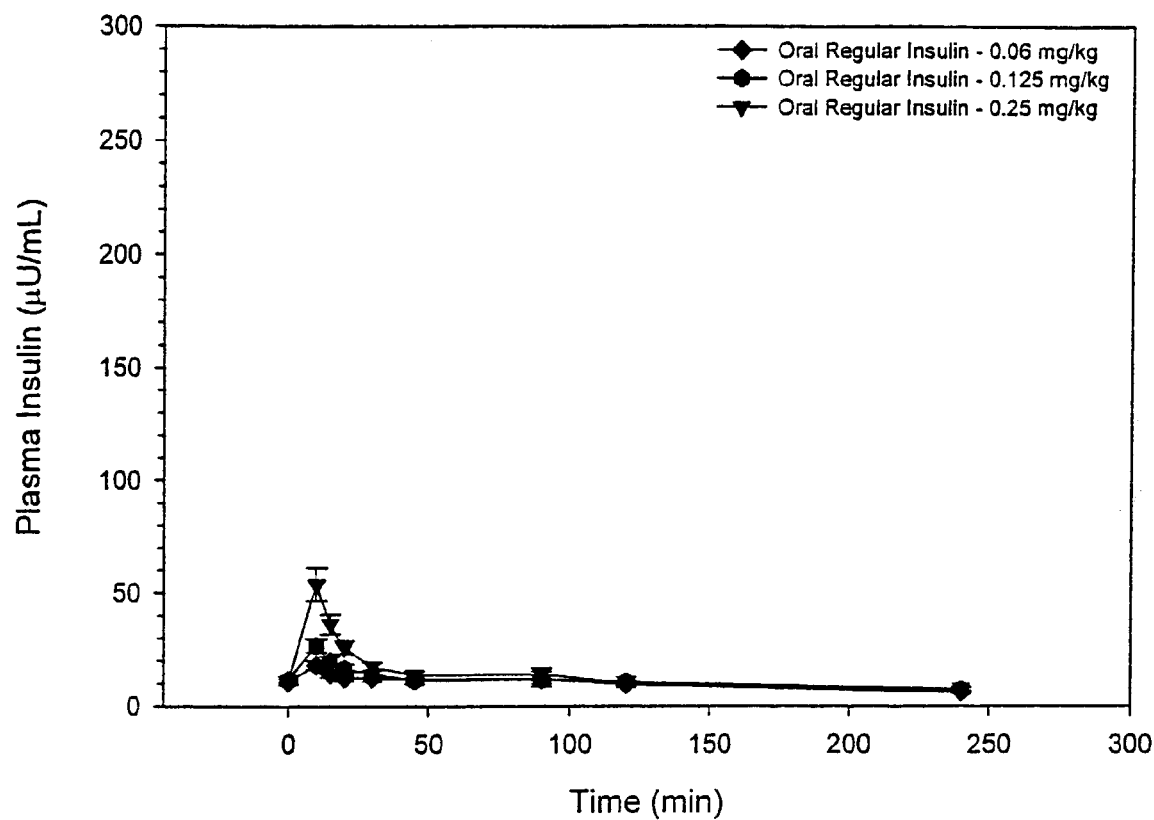
FIG. 18 illustrates a plasma insulin versus time curve resulting from oral administration of a composition of this invention comprising recombinant insulin to humans.

As shown in FIGS. 17 and 18, HIM2 and regular insulin delivered with the formulation at the doses used were orally available in a dose dependent manner. The higher plasma levels achieved with HIM2 are due to the enzymatic protection provided by the conjugation with an oligomer and to the longer circulating half life of the HIM2 molecule compared to the native insulin molecule.

| HIM2 Excipients details | |
| --- | --- |
| Excipient | Amount |
| Capric Acid | 51.77 |
| Croscarmellose Sodium | 30 |
| Insulin as Protein | 6.5 |
| Lauric Acid | 51.77 |
| Magnesium Stearate | 6 |
| Mannitol | 257.5 |
| Sodium Cholate | 155.31 |
| Sodium Hydroxide Pellets | 19.67 |
| Sodium Phosphate Monobasic Monohydrate | 21.48 |

Four adult, male Beagle dogs with body weights in the range 10–13 kg were fasted overnight. Tap water was available ad libitum (except for a period of no water for 2 hours pre-dosing until 1 hour post dosing). An assessment of hypoglycemia post-dosing was done.

Each tablet contained 6.5 mg of HIM2 in the excipient described above to achieve a target dose of ~0.5 mg/kg. Doses were administered by placing to the back of the throat. Immediately following the administration of the test article, the animals were given 1 ml/kg of tap water to the back of the throat using an appropriate-sized syringe.

Approximately 2.5 ml of blood was collected from the jugular vein in heparin-containing tubes from all animals immediately prior to the dose, and at 15, 30, 60 and 120 minutes post-dosing. The samples were mixed immediately by inverting, placed on a rocker and then centrifuged. An aliquot of plasma (0.75 ml) was frozen at −20° C. for subsequent analysis of insulin concentration.

Figure 19:
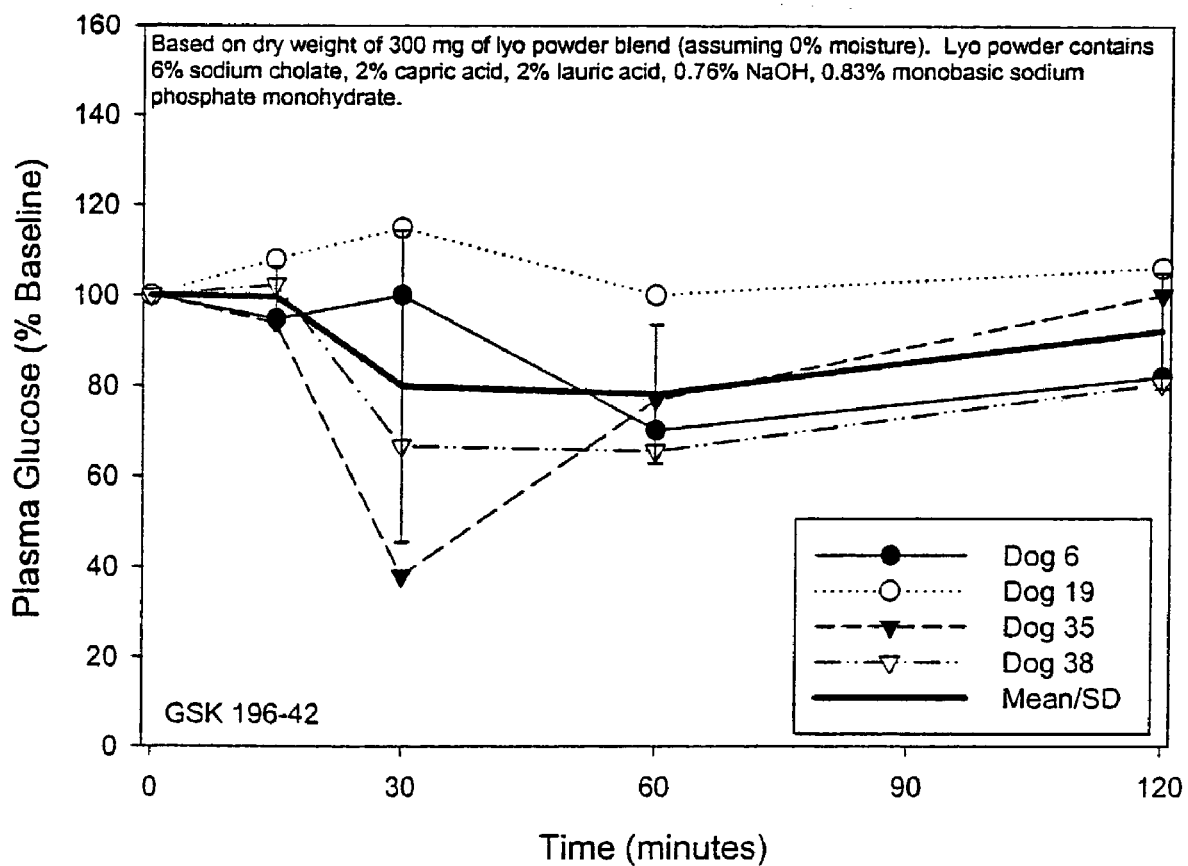
FIG. 19 illustrates a plasma glucose versus time curve resulting from oral administration of the embodiments of this invention to dogs.

The glucose-lowering effect of an uncoated tablet formulation was measured in fasted beagle dogs after oral dosing with one tablet that provided about 0.50 mg/kg of native insulin (FIG. 19) and pharmacodynamic effects were demonstrated.

The present invention has been described herein with reference to various embodiments. These embodiments do not serve to limit the invention, but are set forth for illustrative purposes. The scope of the invention is defined by the claims that follow.

The invention claimed is:

1. A pharmaceutical composition comprising (a) a drug-oligomer conjugate comprising a drug covalently coupled to an oligomeric moiety, wherein the oligomeric moiety is hydrophilic, (b) a bile salt, and (c) a pharmaceutically acceptable carrier.

2. The pharmaceutical composition of claim 1, wherein the bile salt is selected from the group consisting of taurocholate, taurodeoxycholate, cholate, deoxycholate and glycodeoxycholate.

3. The pharmaceutical composition of claim 2, wherein the bile salt is present in a concentration in the range of about 0.15% to about 10% bile salt.

4. The pharmaceutical composition of claim 2, wherein the bile salt is present in a concentration in the range of about 0.5% to about 5% bile salt.

5. The pharmaceutical composition of claim 1, wherein the pH of the composition is between 6.2 and 9.0.

6. The pharmaceutical composition of claim 1, further comprising a buffering component.

7. The pharmaceutical composition of claim 1, wherein the pharmaceutical composition is a liquid pharmaceutical composition.

8. The pharmaceutical composition of claim 7, wherein the liquid pharmaceutical composition is suitable for oral administration.

9. The pharmaceutical composition of claim 1, wherein the pharmaceutical composition is a solid dosage pharmaceutical composition.

10. The pharmaceutical composition of claim 1, wherein the composition is suitable for a route of administration selected from the group consisting of buccal, transdermal, peroral and nasal administration.

11. The pharmaceutical composition of claim 1, wherein the drug is a calcitonin polypeptide.

12. The pharmaceutical composition of claim 10, wherein the calcitonin polypeptide is salmon calcitonin.

13. The pharmaceutical composition of claim 12, wherein the drug-oligomer moiety comprises salmon calcitonin coupled to two oligomeric moieties, wherein one oligomeric moiety is coupled to the lysine at the 11 position of the salmon calcitonin and wherein one oligomeric moiety is coupled to the lysine at the 18 position of the salmon calcitonin.

14. The pharmaceutical composition of claim 1, wherein the drug-oligomer conjugate is present as a substantially monodispersed mixture.

15. The pharmaceutical composition of claim 1, wherein the drug-oligomer conjugate is present as a monodispersed mixture.

16. The pharmaceutical composition of claim 1, wherein the oligomeric moiety is polyethylene glycol.

17. A pharmaceutical composition comprising (a) a drug-oligomer conjugate comprising a drug covalently coupled to an oligomeric moiety, wherein the oligomeric moiety is alkane, (b) a bile salt, and (c) a pharmaceutically acceptable carrier.

18. A pharmaceutical composition comprising, in a pharmaceutically acceptable carrier:

a drug-oligomer conjugate comprising a drug covalently coupled to an oligomeric moiety;

a bile salt; and a fatty acid component, wherein the fatty acid is present in an amount wherein the solubility of the bile salt in the presence of the fatty acid is greater than the solubility of the bile salt in a corresponding composition lacking the fatty acid, and wherein the bile salt is cholate and the cholate is present in the amount of about 1.5% weight/volume and the fatty acid component comprises laurate and the laurate is present in the amount of 2% weight/volume.

19. The pharmaceutical composition of claim 18, wherein the pH of the composition is between 6.2 and 9.0.

20. The pharmaceutical composition of claim 18, further comprising a buffering component.

21. The pharmaceutical composition of claim 18, wherein the pharmaceutical composition is a liquid pharmaceutical composition.

22. The pharmaceutical composition of claim 21, wherein the liquid pharmaceutical composition is suitable for oral administration.

23. The pharmaceutical composition of claim 18, wherein the composition is suitable for a route of administration selected from the group consisting of buccal, transdermal, peroral and nasal administration.

24. The pharmaceutical composition of claim 21, wherein the liquid pharmaceutical composition is suitable for parenteral administration.

25. The pharmaceutical composition of claim 18, wherein the pharmaceutical composition is a solid dosage pharmaceutical composition.

26. The pharmaceutical composition of claim 18 wherein the drug is a calcitonin polypeptide.

27. The pharmaceutical composition of claim 26, wherein the calcitonin polypeptide is salmon calcitonin.

28. The pharmaceutical composition of claim 27, wherein the drug-oligomer conjugate comprises salmon calcitonin coupled to two oligomeric moieties, wherein one oligomeric moiety is coupled to the lysine at the 11 position of the salmon calcitonin, and wherein one oligomeric moiety is coupled to the lysine at the 18 position of the salmon calcitonin.

29. The pharmaceutical composition of claim 28, wherein the oligomeric moiety coupled to the lysine at the 11 position comprises the structure $CH_3O(C_2H_4O)_7—(CH_2)_7—C(O)—$ and wherein the oligomeric moiety coupled to the lysine at the 18 position of the salmon calcitonin comprises the structure $CH_3O(C_2H_4O)_7—(CH_2)_7—C(O)—$.

30. The pharmaceutical composition of claim 18, wherein the fatty acid component further comprises caprate.

31. A method of treating a bone disorder in a subject in need of such treatment, said method comprising administering to the subject a therapeutically effective amount of a pharmaceutical composition comprising (a) a drug-oligomer conjugate comprising a drug covalently coupled to an oligomeric moiety, (b) a bile salt, and (c) a pharmaceutically acceptable carrier, by an administration route selected from the group consisting of buccal, transdermal, peroral and nasal administration.

32. The method of claim 31, wherein the drug is a calcitonin polypeptide.

33. The method of claim 32, wherein the calcitonin polypeptide is salmon calcitonin.

34. The method of claim 33, wherein the drug-oligomer moiety comprises salmon calcitonin coupled to two oligomeric moieties, wherein one oligomeric moiety is coupled to the lysine at the 11 position of the salmon calcitonin, and wherein one oligomeric moiety is coupled to the lysine at the 18 position of the salmon calcitonin.

35. The method of claim 34, wherein the oligomeric moiety coupled to the lysine at the 11 position comprises the structure $CH_3O(C_2H_4O)_7$—$(CH_2)_7$—$C(O)$— and wherein the oligomeric moiety coupled to the lysine at the 18 position of the salmon calcitonin comprises the structure $CH_3O(C_2H_4O)_7$—$(CH_2)_7$—$C(O)$—.

36. The method of claim 31, wherein the drug-oligomer conjugate is present as a substantially monodispersed mixture.

37. The method of claim 31, wherein the drug-oligomer conjugate is present as a monodispersed mixture.

38. The method of claim 31, wherein the drug-oligomer conjugate is amphiphilically balanced.

39. The method of claim 31, wherein the oligomeric moiety comprises a hydrophilic moiety and a lipophilic moiety.

40. A method of treating bone disorder in a subject in need of such treatment, said method comprising administering to the subject a therapeutically effective amount of a pharmaceutical composition comprising (a) a drug-oligomer conjugate comprising a drug covalently coupled to an oligomeric moiety, wherein the oligomeric moiety is hydrophilic, (b) a bile salt, and (c) a pharmaceutically acceptable carrier.

41. The method of claim 40, wherein the oligomeric moiety is polyethylene glycol.

42. The method of claim 31, wherein the oligomeric moiety is lipophilic.

43. A method of treating bone disorder in a subject in need of such treatment, said method comprising administering to the subject a therapeutically effective amount of a pharmaceutical composition comprising (a) a drug-oligomer conjugate comprising a drug covalently coupled to an oligomeric moiety, wherein the oligomeric moiety is alkane, (b) a bile salt, and (c) a pharmaceutically acceptable carrier.

44. A method of treating a bone disorder in a subject in need of such treatment, said method comprising administering to the subject a therapeutically effective amount of the pharmaceutical composition of claim 18.

45. The method of claim 44, wherein the method comprises orally administering the pharmaceutical composition to the subject.

46. The method of claim 44, wherein the method comprises administering the pharmaceutical composition to the subject by an administration route selected from the group consisting of buccal, transdermal, peroral and nasal administration.

47. The method of claim 44, wherein the drug is a calcitonin polypeptide.

48. The method of claim 47, wherein the calcitonin polypeptide is salmon calcitonin.

49. The method of claim 48, wherein the drug-oligomer conjugate comprises salmon calcitonin coupled to two oligomeric moieties, wherein one oligomeric moiety is coupled to the lysine at the 11 position of the salmon calcitonin, and wherein one oligomeric moiety is coupled to the lysine at the 18 position of the salmon calcitonin.

50. The method of claim 49, wherein the oligomeric moiety coupled to the lysine at the 11 position comprises the structure $CH_3O(C_2H_4O)_7$—$(CH_2)_7$—$C(O)$— and wherein the oligomeric moiety coupled to the lysine at the 18 position of the salmon calcitonin comprises the structure $CH_3O(C_2H_4O)_7$—$(CH_2)_7$—$C(O)$—.

51. The method of claim 44, wherein the drug-oligomer conjugate is present as a substantially monodispersed mixture.

52. The method of claim 44, wherein the drug-oligomer conjugate is present as a monodispersed mixture.

53. The method of claim 44, wherein the drug-oligomer conjugate is amphiphilically balanced.

54. The method of claim 44, wherein the oligomeric moiety comprises a hydrophilic moiety and a lipophilic moiety.

55. The method of claim 44, wherein the oligomeric moiety is hydrophilic.

56. The method of claim 55, wherein the oligomeric moiety is polyethylene glycol.

57. The method of claim 44, wherein the oligomeric moiety is lipophilic.

58. The method of claim 57, wherein the oligomeric moiety is alkane.

59. The pharmaceutical composition of claim 17, wherein the bile salt is selected from the group consisting of taurocholate, taurodeoxycholate, cholate, deoxycholate and glycodeoxycholate.

60. The pharmaceutical composition of claim 17, wherein the bile salt is present in a concentration in the range of about 0.15% to about 10% bile salt.

61. The pharmaceutical composition of claim 17, wherein the bile salt is present in a concentration in the range of about 0.5% to about 5% bile salt.

62. The pharmaceutical composition of claim 17, wherein the pH of the composition is between 6.2 and 9.0.

63. The pharmaceutical composition of claim 17, further comprising a buffering component.

64. The pharmaceutical composition of claim 17, wherein the pharmaceutical composition is a liquid pharmaceutical composition.

65. The pharmaceutical composition of claim 64, wherein the liquid pharmaceutical composition is suitable for oral administration.

66. The pharmaceutical composition of claim 17, wherein the pharmaceutical composition is a solid dosage pharmaceutical composition.

67. The pharmaceutical composition of claim 17, wherein the composition is suitable for a route of administration selected from the group consisting of buccal, transdermal, peroral and nasal administration.

68. The pharmaceutical composition of claim 17, wherein the drug is a calcitonin polypeptide.

69. The pharmaceutical composition of claim 68, wherein the calcitonin polypeptide is salmon calcitonin.

70. The pharmaceutical composition of claim 69, wherein the drug-oligomer moiety comprises salmon calcitonin coupled to two oligomeric moieties, wherein one oligomeric moiety is coupled to the lysine at the 11 position of the salmon calcitonin and wherein one oligomeric moiety is coupled to the lysine at the 18 position of the salmon calcitonin.

71. The pharmaceutical composition of claim 17, wherein the drug-oligomer conjugate is present as a substantially monodispersed mixture.

72. The pharmaceutical composition of claim 17, wherein the drug-oligomer conjugate is present as a monodispersed mixture.

* * * * *

```
                        SEQUENCE LISTING

<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 1

Ser Gln Asn Tyr
1

<210> SEQ ID NO 2
<211> LENGTH: 4
<212> TYPE: PRT
<213> ORGANISM: Lymnaea stagnalis
<220> FEATURE:
<221> NAME/KEY: MOD_RES
<222> LOCATION: (4)..(4)
<223> OTHER INFORMATION: AMIDATION

<400> SEQUENCE: 2

Ala Pro Gly Trp
1

<210> SEQ ID NO 3
<211> LENGTH: 7
<212> TYPE: PRT
<213> ORGANISM: Panagrellus redivivus
<220> FEATURE:
<221> NAME/KEY: MOD_RES
<222> LOCATION: (7)..(7)
<223> OTHER INFORMATION: AMIDATION

<400> SEQUENCE: 3

Lys Ser Ala Tyr Met Arg Phe
1               5

<210> SEQ ID NO 4
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: AMIDATION
```

```
<400> SEQUENCE: 4

Ser Ala Leu Met Phe
1               5
```